US008637448B2

(12) United States Patent
Fay et al.

(10) Patent No.: US 8,637,448 B2
(45) Date of Patent: Jan. 28, 2014

(54) RECOMBINANT FACTOR VIII HAVING ENHANCED STABILITY FOLLOWING MUTATION AT THE A1-C2 DOMAIN INTERFACE

(75) Inventors: Philip J. Fay, Pittsford, NY (US); Hironao Wakabayashi, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/231,948

(22) Filed: Sep. 13, 2011

(65) Prior Publication Data
US 2012/0065136 A1    Mar. 15, 2012

Related U.S. Application Data

(60) Provisional application No. 61/382,919, filed on Sep. 14, 2010.

(51) Int. Cl.
*A61K 38/37* (2006.01)
*C07K 14/755* (2006.01)

(52) U.S. Cl.
USPC .......... 514/1.1; 514/13.5; 514/13.7; 514/14.1

(58) Field of Classification Search
None
See application file for complete search history.

(56) References Cited

U.S. PATENT DOCUMENTS

| | | | | |
|---|---|---|---|---|
| 5,891,675 A * | 4/1999 | Lin et al. | ...................... | 435/69.1 |
| 6,593,294 B1 * | 7/2003 | Baru et al. | ................... | 514/13.7 |
| 2007/0265199 A1 * | 11/2007 | Fay et al. | ........................ | 514/12 |
| 2009/0118184 A1 | 5/2009 | Fay et al. | | |
| 2009/0118185 A1 | 5/2009 | Fay et al. | | |
| 2009/0318344 A1 * | 12/2009 | Camire et al. | ................... | 514/12 |

OTHER PUBLICATIONS

Wakabayashi et al (Abstract 3176, 51st ASH annual meeting, 2009).*
Michael McDevitt (Scheduling your 2009 ASH annual meeting visit).*
Wakabayashi et al, Increasing hydrophobicity or disulfide bridging at the factor VIII A1 and C2 domain interface enhances procofactor stability, The Journal of Biological Chemistry, vol. 286, No. 29, pp. 25748-25755, 2011.*
Wakabayashi et al, Role of the interaction between the factor VIII A1 domain Ca2+ binding site and C2 domain on activity and stability, Abstract, PP-MO-155, 22nd Congress of the International Society on Thrombosis and Haemostasis, Jul. 13, 2009.*
Healey et al, The cDNA and derived amino acid sequence of porcine factor VIII, Blood, vol. 88, No. 11 (Dec. 1). 1996: pp. 4209-4214.*
Wakabayashi et al., "Role of the Interaction between the Factor VIII A1 Domain Ca2+ binding Site and C2 domain on Activity and Stability," 22nd Congress of the International Society on Thrombosis and Haemostasis (abstract and poster) (Jul. 13, 2009).
Wakabayashi et al., "Increasing Hydrophobicity and DiSulfide Bridging Between A1 and C2 Subunits Improves Factor VIII Stability," American Society of Hematology 52nd Annual Meeting and Exposition (abstract and poster) Blood 114: Abstract 3176 (Nov. 2009); poster presentation (Dec. 2009).
Wakabayashi et al., "Increasing Hydrophobicity or Disulfide Bridging at the Factor VIII A1 and C2 Domain Interface Enhances Procofactor Stability," J. Biol. Chem. 286:25748-25755 (May 31, 2011).
Shen et al., "The Tertiary Structure and Domain Organization of Coagulation Factor VIII," Blood 111(3):1240-1247 (2008).
Pemberton et al., "A Molecular Model for the Triplicated A Domains of Human Factor VIII Based on the Crystal Structure of Human Ceruloplasmin," Blood 89(7):2413-2421 (1997).
Sammond et al., "Structure-Based Protocol for Identifying Mutations That Enhance Protein-Protein Binding Affinities," J. Mol. Biol. 371:1392-1404 (2007).
Pipe et al., "Mild Hemophilia A Caused by Increased Rate of Factor VIII A2 Subunit Dissociation: Evidence for Nonproteolytic Inactivation of Factor Villa In vivo," Blood 93:176-183 (1999).
Pipe et al., "Hemophilia A mutations associated with 1-stage/2-stage activity discrepancy disrupt protein-protein interactions within the triplicated A domains of thrombin-activated factor Villa," Blood 97:685-691 (2001).
Hakeos et al., "Hemophilia A Mutations Within the Factor VIII A2-A3 Subunit Interface Destabilize Factor Villa and Cause One-Stage/Two-Stage Activity Discrepancy," Thromb. Haemost. 88:781-787 (2002).

* cited by examiner

*Primary Examiner* — Cecilia J Tsang
*Assistant Examiner* — Sergio Coffa
(74) *Attorney, Agent, or Firm* — LeClairRyan, A Professional Corporation

(57) ABSTRACT

The invention relates to a recombinant factor VIII that includes one or more mutations at an interface of A1 and C2 domains of recombinant factor VIII. The one or more mutations include substitution of one or more amino acid residues with either a cysteine or an amino acid residue having a higher hydrophobicity. This results in enhanced stability of factor VIII. Methods for making the recombinant factor VIII, pharmaceutical compositions containing the recombinant factor VIII, and use of the recombinant factor VIII for treating hemophilia A are also disclosed.

10 Claims, 13 Drawing Sheets

Partial A1 Domain Sequence Alignment Starting From Amino Acid Residue A100 of Human Factor VIII

```
Human     (100-140, SEQ ID NO:2)  AVGVSYWKASEGAEYDDQTSQREKEDDKVFPGGSHTYVWQV
Porcine   (SEQ ID NO:3)            AVGVSFWKSSEGAEYEDHTSQREKEDDKVLPGKSQTYVWQV
Canine    (SEQ ID NO:4)            AVGVSYWKASEGAEYEDQTSQKEKEDDNVIPGESHTYVWQV
Mouse     (SEQ ID NO:5)            AVGVSYWKASEGDEYEDQTSQMEKEDDKVFPGCESHTYVWQV
Rabbit    (SEQ ID NO:6)            AVGVSYWKASEGAEYDDQTSQREKEDDKIFPGESHTYVWQV
Bat       (SEQ ID NO:7)            AVGVSYWKASEGAEYEDETSKTEKEDDRVIPGESHTYVWHV
Rat       (SEQ ID NO:8)            AVGMSFWKASEGAAYDDHSSPAEKDDDKVLPGESHTYAWQV
Sheep     (SEQ ID NO:9)            ATGVSYWKSSEGAAYKDETSQREKEDDKVIPGKSHTYVWHI Consensus (SEQ ID NO:10)           AXGXSXWKXSEGXXYXDXXSXXEKXDXXXFGXSXTYXWXX
```

*FIG. 1*

Partial C2 Domain Sequence Alignment Starting from Amino Acid Residue Q2231 of Human Factor VIII

```
Human    (2231-2334, SEQ ID No:2)   QVDFQKTMKVTGVTTQGVKSLLTSMYVKEFLISSSQDGHQWTLFFQNGKV
Porcine  (SEQ ID NO:11)              QVDLQKTMKVTGITTQGVKSLLSSMYVKEFLVSSSQDGRRWTLFLQDGHT
Canine   (SEQ ID NO:12)              QVDFRKTMKVTGITTQGVKSLLISMYVKEFLISSSQDGHNWTLFLQNGKV
Mouse    (SEQ ID NO:13)              QVDLQKTMKVTGITTQGVKSLPTSMFVKEFLISSSQDGHNWTQILYNGKV
Rabbit   (SEQ ID NO:14)              QVDLRKTMKVTGITTQGVKSLLTSMYVTEFLISSSQDGHNWTLVLQKGRL
Bat      (SEQ ID NO:15)              QVDFQKTMKVTGITTQGVKSLLTSMYVKEFLISSSQDGHNWTPFLQNGKV
Rat      (SEQ ID NO:16)              QVDLQRTVKVTGVVTQGQARSLLTAMFVKKFLVSTSQDGRHWTHVLQDGKV
Sheep    (SEQ ID NO:17)              QVDFQKTMRVTGITTQGVKSLLITSMYVKEFLISSSQEGHNWTPFLQNGKV Consensus (SEQ ID NO:18)             QVDXXXTXXVTGXXTQGXXSLXXXXMXVXXFLXSXSQGXXWTXXXXXGXX Human    (SEQ ID No:2 cont.)         KVFQGNQDSFTPVVNSLDPPLLTRYLRIHPQSWVHQIALRMEVLGCEAQDLY
Porcine  (SEQ ID NO:11 cont.)        KVFQGNQDSSTPVVNALDPPLLFTRYLRIHPTSWAQHIALRLEVLGCEAQDLY
Canine   (SEQ ID NO:12 cont.)        KVFQGNRDSSTPVVNRLEPPLVARYVRLHPQSWARHIALRLEVLGCDTQQPA
Mouse    (SEQ ID NO:13 cont.)        KVFQGNQDSSTPMMNSLDPPLLTRYLRIHPQIWEHQIALRLEILGCEAQQOY
Rabbit   (SEQ ID NO:14 cont.)        KVFQGNQDSFTPVLMSLDPPLLTRYLRIHPKSWVHQIALRLEVLGCEAQQLY
Bat      (SEQ ID NO:15 cont.)        KVFQGNQDSFTPVLNSLDPPLLTRYLRIHPQSWVHQIALRLEVLGCEAQQLY
Rat      (SEQ ID NO:16 cont.)        KVFQGNQDSFTPVVNSLHPPRFTRYLRIHPQVWERQIALRLEILGCEAQQLD
Sheep    (SEQ ID NO:17 cont.)        KVFQGNQDSFTPVVNTLDPPLFTRFLRIHPQSWVHHIALRLEFWGCEAQQQY Consensus (SEQ ID NO:18 cont.)       KVFXGXXDXXTPXXNXLXPPXXXRXXXPXHPXXWXXXIALRXEXXGCXXQXX
```

FIG. 2 ns of (purified) plasma or the recombinant protein.
RECOMBINANT FACTOR VIII HAVING ENHANCED STABILITY FOLLOWING MUTATION AT THE A1-C2 DOMAIN INTERFACE This application claims the priority benefit of U.S. Provisional Patent Application Ser. No. 61/382,919, filed Sep. 14, 2010, which is hereby incorporated by reference in its entirety.

This invention was made with government support under grant number HL38199 and HL76213 awarded by the National Institutes of Health. The government has certain rights in the invention.

BACKGROUND OF THE INVENTION

Hemophilia A, the most common of the severe, inherited bleeding disorders, results from a deficiency or defect in the plasma protein factor VIII. There is no cure for Hemophilia A and treatment consists of replacement therapy using preparations of (purified) plasma or the recombinant protein.

Factor VIII circulates as a non-covalent, metal ion-dependent heterodimer. This procofactor form of the protein contains a heavy chain (HC) comprised of A1(a1)A2(a2)B domains and a light chain (LC) comprised of (a3)A3C1C2 domains, with the lower case a representing short (~30-40 residue) segments rich in acidic residues (see Fay, "Activation of Factor VIII and Mechanisms of Cofactor Action," *Blood Rev.* 18:1-15 (2004)). Factor VIII is activated by proteolytic cleavages at the A1A2, A2B and A3A3 junctions catalyzed by thrombin or factor Xa. The product of this reaction, factor VIIIa, is a heterotrimer comprised of subunits designated A1, A2, and A3C1C2 that functions as a cofactor for the serine protease factor IXa in the membrane-dependent conversion of zymogen factor X to the serine protease, factor Xa (see Fay, "Activation of Factor VIII and Mechanisms of Cofactor Action," *Blood Rev.* 18:1-15 (2004)).

Reconstitution studies have shown that the factor VIII heterodimeric structure is supported by both electrostatic and hydrophobic interactions (Fay, "Reconstitution of Human Factor VIII from Isolated Subunits," *Arch Biochem Biophys.* 262:525-531 (1988); Ansong et al., "Factor VIII A1 Domain Residues 97-105 Represent a Light Chain-interactive Site," *Biochemistry* 45:13140-13149 (2006)), and the inter-chain affinity is further strengthened by factor VIII binding von Willebrand factor (Fay, "Reconstitution of Human Factor VIII from Isolated Subunits," *Arch Biochem Biophys.* 262: 525-531 (1988); Kaufman et al., "Regulation of Factor VIII Expression and Activity by von Willebrand Factor," *Thromb Haemost.* 82:201-208 (1999)). Metal ions also contribute to the inter-chain affinity and activity parameters (Wakabayashi et al., "Metal Ion-independent Association of Factor VIII Subunits and the Roles of Calcium and Copper Ions for Cofactor Activity and Inter-subunit Affinity," *Biochemistry* 40:10293-10300 (2001)). Calcium is required to yield the active factor VIII conformation. Mutagenesis studies mapped a calcium-binding site to a segment rich in acidic residues within the A1 domain (residues 110-126) and identified specific residues within this region prominent in the coordination of the ion (Wakabayashi et al., "Residues 110-126 in the A1 Domain of Factor VIII Contain a $Ca^{2+}$ Binding Site Required for Cofactor Activity," *J Biol Chem.* 279:12677-12684 (2004)). A recent intermediate resolution X-ray structure (Shen et al., "The Tertiary Structure and Domain Organization of Coagulation Factor VIII," *Blood* 111:1240-1247 (2008)) confirmed this calcium-binding site as well as suggested a second potential site within the A2 domain. This structure also showed occupancy of the two type 1 copper ion sites within the A1 and A3 domains. Earlier functional studies have shown that copper ions facilitate the association of the heavy and light chains to form the heterodimer, increasing the inter-chain affinity by several-fold at physiologic pH (Fay et al., "Human Factor VIIIa Subunit Structure: Reconstruction of Factor VIIIa from the Isolated A1/A3-C1-C2 Dimer and A2 Subunit," *J Biol Chem.* 266:8957-8962 (1991); Wakabayashi et al., "pH-dependent Association of Factor VIII Chains: Enhancement of Affinity at Physiological pH by $Cu^{2+}$," *Biochim Biophys Acta.* 1764:1094-1101 (2006); Ansong et al., "Factor VIII A3 Domain Residues 1954-1961 Represent an A1 Domain-Interactive Site," *Biochemistry* 44:8850-8857 (2005)).

The instability of factor VIIIa results from weak electrostatic interactions between the A2 subunit and the A1/A3C1C2 dimer (Fay et al., "Human Factor VIIIa Subunit Structure: Reconstruction of Factor VIIIa from the Isolated A1/A3-C1-C2 Dimer and A2 Subunit," *J Biol Chem.* 266: 8957-8962 (1991); Lollar et al., "pH-dependent Denaturation of Thrombin-activated Porcine Factor VIII," *J Biol Chem.* 265:1688-1692 (1990)) and leads to dampening of factor Xase activity (Lollar et al., "Coagulant Properties of Hybrid Human/Porcine Factor VIII Molecules," *J Biol Chem.* 267: 23652-23657 (1992); Fay et al., "Model for the Factor VIIIa-dependent Decay of the Intrinsic Factor Xase: Role of Subunit Dissociation and Factor IXa-catalyzed Proteolysis," *J Biol Chem.* 271:6027-6032 (1996)). Limited information is available regarding the association of the A2 subunit in factor VIIIa, and residues in both the A1 and A3 domains appear to make contributions to the retention of this subunit. Several factor VIII point mutations have been shown to facilitate the dissociation of A2 relative to WT and these residues localize to either the A1-A2 domain interface (Pipe et al., "Mild Hemophilia A Caused by Increased Rate of Factor VIII A2 Subunit Dissociation: Evidence for Nonproteolytic Inactivation of Factor VIIIa in vivo," *Blood* 93:176-183 (1999); Pipe et al., "Hemophilia A Mutations Associated with 1-stage/2-stage Activity Discrepancy Disrupt Protein-protein Interactions within the Triplicated A Domains of Thrombin-activated Factor VIIIa," *Blood* 97:685-691 (2001)) or the A2-A3 domain interface (Hakeos et al., "Hemophilia A Mutations within the Factor VIII A2-A3 Subunit Interface Destabilize Factor VIIIa and Cause One-stage/Two-stage Activity Discrepancy," *Thromb Haemost.* 88:781-787 (2002)). These factor VIII variants demonstrate a characteristic one-stage/two-stage assay discrepancy (Duncan et al., "Familial Discrepancy Between the One-stage and Two-stage Factor VIII Methods in a Subgroup of Patients with Haemophilia A," *Br J Haematol.* 87:846-848 (1994); Rudzki et al., "Mutations in a Subgroup of Patients with Mild Haemophilia A and a Familial Discrepancy Between the One-stage and Two-stage Factor VIII:C Methods," *Br J Haematol.* 94:400-406 (1996)), with significant reductions in activity values determined by the latter assay as a result of increased rates of A2 subunit dissociation.

Significant interest exists in stabilizing factor VIIIa, since a more stable form of the protein would represent a superior therapeutic for hemophilia A, potentially requiring less material to treat the patient (Fay et al., "Mutating Factor VIII: Lessons from Structure to Function," *Blood Reviews* 19:15-27 (2005)). To this end, preparations of factor VIII have been described where mutations have been made in the recombinant protein to prevent the dissociation of the A2 subunit by introducing novel covalent bonds between A2 and other factor VIII domains (Pipe et al., "Characterization of a Genetically Engineered Inactivation-resistant Coagulation Factor VIIIa," *Proc Natl Acad Sci USA* 94:11851-11856 (1997); Gale et al., "An Engineered Interdomain Disulfide Bond Stabilizes Human Blood Coagulation Factor VIIIa," *J. Thromb. Haemostasis* 1:1966-1971 (2003)). However, it has since been suggested that these types of mutation may not be desirable in a therapeutic factor VIII, because they substantially eliminate means for down-regulation. This situation could yield a prothrombotic condition, which may cause harm. Thus, it would be desirable to enhance the stability of both factor VIII and factor VIIIa, but in a manner that minimizes the likelihood of promoting prothrombotic conditions.

In U.S. Patent Application Publ. No. 20090118184, a number of recombinant factor VIII proteins are identified that possess one or more mutations that result in enhanced stability of both factor VIII and factor VIIIa. These recombinant factor VIII proteins have one or more substitutions of a charged amino acid residue with a hydrophobic amino acid residue at either or both of the A1-A2 or A2-A3 domain interfaces. Despite the improvements made in the stability of recombinant factor VIII proteins (and their active forms, factor VIIIa), the need for further improvements continue to exist.

The intermediate resolution X-ray structures of factor VIII (Shen et al., "The Tertiary Structure and Domain Organization of Coagulation Factor VIII," *Blood* 111:1240-1247 (2008); Ngo et al., "Crystal Structure of Human Factor VIII: Implications for the Formation of the Factor IXa:Factor VIIIa Complex," *Structure* 16:597-606 (2008)) show close contact between A1 (heavy chain) and C2 (light chain) domains. It was recently reported that a factor VIII variant lacking the C2 domain retained the capacity to bind phospholipid membranes, albeit with a marked reduction in affinity (Wakabayashi et al., "Factor VIII Lacking the C2 Domain Retains Cofactor Activity in vitro," *J. Biol. Chem* 285:25176-25184 (2010)), supporting a direct role for the C1 domain in this interaction. Furthermore, deletion of the C2 domain did not grossly alter a number of functional properties including the rate of procofactor activation by thrombin, affinity of factor VIIIa for factor IXa, $K_m$ of factor Xase for substrate factor X, or $k_{cat}$ for factor Xa generation. However, this deletion did significantly destabilize the cofactor, as judged by increased rates of activity decay following exposure to elevated temperature or chemical denaturants. While contacts between the A1 and C2 domains of factor VIII appear to contribute to protein, and in particular heterodimer stability, little information is available on specific interactions and their functional significance. It would be desirable, therefore, to identify amino acid residues that can be modified to enhance stability between the A1 (heavy chain) and C2 (light chain) domains.

The present invention is directed to overcoming these and other deficiencies in the art.

SUMMARY OF THE INVENTION

A first aspect of the present invention relates to a recombinant factor VIII that includes one or more mutations at an interface of A1 and C2 domains of recombinant factor VIII. This results in enhanced stability of factor VIII. The one or more mutations include substitution of one or more amino acid residues with either a cysteine or an amino acid residue having a higher hydrophobicity.

According to one embodiment, the recombinant factor VIII includes one or more mutations at an interface of A1 and C2 domains of recombinant factor VIII that result in enhanced stability of factor VIII, wherein the one or more mutations comprise substitution of one or more amino acid residues with an amino acid residue having a higher hydrophobicity.

According to another embodiment, the recombinant factor VIII includes (i) two or more mutations at an interface of A1 and C2 domains of recombinant factor VIII, wherein the two or more mutations comprise substitution of two or more amino acid residues with a Cysteine residue to afford a disulfide bond between the A1 and C2 domains; and (ii) one or more mutations at an interface of A1 and A2 domains or an interface of A2 and A3 domains of recombinant factor VIII, said one or more mutations comprising substitution of one or more charged amino acid residues with a hydrophobic amino acid residue. The recombinant factor VIII possessing these mutations exhibits enhanced stability of both factor VIII and factor VIIIa.

A second aspect of the present invention relates to the recombinant factor VIII according to the first aspect of the present invention, wherein the recombinant factor VIII further includes one or more of (i) factor IXa and/or factor X binding domains modified to enhance the affinity of the recombinant factor VIII for one or both of factor IXa and factor X; (ii) modified sites that enhance secretion in culture; (iii) modified serum protein binding sites that enhance the circulating half-life thereof; (iv) at least one glycosylation recognition sequence that is effective in decreasing antigenicity and/or immunogenicity thereof; (v) a modified A1 domain calcium-binding site that improves specific activity of the recombinant factor VIIIa; (vi) modified activated protein C-cleavage site; (vii) a modified A1 and A2 domain interface; and (viii) a modified A2 and A3 domain interface.

A third aspect of the present invention relates to a pharmaceutical composition that includes the recombinant factor VIII according to the present invention.

A fourth aspect of the present invention relates to an isolated nucleic acid molecule encoding a recombinant factor VIII of the present invention. Also included within this aspect of the present invention are recombinant DNA expression systems that contain a DNA molecule encoding the recombinant factor VIII of the present invention, and recombinant host cells that contain the DNA molecule and/or recombinant expression system.

A fifth aspect of the present invention relates to a method of making a recombinant factor VIII that includes: growing a host cell according to the fourth aspect of the present invention under conditions whereby the host cell expresses the recombinant factor VIII; and isolating the recombinant factor VIII.

A sixth aspect of the present invention relates to a method of treating an animal for hemophilia A. This method of treatment includes: administering to an animal exhibiting hemophilia A an effective amount of the recombinant factor VIII of the present invention, whereby the animal exhibits effective blood clotting following vascular injury.

The present invention demonstrates that a number of residues at the interface of A1 and C2 domains do not participate in non-covalent bonding, but instead may be destabilizing to factor VIII structure. Replacement of these residues with more hydrophobic residues—with the aim of increasing the buried hydrophobic area and reducing the buried hydrophilic area—was shown in the accompanying Examples to enhance inter-domain binding affinity. Stability parameters were assessed by following the activity of the factor VIII variants. Results from these studies demonstrated that a number of mutations yielded increased stability parameters. These stabilized variants of factor VIII and activated cofactor VIIIa should afford an improved therapeutic for treatment of hemophilia A.

To explore the role of this region in factor VIII and factor VIIIa stability, a variant containing a disulfide bond between A1 and C2 domains was generated by mutating Arg121 and Leu2302 to Cys (R121C-L2302C) and a second variant was generated by substituting a bulkier hydrophobic group (Ala108Ile) to better occupy a cavity between A1 and C2 domains. Disulfide bonding in the R121C-L2302C variant was >90% efficient as judged by western blots. Binding affinity between the Ala108Ile A1 and A3C1C2 subunits was increased ~3.7-fold in the variant compared with WT as judged by changes in fluorescence of acrylodan labeled-A1 subunits. Factor VIII thermal and chemical stability were monitored following rates of loss of factor VIII activity at 57° C. or in guanidinium by factor Xa generation assays. The rate of decay of factor VIIIa activity was monitored at 23° C. following activation by thrombin. Both R121C-L2302C and Ala108Ile variants showed up to ~4-fold increases in thermal stability but minimal improvements in chemical stability. The purified A1 subunit of Ala108Ile reconstituted with the A3C1C2 subunit showed a ~4.6-fold increase in thermal stability while reconstitution of the variant A1 with a truncated A3C1 subunit showed similar stability values as compared with WT A1. Together, these results suggest that altering contacts at this A1-C2 junction by covalent modification or increasing hydrophobicity increases inter-chain affinity and functionally enhances factor VIII stability. Moreover, by combining these mutations with one or more mutations at the A1-A2 and/or A2-A3 domain interfaces, including Asp519Ala, Asp519Val, Glu665Ala, Glu665Val, Glu1984Ala, and Glu1984Val, double and triple mutants displayed ~2-10 fold increases in the stability of factor VIIIa.

BRIEF DESCRIPTION OF THE DRAWINGS

FIG. 1 shows alignment of partial A1 domain sequences of eight mammalian factor VIII molecules starting from amino acid residue A100 of human factor VIII. The partial amino acid sequences are from human factor VIII (residues 100-140 of SEQ ID NO: 2); pig factor VIII (SEQ ID NO: 3); canine factor VIII (SEQ ID NO: 4); mouse factor VIII (SEQ ID NO: 5); rabbit factor VIII (SEQ ID NO: 6); bat factor VIII (SEQ ID NO: 7); rat factor VIII (SEQ ID NO: 8); and sheep factor VIII (SEQ ID NO: 9). The figure also shows the consensus amino acid sequence (SEQ ID NO: 10) for the partial A1 domain. Underlined residues represent a C2 domain interface of the A1 domain.

FIG. 2 shows alignment of partial C2 domain sequences from eight mammalian factor VIII molecules starting from amino acid residue Q2231 of human factor VIII. The partial amino acid sequences are from human factor VIII (residues 2231-2334 of SEQ ID NO: 2); pig factor VIII (SEQ ID NO: 11); canine factor VIII (SEQ ID NO: 12); mouse factor VIII (SEQ ID NO: 13); rabbit factor VIII (SEQ ID NO: 14); bat factor VIII (SEQ ID NO: 15); rat factor VIII (SEQ ID NO: 16); and sheep factor VIII (SEQ ID NO: 17). The figure also shows the consensus amino acid sequence (SEQ ID NO: 18) for the partial C2 domain. Underlined residues represent an A1 domain interface of the C2 domain.

FIGS. 3A-C illustrate a model of selected residues at the A1-C2 domain interface. In FIG. 3A, the molecular surface of the factor VIII X-ray crystal structure, drawn by Swiss PDB viewer, shows the A1 domain (residues 1-336) in yellow, A2 domain (residues 373-711) in blue, A3 domain (residues 1690-2020) in red, C1 domain (residues 2021-2169) in green, and C2 domain (residues 2170-2332) in grey (FIG. 3A). Higher magnification of the A1-C2 contact region (yellow circle) is presented in FIGS. 3B-C. Side chains of Arg121 and Leu2302 (drawn as stick models) mutated to Cys residues are modeled by Swiss PDB viewer (FIG. 3B). In FIG. 3C, residues surrounding Ala108 (Leu2302, Ala2328, and Gln2329) are highlighted as stick models. Cβ carbon of Ala108, Cδ of Leu2302, Cβ of Ala2328, and Cγ of Gln2329 are indicated by arrows (FIG. 3C, left panel). Ala108 mutated to Ile was modeled by Swiss PDB viewer (FIG. 3C, right panel). In the stick models hydrogen, carbon, oxygen, nitrogen, and sulfur are colored as cyan, white, red, blue, and yellow, respectively. Ribbon structures represent α-helix (red) and β-strand (green).

FIG. 4 is a Western blot analysis of R121C-L2302C and WT factor VIII. Purified WT and mutant factor VIII proteins were electrophoresed under non-reducing (lanes 1, 2, 5, and 6) or reducing (lanes 3, 4, 7, and 8) conditions, transferred, and probed with 58.12 (anti-A1 domain antibody, lane 1-4) or 2D2 (anti-A3 domain antibody, lane 5-8). Protein bands were visualized by chemifluorescence as described in the accompanying Examples. Shown are WT (lane 1, 3, 5, and 7) and the R121C-L2302C factor VIII variant (lane 2, 4, 6, and 8) proteins.

FIG. 5 is a graph showing the binding affinity of A1 subunit from WT or Ala108Ile for the A3C1C2 subunit. Acrylodan-labeled A1 subunit from WT (circles) or Ala108Ile (triangles) was titrated with A3C1C2 and binding was detected by the change of fluorescence as described in the accompanying Examples. Data points averaged from 3 separate determinations were fitted to a quadratic equation curve by non-linear least squares regression.

FIGS. 6A-C are graphs that illustrate factor VIII R121C-L2302C and Ala108Ile variant stability. FIG. 6A shows the factor VIII activity decay at elevated temperature. Factor VIII (4 nM) was incubated at 57° C. and at the indicated times aliquots were removed and activity was measured by factor Xa generation assays as described in the accompanying Examples. Data were fitted to a single exponential decay curve by non-linear least squares regression. FIG. 6B shows the inhibition of factor VIII by guanidinium. FVIII (50 nM) in 0-1.2 M guanidinium chloride was incubated for 2 hrs at 23° C., diluted 1/50 and factor VIII activity was measured by factor Xa generation. Data were fitted to a linear equation by least squares regression. Bars represent standard error values of 3 measurements. FIG. 6C shows factor VIIIa decay. Thrombin-activated factor VIIIa (1.5 nM) was incubated at 23° C., aliquots were taken at indicated time points and activity was measured by factor Xa generation assay as described in the accompanying Examples. Data were fitted to a single exponential decay curve by non-linear least squares regression. Symbols denote WT (circles), R121C-L2302C (triangles), and Ala108Ile (squares). Each point represents the value averaged from three separate determinations.

FIGS. 7A-B are graphs showing the thermal stability of A1 subunit reconstituted with A3C1C2 or A3C1 subunit. Thermal decay of reconstituted heterodimer of A1 subunit from WT (circles) or Ala108Ile (triangles) with WT A3C1C2 subunit at 55° C. (FIG. 7A) or A3C1 subunit at 52° C. (FIG. 7B) was detected by residual factor VIIIa activity following addition of A2 subunit as described in the accompanying Examples. Data were fitted to a single exponential decay curve by non-linear least squares regression. Data points averaged from 3 separate determinations were fitted to a single exponential decay curve to obtain rates.

FIGS. 8A-C are bar graphs comparing the thermal stability (FIG. 8A), chemical stability in the presence of guanidinium (FIG. 8B), and factor VIIIa decay (FIG. 8C) of WT and combination mutants. The combination mutants include one or more of the A1-C2 domain interface mutations (A108I or R121C-L2302C) in combination with one or more A1-A2 or A2-A3 domain interface mutations. Factor VIII activity decay, guanidinium inhibition, and factor VIIIa decay were measured as described in the accompanying Examples.

DETAILED DESCRIPTION OF THE INVENTION

Figure 3A:
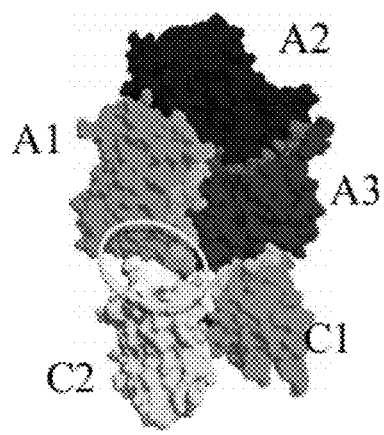

The present invention relates to a recombinant factor VIII having one or more mutations that result in enhanced stability of factor VIII, in particular improved thermal and/or chemical stability of factor VIII.

The recombinant factor VIII of the present invention can be prepared by modifying the amino acid sequence of a wild-type factor VIII or a mutant factor VIII that has otherwise been modified to affect other properties of the factor VIII, such as antigenicity, factor VIIIa stability, circulating half-life, protein secretion, affinity for factor IXa and/or factor X, altered factor VIII-inactivation cleavage sites, immunogenicity, shelf-life, etc.

Suitable wild-type factor VIII that can be modified in accordance with the present invention can be from various animals including, without limitation, mammals such as humans (see, e.g., GenBank Accession Nos. AAA52484 (amino acid) and K01740 (nucleotide); and GenBank Accession Nos. CAD97566 (amino acid) and AX746360 (nucleotide), which are hereby incorporated by reference in their entirety), rats (see, e.g., GenBank Accession Nos. AAQ21580 (amino acid) and AY362193 (nucleotide), which are hereby incorporated by reference in their entirety), mice (see, e.g., GenBank Accession Nos. AAA37385 (amino acid) and L05573 (nucleotide), which are hereby incorporated by reference in their entirety), guinea pigs, dogs (see, e.g., GenBank Accession Nos. AAB87412 (amino acid) and AF016234 (nucleotide); and GenBank Accession Nos. AAC05384 (amino acid) and AF049489 (nucleotide), which are hereby incorporated by reference in their entirety), cats, monkeys, chimpanzees (see, e.g., GenBank Accession Nos. XP_529212 (amino acid) and XM_529212 (nucleotide), which are hereby incorporated by reference in their entirety), orangutans, cows, horses, sheep, pigs (see, e.g., GenBank Accession Nos. NP_999332 (amino acid) and NM_214167 (nucleotide), which are hereby incorporated by reference in their entirety), goats, rabbits, and chickens. These and other sequences are also available electronically via the Haemophilia A Mutation, Structure, Test and Resource Site (or HAMSTeRS), which further provides an alignment of human, porcine, murine, and canine factor VIII proteins. Thus, the conservation and homology among mammalian factor VIII proteins is well known.

By way of example, the human factor VIII cDNA nucleotide and predicted amino acid sequences are shown below in SEQ ID NOs: 1 and 2, respectively. Human factor VIII is synthesized as an approximately 300 kDa single chain protein with internal sequence homology that defines the "domain" sequence $NH_2$-A1-A2-B-A3-C1-C2-COOH. In a factor VIII molecule, a "domain," as used herein, is a continuous sequence of amino acids that is defined by internal amino acid sequence identity and sites of proteolytic cleavage by thrombin. Unless otherwise specified, factor VIII domains include the following amino acid residues, when the sequences are aligned with the human amino acid sequence (SEQ ID NO: 2):

A1, residues $Ala_1$-$Arg_{372}$;
A2, residues $Ser_{373}$-$Arg_{740}$;
B, residues $Ser_{741}$-$Arg_{1648}$;
A3, residues $Ser_{1690}$-$Ile_{2032}$;
C1, residues $Arg_{2033}$-$Asn_{2172}$; and
C2, residues $Ser_{2173}$-$Tyr_{2332}$.

The A3-C1-C2 sequence includes residues $Ser_{1690}$-$Tyr_{2332}$. The remaining sequence, residues $Glu_{1649}$-$Arg_{1689}$, is usually referred to as the factor VIII light chain activation peptide. Factor VIII is proteolytically activated by thrombin or factor Xa, which dissociates it from von Willebrand factor, forming factor VIIIa, which has procoagulant function. The biological function of factor VIIIa is to increase the catalytic efficiency of factor IXa toward factor X activation by several orders of magnitude. Thrombin-activated factor VIIIa is a 160 kDa A1/A2/A3-C1-C2 heterotrimer that forms a complex with factor IXa and factor X on the surface of platelets or monocytes. A "partial domain" as used herein is a continuous sequence of amino acids forming part of a domain.

As used herein, a residue corresponding to a particular position refers to the residue at that position in wild type human factor VIII; however the same position will retain its numbering even though the residue may be at a different location in a recombinant factor VIII of the present invention. For example, a B domainless factor VIII lacks the B domain yet it still retains the conventional residue numbering for domains A3, C1, and C2.

The cDNA encoding wild-type human factor VIII has a nucleotide sequence of SEQ ID NO: 1, as follows:

```
  1 GCCACCAGAA GATACTACCT GGGTGCAGTG GAACTGTCAT
    GGGACTATAT

51 GCAAAGTGAT CTCGGTGAGC TGCCTGTGGA CGCAAGATTT
    CCTCCTAGAG

101 TGCCAAAATC TTTTCCATTC AACACCTCAG TCGTGTACAA
    AAAGACTCTG

151 TTTGTAGAAT TCACGGATCA CCTTTTCAAC ATCGCTAAGC
    CAAGGCCACC

201 CTGGATGGGT CTGCTAGGTC CTACCATCCA GGCTGAGGTT
    TATGATACAG

251 TGGTCATTAC ACTTAAGAAC ATGGCTTCCC ATCCTGTCAG
    TCTTCATGCT

301 GTTGGTGTAT CCTACTGGAA AGCTTCTGAG GGAGCTGAAT
    ATGATGATCA

351 GACCAGTCAA AGGGAGAAAG AAGATGATAA AGTCTTCCCT
    GGTGGAAGCC

401 ATACATATGT CTGGCAGGTC CTGAAAGAGA ATGGTCCAAT
    GGCCTCTGAC

451 CCACTGTGCC TTACCTACTC ATATCTTTCT CATGTGGACC
    TGGTAAAAGA

501 CTTGAATTCA GGCCTCATTG GAGCCCTACT AGTATGTAGA
    GAAGGGAGTC

551 TGGCCAAGGA AAAGACACAG ACCTTGCACA AATTTATACT
    ACTTTTTGCT

601 GTATTTGATG AAGGGAAAAG TTGGCACTCA GAAACAAAGA
    ACTCCTTGAT

651 GCAGGATAGG GATGCTGCAT CTGCTCGGGC CTGGCCTAAA
    ATGCACACAG

701 TCAATGGTTA TGTAAACAGG TCTCTGCCAG GTCTGATTGG
    ATGCCACAGG

751 AAATCAGTCT ATTGGCATGT GATTGGAATG GGCACCACTC
    CTGAAGTGCA
```

```
 801  CTCAATATTC CTCGAAGGTC ACACATTTCT TGTGAGGAAC
      CATCGCCAGG
 851  CGTCCTTGGA AATCTCGCCA ATAACTTTCC TTACTGCTCA
      AACACTCTTG
 901  ATGGACCTTG GACAGTTTCT ACTGTTTTGT CATATCTCTT
      CCCACCAACA
 951  TGATGGCATG GAAGCTTATG TCAAAGTAGA CAGCTGTCCA
      GAGGAACCCC
1001  AACTACGAAT GAAAAATAAT GAAGAAGCGG AAGACTATGA
      TGATGATCTT
1051  ACTGATTCTG AAATGGATGT GGTCAGGTTT GATGATGACA
      ACTCTCCTTC
1101  CTTTATCCAA ATTCGCTCAG TTGCCAAGAA GCATCCTAAA
      ACTTGGGTAC
1151  ATTACATTGC TGCTGAAGAG GAGGACTGGG ACTATGCTCC
      CTTAGTCCTC
1201  GCCCCCGATG ACAGAAGTTA TAAAAGTCAA TATTTGAACA
      ATGGCCCTCA
1251  GCGGATTGGT AGGAAGTACA AAAAAGTCCG ATTTATGGCA
      TACACAGATG
1301  AAACCTTTAA GACTCGTGAA GCTATTCAGC ATGAATCAGG
      AATCTTGGGA
1351  CCTTTACTTT ATGGGGAAGT TGGAGACACA CTGTTGATTA
      TATTTAAGAA
1401  TCAAGCAAGC AGACCATATA ACATCTACCC TCACGGAATC
      ACTGATGTCC
1451  GTCCTTTGTA TTCAAGGAGA TTACCAAAAG GTGTAAAACA
      TTTGAAGGAT
1501  TTTCCAATTC TGCCAGGAGA AATATTCAAA TATAAATGGA
      CAGTGACTGT
1551  AGAAGATGGG CCAACTAAAT CAGATCCTCG GTGCCTGACC
      CGCTATTACT
1601  CTAGTTTCGT TAATATGGAG AGAGATCTAG CTTCAGGACT
      CATTGGCCCT
1651  CTCCTCATCT GCTACAAAGA ATCTGTAGAT CAAAGAGGAA
      ACCAGATAAT
1701  GTCAGACAAG AGGAATGTCA TCCTGTTTTC TGTATTTGAT
      GAGAACCGAA
1751  GCTGGTACCT CACAGAGAAT ATACAACGCT TTCTCCCCAA
      TCCAGCTGGA
1801  GTGCAGCTTG AGGATCCAGA GTTCCAAGCC TCCAACATCA
      TGCACAGCAT
1851  CAATGGCTAT GTTTTTGATA GTTTGCAGTT GTCAGTTTGT
      TTGCATGAGG
1901  TGGCATACTG GTACATTCTA AGCATTGGAG CACAGACTGA
      CTTCCTTTCT
1951  GTCTTCTTCT CTGGATATAC CTTCAAACAC AAAATGGTCT
      ATGAAGACAC
2001  ACTCACCCTA TTCCCATTCT CAGGAGAAAC TGTCTTCATG
      TCGATGGAAA
2051  ACCCAGGTCT ATGGATTCTG GGGTGCCACA ACTCAGACTT
      TCGGAACAGA
2101  GGCATGACCG CCTTACTGAA GGTTTCTAGT TGTGACAAGA
      ACACTGGTGA
2151  TTATTACGAG GACAGTTATG AAGATATTTC AGCATACTTG
      CTGAGTAAAA
2201  ACAATGCCAT TGAACCAAGA AGCTTCTCCC AGAATTCAAG
      ACACCCTAGC
2251  ACTAGGCAAA AGCAATTTAA TGCCACCACA ATTCCAGAAA
      ATGACATAGA
2301  GAAGACTGAC CCTTGGTTTG CACACAGAAC ACCTATGCCT
      AAAATACAAA
2351  ATGTCTCCTC TAGTGATTTG TTGATGCTCT TGCGACAGAG
      TCCTACTCCA
2401  CATGGGCTAT CCTTATCTGA TCTCCAAGAA GCCAAATATG
      AGACTTTTTC
2451  TGATGATCCA TCACCTGGAG CAATAGACAG TAATAACAGC
      CTGTCTGAAA
2501  TGACACACTT CAGGCCACAG CTCCATCACA GTGGGGACAT
      GGTATTTACC
2551  CCTGAGTCAG GCCTCCAATT AAGATTAAAT GAGAAACTGG
      GGACAACTGC
2601  AGCAACAGAG TTGAAGAAAC TTGATTTCAA AGTTTCTAGT
      ACATCAAATA
2651  ATCTGATTTC AACAATTCCA TCAGACAATT TGGCAGCAGG
      TACTGATAAT
2701  ACAAGTTCCT TAGGACCCCC AAGTATGCCA GTTCATTATG
      ATAGTCAATT
2751  AGATACCACT CTATTTGGCA AAAAGTCATC TCCCCTTACT
      GAGTCTGGTG
2801  GACCTCTGAG CTTGAGTGAA GAAAATAATG ATTCAAAGTT
      GTTAGAATCA
2851  GGTTTAATGA ATAGCCAAGA AAGTTCATGG GGAAAAAATG
      TATCGTCAAC
2901  AGAGAGTGGT AGGTTATTTA AAGGGAAAAG AGCTCATGGA
      CCTGCTTTGT
2951  TGACTAAAGA TAATGCCTTA TTCAAAGTTA GCATCTCTTT
      GTTAAAGACA
3001  AACAAAACTT CCAATAATTC AGCAACTAAT AGAAAGACTC
      ACATTGATGG
3051  CCCATCATTA TTAATTGAGA ATAGTCCATC AGTCTGGCAA
      AATATATTAG
3101  AAAGTGACAC TGAGTTTAAA AAAGTGACAC CTTTGATTCA
      TGACAGAATG
3151  CTTATGGACA AAAATGCTAC AGCTTTGAGG CTAAATCATA
      TGTCAAATAA
3201  AACTACTTCA TCAAAAAACA TGGAAATGGT CCAACAGAAA
      AAAGAGGGCC
3251  CCATTCCACC AGATGCACAA AATCCAGATA TGTCGTTCTT
      TAAGATGCTA
3301  TTCTTGCCAG AATCAGCAAG GTGGATACAA AGGACTCATG
      GAAAGAACTC
3351  TCTGAACTCT GGGCAAGGCC CCAGTCCAAA GCAATTAGTA
      TCCTTAGGAC
3401  CAGAAAAATC TGTGGAAGGT CAGAATTTCT TGTCTGAGAA
      AAACAAAGTG
3451  GTAGTAGGAA AGGGTGAATT TACAAAGGAC GTAGGACTCA
      AAGAGATGGT
```

```
3501  TTTTCCAAGC AGCAGAAACC TATTTCTTAC TAACTTGGAT
      AATTTACATG

3551  AAAATAATAC ACACAATCAA GAAAAAAAAA TTCAGGAAGA
      AATAGAAAAG

3601  AAGGAAACAT TAATCCAAGA GAATGTAGTT TTGCCTCAGA
      TACATACAGT

3651  GACTGGCACT AAGAATTTCA TGAAGAACCT TTTCTTACTG
      AGCACTAGGC

3701  AAAATGTAGA AGGTTCATAT GACGGGCAT ATGCTCCAGT
      ACTTCAAGAT

3751  TTTAGGTCAT TAAATGATTC AACAAATAGA ACAAGAAAC
      ACACAGCTCA

3801  TTTCTCAAAA AAAGGGGAGG AAGAAAACTT GGAAGGCTTG
      GGAAATCAAA

3851  CCAAGCAAAT TGTAGAGAAA TATGCATGCA CCACAAGGAT
      ATCTCCTAAT

3901  ACAAGCCAGC AGAATTTTGT CACGCAACGT AGTAAGAGAG
      CTTTGAAACA

3951  ATTCAGACTC CCACTAGAAG AAACAGAACT TGAAAAAAGG
      ATAATTGTGG

4001  ATGACACCTC AACCCAGTGG TCCAAAAACA TGAAACATTT
      GACCCCGAGC

4051  ACCCTCACAC AGATAGACTA CAATGAGAAG GAGAAAGGGG
      CCATTACTCA

4101  GTCTCCCTTA TCAGATTGCC TTACGAGGAG TCATAGCATC
      CCTCAAGCAA

4151  ATAGATCTCC ATTACCCATT GCAAAGGTAT CATCATTTCC
      ATCTATTAGA

4201  CCTATATATC TGACCAGGGT CCTATTCCAA GACAACTCTT
      CTCATCTTCC

4251  AGCAGCATCT TATAGAAAGA AAGATTCTGG GGTCCAAGAA
      AGCAGTCATT

4301  TCTTACAAGG AGCCAAAAAA AATAACCTTT CTTTAGCCAT
      TCTAACCTTG

4351  GAGATGACTG GTGATCAAAG AGAGGTTGGC TCCCTGGGGA
      CAAGTGCCAC

4401  AAATTCAGTC ACATACAAGA AAGTTGAGAA CACTGTTCTC
      CCGAAACCAG

4451  ACTTGCCCAA AACATCTGGC AAAGTTGAAT TGCTTCCAAA
      AGTTCACATT

4501  TATCAGAAGG ACCTATTCCC TACGGAAACT AGCAATGGGT
      CTCCTGGCCA

4551  TCTGGATCTC GTGGAAGGGA GCCTTCTTCA GGGAACAGAG
      GGAGCGATTA

4601  AGTGGAATGA AGCAAACAGA CCTGGAAAAG TTCCCTTTCT
      GAGAGTAGCA

4651  ACAGAAAGCT CTGCAAAGAC TCCCTCCAAG CTATTGGATC
      CTCTTGCTTG

4701  GGATAACCAC TATGGTACTC AGATACCAAA AGAAGAGTGG
      AAATCCCAAG

4751  AGAAGTCACC AGAAAAAACA GCTTTTAAGA AAAAGGATAC
      CATTTTGTCC

4801  CTGAACGCTT GTGAAAGCAA TCATGCAATA GCAGCAATAA
      ATGAGGGACA

4851  AAATAAGCCC GAAATAGAAG TCACCTGGGC AAAGCAAGGT
      AGGACTGAAA

4901  GGCTGTGCTC TCAAAACCCA CCAGTCTTGA AACGCCATCA
      ACGGGAAATA

4951  ACTCGTACTA CTCTTCAGTC AGATCAAGAG GAAATTGACT
      ATGATGATAC

5001  CATATCAGTT GAAATGAAGA AGGAAGATTT TGACATTTAT
      GATGAGGATG

5051  AAAATCAGAG CCCCCGCAGC TTTCAAAAGA AAACACGACA
      CTATTTTATT

5101  GCTGCAGTGG AGAGGCTCTG GGATTATGGG ATGAGTAGCT
      CCCCACATGT

5151  TCTAAGAAAC AGGGCTCAGA GTGGCAGTGT CCCTCAGTTC
      AAGAAAGTTG

5201  TTTTCCAGGA ATTTACTGAT GGCTCCTTTA CTCAGCCCTT
      ATACCGTGGA

5251  GAACTAAATG AACATTTGGG ACTCCTGGGG CCATATATAA
      GAGCAGAAGT

5301  TGAAGATAAT ATCATGGTAA CTTTCAGAAA TCAGGCCTCT
      CGTCCCTATT

5351  CCTTCTATTC TAGCCTTATT TCTTATGAGG AAGATCAGAG
      GCAAGGAGCA

5401  GAACCTAGAA AAAACTTTGT CAAGCCTAAT GAAACCAAAA
      CTTACTTTTG

5451  GAAAGTGCAA CATCATATGG CACCCACTAA AGATGAGTTT
      GACTGCAAAG

5501  CCTGGGCTTA TTTCTCTGAT GTTGACCTGG AAAAAGATGT
      GCACTCAGGC

5551  CTGATTGGAC CCCTTCTGGT CTGCCACACT AACACACTGA
      ACCCTGCTCA

5601  TGGGAGACAA GTGACAGTAC AGGAATTTGC TCTGTTTTTC
      ACCATCTTTG

5651  ATGAGACCAA AAGCTGGTAC TTCACTGAAA ATATGGAAAG
      AAACTGCAGG

5701  GCTCCCTGCA ATATCCAGAT GGAAGATCCC ACTTTTAAAG
      AGAATTATCG

5751  CTTCCATGCA ATCAATGGCT ACATAATGGA TACACTACCT
      GGCTTAGTAA

5801  TGGCTCAGGA TCAAAGGATT CGATGGTATC TGCTCAGCAT
      GGGCAGCAAT

5851  GAAAACATCC ATTCTATTCA TTTCAGTGGA CATGTGTTCA
      CTGTACGAAA

5901  AAAAGAGGAG TATAAAATGG CACTGTACAA TCTCTATCCA
      GGTGTTTTTG

5951  AGACAGTGGA AATGTTACCA TCCAAAGCTG GAATTTGGCG
      GGTGGAATGC

6001  CTTATTGGCG AGCATCTACA TGCTGGGATG AGCACACTTT
      TTCTGGTGTA

6051  CAGCAATAAG TGTCAGACTC CCCTGGGAAT GGCTTCTGGA
      CACATTAGAG

6101  ATTTTCAGAT TACAGCTTCA GGACAATATG GACAGTGGGC
      CCCAAAGCTG

6151  GCCAGACTTC ATTATTCCGG ATCAATCAAT GCCTGGAGCA
      CCAAGGAGCC
```

```
6201 CTTTTCTTGG ATCAAGGTGG ATCTGTTGGC ACCAATGATT
     ATTCACGGCA

6251 TCAAGACCCA GGGTGCCCGT CAGAAGTTCT CCAGCCTCTA
     CATCTCTCAG

6301 TTTATCATCA TGTATAGTCT TGATGGGAAG AAGTGGCAGA
     CTTATCGAGG

6351 AAATTCCACT GGAACCTTAA TGGTCTTCTT TGGCAATGTG
     GATTCATCTG

6401 GGATAAAACA CAATATTTTT AACCCTCCAA TTATTGCTCG
     ATACATCCGT

6451 TTGCACCCAA CTCATTATAG CATTCGCAGC ACTCTTCGCA
     TGGAGTTGAT

6501 GGGCTGTGAT TTAAATAGTT GCAGCATGCC ATTGGGAATG
     GAGAGTAAAG

6551 CAATATCAGA TGCACAGATT ACTGCTTCAT CCTACTTTAC
     CAATATGTTT

6601 GCCACCTGGT CTCCTTCAAA AGCTCGACTT CACCTCCAAG
     GGAGGAGTAA

6651 TGCCTGGAGA CCTCAGGTGA ATAATCCAAA AGAGTGGCTG
     CAAGTGGACT

6701 TCCAGAAGAC AATGAAAGTC ACAGGAGTAA CTACTCAGGG
     AGTAAAATCT

6751 CTGCTTACCA GCATGTATGT GAAGGAGTTC CTCATCTCCA
     GCAGTCAAGA

6801 TGGCCATCAG TGGACTCTCT TTTTTCAGAA TGGCAAAGTA
     AAGGTTTTTC

6851 AGGGAAATCA AGACTCCTTC ACACCTGTGG TGAACTCTCT
     AGACCCACCG

6901 TTACTGACTC GCTACCTTCG AATTCACCCC CAGAGTTGGG
     TGCACCAGAT

6951 TGCCCTGAGG ATGGAGGTTC TGGGCTGCGA GGCACAGGAC
     CTCTACTGA
```

The wild-type human factor VIII encoded by SEQ ID NO: 1 has an amino acid sequence of SEQ ID NO: 2, as follows:

```
   1 ATRRYYLGAV ELSWDYMQSD LGELPVDARF PPRVPKSFPF
     NTSVVYKKTL

51 FVEFTVHLFN IAKPRPPWMG LLGPTIQAEV YDTVVITLKN
     MASHPVSLHA

101 VGVSYWKASE GAEYDDQTSQ REKEDDKVFP GGSHTYVWQV
     LKENGPMASD

151 PLCLTYSYLS HVDLVKDLNS GLIGALLVCR EGSLAKEKTQ
     TLHKFILLFA

201 VFDEGKSWHS ETKNSLMQDR DAASARAWPK MHTVNGYVNR
     SLPGLIGCHR

251 KSVYWHVIGM GTTPEVHSIF LEGHTFLVRN HRQASLEISP
     ITFLTAQTLL

301 MDLGQFLLFC HISSHQHDGM EAYVKVDSCP EEPQLRMKNN
     EEAEDYDDDL

351 TDSEMDVVRF DDDNSPSFIQ IRSVAKKHPK TWVHYIAAEE
     EDWDYAPLVL

401 APDDRSYKSQ YLNNGPQRIG RKYKKVRFMA YTDETFKTRE
     AIQHESGILG

451 PLLYGEVGDT LLIIFKNQAS RPYNIYPHGI TDVRPLYSRR
     LPKGVKHLKD

501 FPILPGEIFK YKWTVTVEDG PTKSDPRCLT RYYSSFVNME
     RDLASGLIGP

551 LLICYKESVD QRGNQIMSDK RNVILFSVFD ENRSWYLTEN
     IQRFLPNPAG

601 VQLEDPEFQA SNIMHSINGY VFDSLQLSVC LHEVAYWYIL
     SIGAQTDFLS

651 VFFSGYTFKH KMVYEDTLTL FPFSGETVFM SMENPGLWIL
     GCHNSDFRNR

701 GMTALLKVSS CDKNTGDYYE DSYEDISAYL LSKNNAIEPR
     SFSQNSRHPS

751 TRQKQFNATT IPENDIEKTD PWFAHRTPMP KIQNVSSSDL
     LMLLRQSPTP

801 HGLSLSDLQE AKYETFSDDP SPGAIDSNNS LSEMTHFRPQ
     LHHSGDMVFT

851 PESGLQLRLN EKLGTTAATE LKKLDFKVSS TSNNLISTIP
     SDNLAAGTDN

901 TSSLGPPSMP VHYDSQLDTT LFGKKSSPLT ESGGPLSLSE
     ENNDSKLLES

951 GLMNSQESSW GKNVSSTESG RLFKGKRAHG PALLTKDNAL
     FKVSISLLKT

1001 NKTSNNSATN RKTHIDGPSL LIENSPSVWQ NILESDTEFK
     KVTPLIHDRM

1051 LMDKNATALR LNHMSNKTTS SKNMEMVQQK KEGPIPPDAQ
     NPDMSFFKML

1101 FLPESARWIQ RTHGKNSLNS GQGPSPKQLV SLGPEKSVEG
     QNFLSEKNKV

1151 VVGKGEFTKD VGLKEMVFPS SRNLFLTNLD NLHENNTHNQ
     EKKIQEEIEK

1201 KETLIQENVV LPQIHTVTGT KNFMKNLFLL STRQNVEGSY
     EGAYAPVLQD

1251 FRSLNDSTNR TKKHTAHFSK KGEEENLEGL GNQTKQIVEK
     YACTTRISPN

1301 TSQQNFVTQR SKRALKQFRL PLEETELEKR IIVDDTSTQW
     SKNMKHLTPS

1351 TLTQIDYNEK EKGAITQSPL SDCLTRSHSI PQANRSPLPI
     AKVSSFPSIR

1401 PIYLTRVLFQ DNSSHLPAAS YRKKDSGVQE SSHFLQGAKK
     NNLSLAILTL

1451 EMTGDQREVG SLGTSATNSV TYKKVENTVL PKPDLPKTSG
     KVELLPKVHI

1501 YQKDLFPTET SNGSPGHLDL VEGSLLQGTE GAIKWNEANR
     PGKVPFLRVA

1551 TESSAKTPSK LLDPLAWDNH YGTQIPKEEW KSQEKSPEKT
     AFKKKDTILS

1601 LNACESNHAI AAINEGQNKP EIEVTWAKQG RTERLCSQNP
     PVLKRHQREI

1651 TRTTLQSDQE EIDYDDTISV EMKKEDFDIY DEDENQSPRS
     FQKKTRHYFI

1701 AAVERLWDYG MSSSPHVLRN RAQSGSVPQF KKVVFQEFTD
     GSFTQPLYRG

1751 ELNEHLGLLG PYIRAEVEDN IMVTFRNQAS RPYSFYSSLI
     SYEEDQRQGA
```

```
1801  EPRKNFVKPN  ETKTYFWKVQ  HHMAPTKDEF  DCKAWAYFSD
      VDLEKDVHSG

1851  LIGPLLVCHT  NTLNPAHGRQ  VTVQEFALFF  TIFDETKSWY
      FTENMERNCR

1901  APCNIQMEDP  TFKENYRFHA  INGYIMDTLP  GLVMAQDQRI
      RWYLLSMGSN

1951  ENIHSIHFSG  HVFTVRKKEE  YKMALYNLYP  GVFETVEMLP
      SKAGIWRVEC

2001  LIGEHLHAGM  STLFLVYSNK  CQTPLGMASG  HIRDFQITAS
      GQYGQWAPKL

2051  ARLHYSGSIN  AWSTKEPFSW  IKVDLLAPMI  IHGIKTQGAR
      QKFSSLYISQ

2101  FIIMYSLDGK  KWQTYRGNST  GTLMVFFGNV  DSSGIKHNIF
      NPPIIARYIR

2151  LHPTHYSIRS  TLRMELMGCD  LNSCSMPLGM  ESKAISDAQI
      TASSYFTNMF

2201  ATWSPSKARL  HLQGRSNAWR  PQVNNPKEWL  QVDFQKTMKV
      TGVTTQGVKS

2251  LLTSMYVKEF  LISSSQDGHQ  WTLFFQNGKV  KVFQGNQDSF
      TPVVNSLDPP

2301  LLTRYLRIHP  QSWVHQIALR  MEVLGCEAQD  LY
```

A first aspect of the present invention relates to a recombinant factor VIII that includes one or more mutations at an interface of A1 and C2 domains of the recombinant factor VIII. This mutation results in enhanced stability, particularly enhanced thermal and/or chemical stability, of factor VIII. The one or more mutations include substitution of one or more amino acid residues with an amino acid residue having a higher hydrophobicity, or substitution of two or more amino acid residues with Cysteine to afford a disulfide bond between the A1 and C2 domains.

As used herein, an amino acid having a higher hydrophobicity refers to a residue having a higher measurement or ranking of hydrophobicity relative to a particular wild type residue at the location of interest. The hydrophobic effect represents the tendency of water to exclude non-polar molecules. Hydropathy scale is a ranking list for the relative hydrophobicity of amino acid residues and proteins. The "hydropathy index" of a protein or amino acid is a number representing its hydrophilic or hydrophobic properties. Different methods have been used in the art to calculate the relative hydrophobicity of amino acid residues and proteins (Kyte et al., "A Simple Method for Displaying the Hydropathic Character of a Protein," *J. Mol. Biol.* 157: 105-32 (1982); Eisenberg D, "Three-dimensional Structure of Membrane and Surface Proteins," *Ann. Rev. Biochem.* 53: 595-623 (1984); Rose et al., "Hydrogen Bonding, Hydrophobicity, Packing, and Protein Folding," *Annu. Rev. Biomol. Struct.* 22: 381-415 (1993); Kauzmann, "Some Factors in the Interpretation of Protein Denaturation," *Adv. Protein Chem.* 14: 1-63 (1959), which are hereby incorporated by reference in their entirety). Any one of these hydrophobicity scales can be used for the purposes of the present invention; however, the Kyte-Doolittle hydrophobicity scale is perhaps the most often referenced scale. The hydropathy index is directly proportional to the hydrophobicity of the amino acid or the protein.

As used herein, the term "interface" is used to describe a protein surface where the atoms of the protein come in contact with the solvent (solvent-protein interface) or with another domain (domain interface). Domain interfaces can be either inter-domain (between domains) or intra-domain (within domains). Various methods are known in the art to identify interfaces. For example, the geometric distance between atoms that belong to same or different domains can be used to identify intra-domain or inter-domain interfaces (structural information, such as atomic coordinates, is available at the Protein Databank; Berman et al., "The Protein Data Bank," *Nucleic Acid Res* 28:235-242 (2000), which is hereby incorporated by reference in its entirety). Another approach is the Accessible Surface Area (ASA), which detects the buried region of a protein that is detached from a solvent (Jones et al., "Analysis of Protein-protein Interaction Sites Using Surface Patches," *J Mol Biol* 272:121-132 (1997), which is hereby incorporated by reference in its entirety). A further approach is the Voronoi diagram, a computational geometry method that uses a mathematical definition of interface regions (Ban et al., "Interface Surfaces for Protein-protein Complexes," *Proceedings of the Research in Computational Molecular Biology*, San Diego 27-31 (2004); Poupon A, "Voronoi and Voronoi-Related Tessellations in Studies of Protein Structure and Interaction," *Curr Opin Struct Biol* 14:233-241 (2004); Kim et al., "Euclidean Voronoi Diagrams of 3D Spheres and Applications to Protein Structure Analysis," *Japan Journal of Industrial and Applied Mathematics* 2005, 22:251-265 (2005), which are hereby incorporated by reference in their entirety). As described herein, the factor VIII crystal structure (Shen et al., "The Tertiary Structure and Domain Organization of Coagulation Factor VIII," *Blood* 111:1240-1247 (2008); Ngo et al., "Crystal Structure of Human Factor VIII: Implications for the Formation of the Factor IXa:Factor VIIIa Complex," *Structure* 16:597-606 (2008), which is hereby incorporated by reference in its entirety) can be modeled using Swiss PDB Viewer to identify residues that upon substitution with Cysteine will allow for disulfide bond formation (see FIG. 3B) or residues that are suitable for substitution with an amino acid having higher hydrophobicity (see FIG. 3C).

As used herein, a region of the A1 domain that interfaces with the C2 domain is referred to as a "C2 domain interface" and a region of the C2 domain that interfaces with the A1 domain is referred to as an "A1 domain interface."

The wild type (WT) factor VIII can be such that the A1 domain of the WT factor VIII includes a C2 domain interface having the amino acid sequence of (i) KXS (aa 8-10 of SEQ ID NO: 10) where "X" is A or S; (ii) SXXE (aa 20-23 of SEQ ID NO: 10) where "X" at the $2^{nd}$ position can be Q, K, or P, and "X" at the $3^{rd}$ position can be R, K, M, T, or A; and/or (iii) TYXW (aa 36-39 of SEQ ID NO: 10), where "X" at the $3^{rd}$ position can be V or A. These are illustrated in FIG. 1.

The WT factor VIII can be such that the C2 domain of the WT factor VIII includes an A1 domain interface having the amino acid sequence of (i) XVT (aa 9-11 of SEQ ID NO: 18), where "X" is K or R; (ii) PPXX (aa 68-71 of SEQ ID NO: 18), where "X" at the $3^{rd}$ position is L or R, and "X" at the $4^{th}$ position is L, F, or V; and/or (iii) XXQX (aa 96-99 of SEQ ID NO: 18), where the "X" at the $1^{st}$ position is E or D, "X" at the $2^{nd}$ position is A or T, and "X" at the $4^{th}$ position is D or Q. These are illustrated in FIG. 2.

According to one embodiment, one or both of the A1 domain interface and C2 domain interface include a substitution to introduce a Cysteine residue. In preferred embodiments, the substitution of amino acid residues at the interface of A1 and C2 domains is carried out such that at least a pair of amino acids are substituted with Cysteine. In this embodiment, the pair of Cysteine residues form an inter-domain (A1 to C2 domain) disulfide bond such that the stability of the recombinant factor VIII is enhanced.

In another embodiment of the recombinant factor VIII of the present invention, the one or more mutations at the interface of A1 and C2 domains of the recombinant factor VIII is the replacement of one or more amino acid residues with an amino acid incapable of forming disulfide bonds but having a higher hydrophobicity index.

In a further embodiment, multiple mutations are introduced at several interfaces of the A1 and C2 domains of factor VIII, including: (i) a pair of substitutions to introduce a pair of Cysteine residues that are capable of forming an inter-domain (A1 to C2 domain) disulfide bond; and (ii) the replacement of one or more amino acid residues with an amino acid incapable of forming disulfide bonds but having a higher hydrophobicity index.

The recombinant factor VIII according to several embodiments of the present invention are characterized by an A1 domain that includes a C2 domain interface having the amino acid sequence of (i) KXS (SEQ ID NO: 19), where "X" is T, G, A, M, C, F, L, V, or I; (ii) SXXX (SEQ ID NO: 20), where "X" at the $2^{nd}$ position is wild type (Q, K, or P) or E, D, N, H, Y, W, S, T, G, A, M, C, F, L, V, or I, "X" at the $3^{th}$ position can be any amino acid other than R or preferably any amino acid other than R, K, M, T, or A; and "X" at the $4^{th}$ position is wild type (E) or Q, D, N, H, P, Y, W, S, T, G, A, M, C, F, L, V, or I; and/or (iii) TYXW (SEQ ID NO: 21), where "X" is M, C, F, L, V, or I. In at least one of the C2 domain interfaces, one of the X residues represents a substitution of a wild type residue.

The recombinant factor VIII according to several embodiments of the present invention are characterized by a C2 domain that includes an A1 domain interface having the amino acid sequence of (i) XVT (SEQ ID NO: 22), where "X" can be any amino acid other than K or R; (ii) PPXX (SEQ ID NO: 23), where "X" at the $3^{rd}$ position can be any amino acid besides L or R and "X" at the $4^{th}$ position is L, V, or I; and/or (iii) XXQX (SEQ ID NO: 24), where "X" at the $1^{st}$ position is wild type (E or D) or Q, N, H, P, Y, W, S, T, G, A, M, C, F, L, V, or I, "X" at the $2^{nd}$ position is wild type (A or T) or G, M, C, F, L, V, or I, and "X" at the $4^{th}$ position is wild type (D or Q) or N, H, P, Y, W, S, T, G, A, M, C, F, L, V, or I. In at least one of the A1 domain interfaces, one of the X residues represents a substitution of a wild type residue.

In certain embodiments, where a disulfide linkage is formed between A1 and C2 domains using a cysteine substitution, the cysteine substitution occurs at residue 121 of human factor VIII (i.e., the C2 domain interface is SEQ ID NO: 20, where X at the third position is cysteine) and residue 2302 of human factor VIII (i.e., the A1 domain interface is SEQ ID NO: 23, where X at the fourth position is cysteine). In other embodiments, the cysteine substitution occurs at a residue other than residues 121 and 2302 of human factor VIII.

One embodiment of the recombinant factor VIII of the present invention includes an A1 domain having a C2 domain interface that includes the amino acid sequence KXS (SEQ ID NO: 19), where the second residue (corresponding to position 108 of SEQ ID NO: 2) is Valine, Isoleucine, or Leucine.

A further embodiment of the recombinant factor VIII of the present invention includes a C2 domain having an A1 domain interface that includes the amino acid sequence of XVT (SEQ ID NO: 22), where X (corresponding to position 2328 of SEQ ID NO: 2) is other than Lysine or Arginine.

Another embodiment of the recombinant factor VIII includes an A1 domain having a C2 domain interface that includes the amino acid sequence of SXXE (SEQ ID NO: 25), where the second residue can be Q, K, P, E, D, N, H, Y, W, S, T, G, A, M, C, F, L, V, or I and the third residue (corresponding to position 121 of SEQ ID NO: 2) is cysteine; and a C2 domain having an A1 domain interface that includes the amino acid sequence of PPXX (SEQ ID NO: 23), where X at the $3^{th}$ position is any amino acid besides L or R, and X at the $4^{th}$ position (corresponding to position 2302 of SEQ ID NO: 2) is cysteine.

Yet another embodiment of the recombinant factor includes a C2 domain having an A1 domain interface that includes the amino acid sequence of XXQX (SEQ ID NO: 24), where the $1^{st}$ residue is E, D, Q, N, H, P, Y, W, S, T, G, A, M, C, F, L, V, or I; the $2^{nd}$ residue (corresponding to position 2328 of SEQ ID NO: 2) is Valine, Isoleucine, or Leucine; and the $4^{th}$ residue is D, Q, N, H, P, Y, W, S, T, G, A, M, C, F, L, V, or I.

The recombinant factor VIII according to the present invention can also have more than one mutation as described supra. In one preferred embodiment the recombinant factor VIII has two or more amino acid substitutions.

According to one embodiment, the recombinant factor VIII includes (i) an A1 domain having a C2 domain interface that includes the amino acid sequence of KXS (SEQ ID NO: 19), where X (corresponding to position 108 of SEQ ID NO: 2) is Isoleucine, Leucine, or Valine; and (ii) a C2 domain having an A1 domain interface that includes the amino acid sequence XXQX (SEQ ID NO: 24), where the $1^{st}$ and $4^{th}$ residues are as described above and the $2^{nd}$ residue (corresponding to position 2328 of SEQ ID NO: 2) is Isoleucine, Leucine, or Valine.

Suitable mutant factor VIII sequences that can be modified in accordance with the present invention can also include any previously known or subsequently identified mutant factor VIII sequences that have modified properties with regard to various attributes, including, without limitation, antigenicity, circulating half-life, factor VIIIa stability, protein secretion, affinity for factor IXa and/or factor X, altered factor VIII-inactivation cleavage sites, altered activated Protein C cleavage sites, enhanced specific activity of factor VIIIa, immunogenicity, and shelf-life.

In one embodiment the recombinant factor VIII of the present invention further comprises one or more of (i) factor IXa and/or factor X binding domains modified to enhance the affinity of the recombinant factor VIII for one or both of factor IXa and factor X; (ii) modified sites that enhance secretion in culture; (iii) modified serum protein binding sites that enhance the circulating half-life thereof; (iv) at least one glycosylation recognition sequence that is effective in decreasing antigenicity and/or immunogenicity thereof; (v) a modified A1 domain calcium-binding site that improves specific activity of the recombinant factor VIIIa; (vi) modified activated protein C-cleavage site; (vii) a modified A1 and A2 domain interface to enhance factor VIIIa stability; and (viii) a modified A2 and A3 domain interface to enhance factor VIIIa stability.

The recombinant factor VIII of the present invention can be one that has a combination of mutations, including one or more mutations at an interface of A1 and C2 domains of recombinant factor VIII as described supra and one or more mutations at the A1 and A2 domain interface and/or the A2 and A3 domain interface. Such a recombinant factor VIII in addition to the one or more mutations at the A1 and C2 domain interface also includes substitution of one or more charged amino acid residues with a hydrophobic amino acid residue at either or both of the A1 and A2 or A2 and A3 domain interfaces.

Preferably, the charged residue to be replaced is either a Glu or Asp residue that does not participate in hydrogen bonding between the A1 and A2 or A2 and A3 domains. The hydrophobic amino acid residue that replaces the charged residue can be any of Ala, Val, Ile, Leu, Met, Phe, or Trp. Particularly preferred recombinant factor VIII of the present invention includes a substitution of the residue corresponding to Glu287 of wild type factor VIII, a substitution of the residue corresponding to Asp302 of wild type factor VIII, a substitution of the residue corresponding to Asp519 of wild type factor VIII, a substitution of the residue corresponding to Glu665 of wild type factor VIII, a substitution of the residue corresponding to Glu1984 of wild type factor VIII, or combinations thereof. The D302A, E287A, E665A, E665V, D519A, D519V, E1984A, and E1984V substitutions are preferred for achieving a recombinant factor VIII that has enhanced stability of both factor VIII and factor VIIIa. Preferred combinations of these substitutions include, without limitation, those corresponding to D519AE665V, D519VE665V, and D519VE1984A mutants, as well as D519AE665VE1984A and D519VE665VE1984A mutants. The enhanced stability of these mutants is believed to be achieved by stabilizing the inter-domain interface in factor VIII as well as reducing A2 subunit dissociation from A1/A3C1C2 as compared to wild type factor VIIIa. Exemplary mutants of this type are described in U.S. Patent Application Publ. No. US2009/0118184 to Fay et al., which is hereby incorporated by reference in its entirety.

Examples of mutant factor VIII possessing substitutions at the A1-C2 domain interface as well as one or both of the A1-A2 and A2-A3 domain interfaces include, without limitation, A108ID519AE665V, A108ID519VE665V, A108ID519VE1984A, A108ID519AE665VE1984A, A108ID519VE665VE1984A, R121C-L2302C/D519AE665V, R121C-L2302C/D519VE665V, R121C-L2302C/D519VE1984A, R121C-L2302C/D519AE665VE1984A, and R121C-L2302C/D519VE665VE1984A. Each of these mutant factor VIII can be expressed in a B-domainless form, as described below.

Another example of a suitable mutant factor VIII that can be modified in accordance with the present invention is a factor VIII having a modified calcium binding site, preferably at an amino acid corresponding to residue 113 of SEQ ID NO: 2. This affords a factor VIIIa having enhanced specific activity. Exemplary mutants of this type are described in U.S. Patent Application Publ. No. US2007/0265199 to Fay et al., which is hereby incorporated by reference in its entirety. Preferably, the residue 113 mutant also is modified in accordance with one or more of the mutations described above (e.g., at positions 287, 302, 519, 665, and/or 1984) to afford a high stability/high specific activity factor VIII protein. Exemplary high stability/high specific activity factor VIII proteins include, without limitation: those possessing combined substitutions E113AD519A, E113AD519V, E113AE665A, E113AE665V, E113AE1984V, E113AD519AE665V, E113AD519VE665V, E113AD519VE1984A, E113AD519AE665VE1984A, and E113AD519VE665VE1984A.

Examples of mutant factor VIII possessing substitutions at the A1-C2 domain interface as well as the residue 113 substitution, and one or both of the A1-A2 and A2-A3 domain interface substitutions include, without limitation, A108IE113AD519AE665V, A108IE113AD519VE665V, A108IE113AD519VE1984A, A108IE113AD519AE665VE1984A, A108IE113AD519VE665VE1984A, R121C-L2302C/E113AD519AE665V, R121C-L2302C/E113AD519VE665V, R121C-L2302C/E113AD519VE1984A, R121C-L2302C/E113AD519AE665VE1984A, and R121C-L2302C/E113AD519VE665VE1984A. Each of these mutant factor VIII can be expressed in a B-domainless form, as described below.

A third example of a suitable mutant factor VIII that can be modified in accordance with the present invention is a B-domainless factor VIII that contains amino acid residues 1-740 and 1690-2332 of SEQ ID NO: 2 (see, e.g., U.S. Pat. No. 6,458,563 to Lollar, which is hereby incorporated by reference in its entirety).

In one embodiment of the B-domainless recombinant factor VIII of the present invention, the B-domain is replaced by a DNA linker segment and at least one codon is replaced with a codon encoding an amino acid residue that has the same charge as a corresponding residue of porcine factor VIII (see, e.g., U.S. Patent Application Publication No. 2004/0197875 to Hauser et al., which is hereby incorporated by reference in its entirety).

In another embodiment of the B-domainless recombinant factor VIII of the present invention, the modified mutant factor VIII is encoded by a nucleotide sequence having a truncated factor IX intron 1 inserted in one or more locations (see, e.g., U.S. Pat. No. 6,800,461 to Negrier and U.S. Pat. No. 6,780,614 to Negrier, each of which is hereby incorporated by reference in its entirety). This recombinant factor VIII can be used for yielding higher production of the recombinant factor VIII in vitro as well as in a transfer vector for gene therapy (see, e.g., U.S. Pat. No. 6,800,461 to Negrier, which is hereby incorporated by reference in its entirety). In a particular example of this embodiment, the recombinant factor VIII can be encoded by a nucleotide sequence having a truncated factor IX intron 1 inserted in two locations, and having a promoter that is suitable for driving expression in hematopoietic cell lines, and specifically in platelets (see, e.g., U.S. Pat. No. 6,780,614 to Negrier, which is hereby incorporated by reference in its entirety).

Regardless of the embodiment, the B-domainless factor VIII preferably contains one or more of the mutations described above (e.g., modified A1 domain interface and/or C2 domain interface, as well as any other mutations to affect other properties of the resulting factor VIII). Recombinant factor VIII proteins prepared in accordance with the Examples herein are B-domainless.

A fourth example of a suitable mutant factor VIII that can be modified in accordance with the present invention is a chimeric human/animal factor VIII that contains one or more domains, or portions thereof, from human factor VIII and one or more domains, or portions thereof, from a non-human mammalian factor VIII. One or more animal amino acid residues can be substituted for human amino acid residues that are responsible for the antigenicity of human factor VIII. In particular, animal (e.g., porcine) residue substitutions can include, without limitation, one or more of the following: R484A, R488G, P485A, L486S, Y487L, Y487A, S488A, S488L, R489A, R489S, R490G, L491S, P492L, P492A, K493A, G494S, V495A, K496M, H497L, L498S, K499M, D500A, F501A, P502L, I503M, L504M, P505A, G506A, E507G, I508M, I508A, M2199I, F2200L, L2252F, V2223A, K2227E, and/or L2251 (U.S. Pat. No. 5,859,204 to Lollar, U.S. Pat. No. 6,770,744 to Lollar, and U.S. Patent Application Publication No. 2003/0166536 to Lollar, each of which is hereby incorporated by reference in its entirety). Preferably, the recombinant chimeric factor VIII contains one or more of the mutations described above (e.g., modified A1 domain interface and/or C2 domain interface).

A fifth example of a suitable mutant factor VIII that can be modified in accordance with the present invention is a factor VIII that has enhanced affinity for factor IXa (see, e.g., Fay et al., "Factor VIIIa A2 Subunit Residues 558-565 Represent a Factor IXa Interactive Site," *J. Biol. Chem.* 269(32):20522-7 (1994); Bajaj et al., "Factor IXa: Factor VIIIa Interaction.

Helix 330-338 of Factor IXa Interacts with Residues 558-565 and Spatially Adjacent Regions of the A2 Subunit of Factor VIIIa," *J. Biol. Chem.* 276(19):16302-9 (2001); and Lenting et al., "The Sequence Glu1811-Lys1818 of Human Blood Coagulation Factor VIII Comprises a Binding Site for Activated Factor IX," *J. Biol. Chem.* 271(4):1935-40 (1996), each of which is hereby incorporated by reference in its entirety) and/or factor X (see, e.g., Lapan et al., "Localization of a Factor X Interactive Site in the A1 Subunit of Factor VIIIa," *J. Biol. Chem.* 272:2082-88 (1997), which is hereby incorporated by reference in its entirety). Preferably, the enhanced-affinity factor VIII contains one or more of the mutations described above (e.g., modified A1 domain interface and/or C2 domain interface).

A sixth example of a suitable mutant factor VIII that can be modified in accordance with the present invention is a factor VIII that is modified to enhance secretion of the factor VIII (see, e.g., Swaroop et al., "Mutagenesis of a Potential Immunoglobulin-Binding Protein-Binding Site Enhances Secretion of Coagulation Factor VIII," *J. Biol. Chem.* 272(39): 24121-4 (1997), which is hereby incorporated by reference in its entirety). Preferably, the secretion enhanced mutant factor VIII contains one or more of the mutations identified above (e.g., modified A1 domain interface and/or C2 domain interface).

A seventh example of a suitable mutant factor VIII that can be modified in accordance with the present invention is a factor VIII with an increased circulating half-life. This modification can be made using various approaches, including, without limitation, by reducing interactions with heparan sulfate (Sarafanov et al., "Cell Surface Heparan Sulfate Proteoglycans Participate in Factor VIII Catabolism Mediated by Low Density Lipoprotein Receptor-Related Protein," *J. Biol. Chem.* 276(15):11970-9 (2001), which is hereby incorporated by reference in its entirety) and/or low-density lipoprotein receptor-related protein ("LRP") (Saenko et al., "Role of the Low Density Lipoprotein-Related Protein Receptor in Mediation of Factor VIII Catabolism," *J. Biol. Chem.* 274 (53):37685-92 (1999); and Lenting et al., "The Light Chain of Factor VIII Comprises a Binding Site for Low Density Lipoprotein Receptor-Related Protein," *J. Biol. Chem.* 274(34): 23734-9 (1999), each of which is hereby incorporated by reference in its entirety). Preferably, the half-life enhanced mutant factor VIII contains one or more of the mutations described above (e.g., modified A1 domain interface and/or C2 domain interface).

An eighth example of a suitable mutant factor VIII that can be modified in accordance with the present invention is a modified factor VIII encoded by a nucleotide sequence modified to code for amino acids within known, existing epitopes to produce a recognition sequence for glycosylation at asparagines residues (see, e.g., U.S. Pat. No. 6,759,216 to Lollar, which is hereby incorporated by reference in its entirety). The mutant factor VIII of this example can be useful in providing a modified factor VIII that escapes detection by existing inhibitory antibodies (low antigenicity factor VIII) and which decreases the likelihood of developing inhibitory antibodies (low immunogenicity factor VIII). In one particular embodiment of this example, the modified factor VIII is mutated to have a consensus amino acid sequence for N-linked glycosylation. An example of such a consensus sequence is N-X-S/T, where N is asparagine, X is any amino acid, and S/T stands for serine or threonine (see U.S. Pat. No. 6,759,216 to Lollar, which is hereby incorporated by reference in its entirety). Preferably, the glycosylation site-modified factor VIII contains one or more of the mutations identified above (e.g., modified A1 domain interface and/or C2 domain interface).

A ninth example of a suitable mutant factor VIII that can be modified in accordance with the present invention is a modified factor VIII that is a procoagulant-active factor VIII having various mutations (see, e.g., U.S. Patent Application Publication No. 2004/0092442 to Kaufman et al., which is hereby incorporated by reference in its entirety). One example of this embodiment relates to a modified factor VIII that has been modified to (i) delete the von Willebrand factor binding site, (ii) add a mutation at Arg 740, and (iii) add an amino acid sequence spacer between the A2- and A3-domains, where the amino acid spacer is of a sufficient length so that upon activation, the procoagulant-active factor VIII protein becomes a heterodimer (see U.S. Patent Application Publication No. 2004/0092442 to Kaufman et al., which is hereby incorporated by reference in its entirety). Preferably, procoagulant active factor VIII is also modified to contain one or more of the mutations described above (e.g., at positions modified A1 domain interface and/or C2 domain interface).

A tenth example of a suitable mutant factor VIII that can be modified in accordance with the present invention is a modified factor VIII that includes a substitution of one or more amino acid residues within a region surrounding an activated protein C cleavage site, except that the cleavable Arg scissile bond (at Arg336 and/or Arg562) is not substituted (see, e.g., U.S. Patent Application Publication No. 2009/0118185 to Fay et al., which is hereby incorporated by reference in its entirety). In the most preferred embodiments, the one or more substitutions appears within the P4-P3' activated protein C cleavage site, which can be the site corresponding to wild type residues 333-339 of the A1 domain or the site corresponding to residues 559-565 of the A2 domain. Exemplary mutant P4-P3' regions, which include the substitution of one or more amino acids include, without limitation, VDQRGNQ (SEQ ID NO: 26) neighboring Arg562, VDQRMKN (SEQ ID NO: 27) neighboring Arg562, and PQLRGNQ (SEQ ID NO: 28) neighboring Arg336, PDLRMKN (SEQ ID NO: 29) neighboring Arg336, PQQRMKN (SEQ ID NO: 30) neighboring Arg336, PQRRMKN (SEQ ID NO: 31) neighboring Arg336, PQLRGKN (SEQ ID NO: 32) neighboring Arg336, PQLRMIN (SEQ ID NO: 33) neighboring Arg336, and PQLRMNN (SEQ ID NO: 34) neighboring Arg336. These substitutions are preferred for achieving a mutant factor VIIIa having a reduced rate of inactivation by activated protein C, but unlike mutants having single mutation replacements of the P1 Arg residue the resulting factor VIIIa is capable of being inactivated by activated protein C. Preferably, factor VIII having a modified activated protein C cleavage site is also modified to contain one or more of the mutations described above (e.g., at positions modified A1 domain interface and/or C2 domain interface).

Further, the mutant factor VIII can be modified to take advantage of various advancements regarding recombinant coagulation factors generally (see, e.g., Saenko et al., "The Future of Recombinant Coagulation Factors," *J. Thrombosis and Haemostasis* 1:922-930 (2003), which is hereby incorporated by reference in its entirety).

The recombinant factor VIII of the present invention can be modified at any residue to stabilize the A1/C2 domain interfaces (includes positions corresponding to 108, 121, 2302, 2328 of the WT factor VIII), as well as be modified at any charged residue that destabilizes the A1A2 or A2A3 domain interfaces (including positions 287, 302, 519, 665, or 1984), be modified to be B-domainless, to be chimeric, to have modified calcium binding sites that enhance factor VIIIa activity (e.g., at position 113), to have altered inactivation cleavage sites, to have enhanced factor IXa and/or factor X affinity, to have enhanced secretion, to have an increased circulating half-life, or to have mutant glycosylation sites; or to possess any one or more of such modifications in addition to the one or more modifications to charged residues, including a modified calcium-binding site that improves activity of the recombinant factor VIII. A number of exemplary B-domainless high stability recombinant factor VIII proteins are described in the Examples.

The recombinant factor VIII is preferably produced in a substantially pure form. In a particular embodiment, the substantially pure recombinant factor VIII is at least about 80% pure, more preferably at least 90% pure, most preferably at least 95% pure. A substantially pure recombinant factor VIII can be obtained by conventional techniques well known in the art. Typically, the substantially pure recombinant factor VIII is secreted into the growth medium of recombinant host cells. Alternatively, the substantially pure recombinant factor VIII is produced but not secreted into growth medium. In such cases, to isolate the substantially pure recombinant factor VIII, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the substantially pure recombinant factor VIII is subjected to gel filtration in an appropriately sized dextran or polyacrylamide column to separate the recombinant factor VIII. If necessary, a protein fraction (containing the substantially pure recombinant factor VIII) may be further purified by high performance liquid chromatography ("HPLC").

Another aspect of the present invention relates to an isolated nucleic acid molecule that encodes the recombinant factor VIII of the present invention. The isolated nucleic acid molecule encoding the recombinant factor VIII can be either RNA or DNA.

In another embodiment the isolated nucleic acid molecule can have a nucleotide sequence encoding a recombinant factor VIII according to the present invention which further comprises one or more of (i) factor IXa and/or factor X binding domains modified to enhance the affinity of the recombinant factor VIII for one or both of factor IXa and factor X; (ii) modified sites that enhance secretion in culture; (iii) modified serum protein binding sites that enhance the circulating half-life thereof; (iv) at least one glycosylation recognition sequence that is effective in decreasing antigenicity and/or immunogenicity thereof; (v) a modified calcium-binding site that improves specific activity of the recombinant factor VIIIa; (vi) modified activated protein C-cleavage site; (vii) a modified A1 and A2 domain interface; and (viii) a modified A2 and A3 domain interface.

In one embodiment, the isolated nucleic acid molecule can have a nucleotide sequence encoding a modified A1/A2 domain interface or A2/A3 domain interface (e.g., at positions corresponding to positions 287, 302, 519, 665, 1984 and/or 332-340 of SEQ ID NO: 2), as modified with one or more of the substitutions affecting the A1/C2 domain interfaces (e.g., SEQ ID NOS: 19-25).

In another embodiment, the isolated nucleic acid molecule can have a nucleotide sequence encoding a mutation at position 113 that enhances factor VIII specific activity, as modified with one or more of the substitutions affecting the A1/C2 domain interfaces (e.g., SEQ ID NOS: 19-25).

In another embodiment, the isolated nucleic acid molecule can have a nucleotide sequence encoding a B-domainless factor VIII of the type described above, as modified with one or more of the substitutions affecting the A1/C2 domain interfaces (e.g., SEQ ID NOS: 19-25).

In another embodiment, the isolated nucleic acid molecule can have a nucleotide sequence encoding a chimeric human/porcine of the type described above, as modified with one or more of the substitutions affecting the A1/C2 domain interfaces (e.g., SEQ ID NOS: 19-25).

In another embodiment, the isolated nucleic acid molecule can have a nucleotide sequence encoding a factor VIII whose inactivation sites have been modified as described above, as further modified with one or more of the substitutions affecting the A1/C2 domain interfaces (e.g., SEQ ID NOS: 19-25).

In yet another embodiment, the isolated nucleic acid molecule can have a nucleotide sequence encoding a factor VIII whose affinity for factor IXa and/or factor X has been enhanced, as further modified with one or more of the substitutions affecting the A1/C2 domain interfaces (e.g., SEQ ID NOS: 19-25).

In a still further embodiment, the isolated nucleic acid molecule can have a nucleotide sequence encoding a factor VIII whose affinity for various serum-binding proteins has been altered to increase its circulating half-life, as further modified with one or more of the substitutions affecting the A1/C2 domain interfaces (e.g., SEQ ID NOS: 19-25).

In a further embodiment, the isolated nucleic acid molecule can have a nucleotide sequence encoding a factor VIII that has increased secretion in culture, as further modified with one or more of the substitutions affecting the A1/C2 domain interfaces (e.g., SEQ ID NOS: 19-25).

In a further embodiment, the isolated nucleic acid molecule can have a nucleotide sequence encoding a factor VIII that possesses one or more non-naturally occurring glycosylation site, as further modified with one or more of the substitutions affecting the A1/C2 domain interfaces (e.g., SEQ ID NOS: 19-25).

In a still further embodiment, the isolated nucleic acid molecule can have a nucleotide sequence encoding a factor VIII that has a modified activated protein C cleavage site, as further modified with one or more of the substitutions affecting the A1/C2 domain interfaces (e.g., SEQ ID NOS: 19-25).

In yet another embodiment, the isolated nucleic acid molecule encodes a recombinant factor VIII that is modified at any one or more charged residues as described above and is also modified to possess any two or more of the following: modified to be B-domainless, modified to be chimeric, modified to have altered inactivation cleavage sites, modified to have enhanced factor IXa and/or factor X affinity, modified to have enhanced secretion, modified to have an increased circulating half-life, modified to possess one or more non-naturally occurring glycosylation site, modified within a calcium-binding site (e.g., at position 113) such that the specific activity of the recombinant factor VIII is improved, modified activated protein C-cleavage site, a modified A1 and A2 domain interface, and a modified A2 and A3 domain interface.

Another aspect of the present invention relates to a recombinant DNA expression system that includes an isolated DNA molecule of the present invention, which expression system encodes a recombinant factor VIII. In one embodiment, the DNA molecule is in sense orientation relative to a promoter.

A further aspect of the present invention relates to a host cell including an isolated nucleic acid molecule encoding the recombinant factor VIII of the present invention. In a particular embodiment, the host cell can contain the isolated nucleic acid molecule in DNA molecule form, either as a stable plasmid or as a stable insertion or integration into the host cell genome. In another embodiment, the host cell can contain a DNA molecule in an expression system. Suitable host cells can be, without limitation, animal cells (e.g., baby hamster kidney ("BHK") cells), bacterial cells (e.g., *E. coli*), insect cells (e.g., Sf9 cells), fungal cells, yeast cells (e.g., *Saccharomyces* or *Schizosaccharomyces*), plant cells (e.g., *Arabidopsis* or tobacco cells), or algal cells.

The recombinant DNA expression system and host cells can be produced using various recombinant techniques well-known in the art, as further discussed below.

The DNA molecule encoding the recombinant factor VIII of the present invention can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements for the transcription and translation of the inserted protein-coding sequences. Thus, one embodiment of the present invention provides a DNA construct containing the isolated nucleic acid of the present invention, which is operably linked to both a 5' promoter and a 3' regulatory region (i.e., transcription terminator) capable of affording transcription and expression of the encoded recombinant factor VIII of the present invention in host cells or host organisms.

With respect to the recombinant expression system of the present invention, an expression vector containing a DNA molecule encoding the recombinant factor VIII of the present invention can be made using common techniques in the art. The nucleic acid molecules of the present invention can be inserted into any of the many available expression vectors using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. The selection of a vector will depend on the preferred transformation technique and target host for transformation.

A variety of host-vector systems may be utilized to express the recombinant factor VIII-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, adeno-associated virus, etc.); insect cell systems infected with virus (e.g., baculovirus); and plant cells infected by bacteria (e.g., *Agrobacterium*). The expression elements of these vectors vary in their strength and specificities. Depending upon the host-vector system utilized, any one of a number of suitable transcription and translation elements can be used.

When recombinantly produced, the factor VIII protein or polypeptide (or fragment or variant thereof) is expressed in a recombinant host cell, typically, although not exclusively, a eukaryote.

Suitable vectors for practicing the present invention include, but are not limited to, the following viral vectors such as lambda vector system gt11, gtWES.tB, Charon 4, and plasmid vectors such as pCMV, pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993)), pQE, pIH821, pGEX, pET series (Studier et al, "Use of T7 RNA Polymerase to Direct Expression of Cloned Genes," *Methods in Enzymology* 185:60-89 (1990), which is hereby incorporated by reference in its entirety), and any derivatives thereof. Any appropriate vectors now known or later described for genetic transformation are suitable for use with the present invention.

Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Harbor, N.Y.: Cold Springs Laboratory, (1982), which is hereby incorporated by reference in its entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is generally desirable to use strong promoters in order to obtain a high level of transcription and, hence, expression of the gene. Depending upon the host cell system utilized, any one of a number of suitable promoters may be used. For instance, when cloning in *Escherichia coli*, its bacteriophages, or plasmids, promoters such as the T7 phage promoter, lac promoter, trp promoter, recA promoter, ribosomal RNA promoter, the $P_R$ and $P_L$, promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7-9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

In one embodiment, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism.

An inducible promoter is a promoter that is capable of directly or indirectly activating transcription of one or more DNA sequences or genes in response to an inducer. In the absence of an inducer, the DNA sequences or genes will not be transcribed.

The DNA construct of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., *Molecular Cloning: A Laboratory Manual*, Second Edition, Cold Spring Harbor Press, NY (1989), and Ausubel, F. M. et al. *Current Protocols in Molecular Biology*, New York, N.Y.: John Wiley & Sons (1989), each of which is hereby incorporated by reference in its entirety.

As noted, one alternative to the use of prokaryotic host cells is the use of eukaryotic host cells, such as mammalian cells, which can also be used to recombinantly produce the recombinant factor VIII of the present invention. Mammalian cells suitable for carrying out the present invention include, among others: COS (e.g., ATCC No. CRL 1650 or 1651), BHK (e.g., ATCC No. CRL 6281), CHO (e.g., ATCC No. CCL 61), HeLa (e.g., ATCC No. CCL 2), 293 (ATCC No. 1573), CHOP, and NS-1 cells.

Suitable expression vectors for directing expression in mammalian cells generally include a promoter, as well as other transcription and translation control sequences known in the art. Common promoters include SV40, MMTV, metallothionein-1, adenovirus Ela, CMV, immediate early, immunoglobulin heavy chain promoter and enhancer, and RSV-LTR.

Once the DNA construct of the present invention has been prepared, it is ready to be incorporated into a host cell. Accordingly, another aspect of the present invention relates to a method of making a recombinant cell. Basically, this method is carried out by transforming a host cell with a DNA construct of the present invention under conditions effective to yield transcription of the DNA molecule in the host cell. Recombinant molecules can be introduced into cells via transformation, particularly transduction, conjugation, mobilization, or electroporation.

In view of the recombinant technology discussed herein, another aspect of the present invention relates to a method of making a recombinant factor VIII of the present invention. This method involves growing a host cell of the present invention under conditions whereby the host cell expresses the recombinant factor VIII of the present invention. The recombinant factor VIII is then isolated. In one embodiment, the host cell is grown in vitro in a growth medium. In a particular embodiment, suitable growth media can include, without limitation, a growth medium containing a von Willebrand Factor (referred to herein as "VWF"). In this embodiment, the host cell can contain a transgene encoding a VWF or the VWF can be introduced to the growth medium as a supplement. VWF in the growth medium will allow for greater expression levels of the recombinant factor VIII. Once the recombinant factor VIII is secreted into the growth medium, it can then be isolated from the growth medium using techniques well-known by those of ordinary skill in the relevant recombinant DNA and protein arts (including those described herein). In another embodiment, the method of making the recombinant factor VIII of the present invention further involves disrupting the host cell prior to isolation of the recombinant factor VIII. In this embodiment, the recombinant factor VIII is isolated from cellular debris.

The modifications at positions corresponding to 108, 121/2302, 2328 of the WT factor VIII are particularly preferred, because they result in enhanced stability of factor VIII and, when used in combination with modifications at residues 519, 665, and/or 1984, result in significantly enhanced stability of both factor VIII and factor VIIIa. This increased stability is important with regard to circulating half-life of factor VIII and the activity of factor VIIIa during blood clotting. Furthermore, this property is significant in terms of enhancing the recovery of usable factor VIII during the purification and preparation of the protein for therapeutic use, particularly given the improved thermal and chemical stability of factor VIII.

When an expression vector is used for purposes of in vivo transformation to induce factor VIII expression in a target cell, promoters of varying strength can be employed depending on the degree of enhancement desired. One of skill in the art can readily select appropriate mammalian promoters based on their strength as a promoter. Alternatively, an inducible promoter can be employed for purposes of controlling when expression or suppression of factor VIII is desired. One of skill in the art can readily select appropriate inducible mammalian promoters from those known in the art. Finally, tissue specific mammalian promoters can be selected to restrict the efficacy of any gene transformation system to a particular tissue. Tissue specific promoters are known in the art and can be selected based upon the tissue or cell type to be treated.

Another aspect of the present invention relates to a method of treating an animal for a blood disorder such as hemophilia, particularly hemophilia A. This method involves administering to an animal exhibiting hemophilia A an effective amount of the recombinant factor VIII of the present invention, whereby the animal exhibits effective blood clotting following vascular injury. A suitable effective amount of the recombinant factor VIII can include, without limitation, between about 10 to about 50 units/kg body weight of the animal. The animal can be any mammal, but preferably a human, a rat, a mouse, a guinea pig, a dog, a cat, a monkey, a chimpanzee, an orangutan, a cow, a horse, a sheep, a pig, a goat, or a rabbit.

The recombinant factor VIII of the present invention can be used to treat uncontrolled bleeding due to factor VIII deficiency (e.g., intraarticular, intracranial, or gastrointestinal hemorrhage) in hemophiliacs with and without inhibitory antibodies and in patients with acquired factor VIII deficiency due to the development of inhibitory antibodies. In a particular embodiment, the recombinant factor VIII, alone, or in the form of a pharmaceutical composition (i.e., in combination with stabilizers, delivery vehicles, and/or carriers) is infused into patients intravenously according to the same procedure that is used for infusion of human or animal factor VIII.

Alternatively, or in addition thereto, the recombinant factor VIII can be administered by administering a viral vector such as an adeno-associated virus (Gnatenko et al., "Human Factor VIII Can Be Packaged and Functionally Expressed in an Adeno-associated Virus Background: Applicability to Hemophilia A Gene Therapy," *Br. J. Haematol.* 104:27-36 (1999), which is hereby incorporated by reference in its entirety), or by transplanting cells genetically engineered to produce the recombinant factor VIII, typically via implantation of a device containing such cells. Such transplantation typically involves using recombinant dermal fibroblasts, a non-viral approach (Roth et al., "Nonviral Transfer of the Gene Encoding Coagulation Factor VIII in Patients with Sever Hemophilia," *New Engl. J. Med.* 344:1735-1742 (2001), which is hereby incorporated by reference in its entirety).

The treatment dosages of recombinant factor VIII that should be administered to a patient in need of such treatment will vary depending on the severity of the factor VIII deficiency. Generally, dosage level is adjusted in frequency, duration, and units in keeping with the severity and duration of each patient's bleeding episode. Accordingly, the recombinant factor VIII is included in a pharmaceutically acceptable carrier, delivery vehicle, or stabilizer in an amount sufficient to deliver to a patient a therapeutically effective amount of the protein to stop bleeding, as measured by standard clotting assays.

Factor VIII is classically defined as that substance present in normal blood plasma that corrects the clotting defect in plasma derived from individuals with hemophilia A. The coagulant activity in vitro of purified and partially-purified forms of factor VIII is used to calculate the dose of recombinant factor VIII for infusions in human patients and is a reliable indicator of activity recovered from patient plasma and of correction of the in vivo bleeding defect. There are no reported discrepancies between standard assay of novel factor VIII molecules in vitro and their behavior in the dog infusion model or in human patients, according to Lusher et al., "Recombinant Factor VIII for the Treatment of Previously Untreated Patients with Hemophilia A—Safety, Efficacy, and Development of Inhibitors," *New Engl. J. Med.* 328:453-459 (1993); Pittman et al., "A2 Domain of Human Recombinant-derived Factor VIII is Required for Procoagulant Activity but not for Thrombin Cleavage," *Blood* 79:389-397 (1992); and Brinkhous et al., "Purified Human Factor VIII Procoagulant Protein Comparative Hemostatic Response After Infusions into Hemophilic and von Willebrand Disease Dogs," *Proc. Natl. Acad. Sci.* 82:8752-8755 (1985), which are hereby incorporated by reference in their entirety.

Usually, the desired plasma factor VIII activity level to be achieved in the patient through administration of the recombinant factor VIII is in the range of 30-100% of normal. In one embodiment, administration of the therapeutic recombinant factor VIII is given intravenously at a preferred dosage in the range from about 5 to 50 units/kg body weight, and particularly in a range of 10-50 units/kg body weight, and further particularly at a dosage of 20-40 units/kg body weight; the interval frequency is in the range from about 8 to 24 hours (in severely affected hemophiliacs); and the duration of treatment in days is in the range from 1 to 10 days or until the bleeding episode is resolved. See, e.g., Roberts and Jones, "Hemophilia and Related Conditions—Congenital Deficiencies of Prothrombin (Factor II, Factor V, and Factors VII to XII)," Ch. 153, 1453-1474, 1460, in *Hematology*, Williams, W. J., et al., ed. (1990), which is hereby incorporated by reference in its entirety. Patients with inhibitors may require a different amount of recombinant factor VIII than their previous form of factor VIII. For example, patients may require less recombinant factor VIII because of its higher specific activity than the wild-type VIII and its decreased antibody reactivity. As in treatment with human or plasma-derived factor VIII, the amount of therapeutic recombinant factor VIII infused is defined by the one-stage factor VIII coagulation assay and, in selected instances, in vivo recovery is determined by measuring the factor VIII in the patient's plasma after infusion. It is to be understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed recombinant factor VIII.

Treatment can take the form of a single intravenous administration of the recombinant factor VIII or periodic or continuous administration over an extended period of time, as required. Alternatively, therapeutic recombinant factor VIII can be administered subcutaneously or orally with liposomes in one or several doses at varying intervals of time.

The recombinant factor VIII can also be used to treat uncontrolled bleeding due to factor VIII deficiency in hemophiliacs who have developed antibodies to human factor VIII.

It has been demonstrated herein that the recombinant factor VIII of the present invention can differ in specific activity from the wild-type factor VIII and retain a higher specific activity for a longer duration following activation. Factor VIII proteins having greater procoagulant activity from wild-type factor VIII are useful in treatment of hemophilia because lower dosages will be required to correct a patient's factor VIII deficiency. This will not only reduce medical expense for both the patient and the insurer, but also reduce the likelihood of developing an immune response to the factor VIII (because less antigen is administered).

EXAMPLES

The following examples are provided to illustrate embodiments of the present invention, but they are by no means intended to limit its scope.

Materials & Methods

Reagents: Recombinant factor VIII (KOGENATE™) and the monoclonal antibodies 58.12 and 2D2 were generous gifts from Dr. Lisa Regan of Bayer Corporation (Berkeley, Calif.). Phospholipid vesicles containing 20% phosphatidylcholine (PC), 40% phosphatidylethanolamine (PE), and 40% phosphatidylserine (PS) were prepared using octylglucoside as described previously (Mimms et al., "Phospholipid Vesicle Formation and Transmembrane Protein Incorporation Using Octyl Glucoside," *Biochemistry* 20:833-840 (1981), which is hereby incorporated by reference in its entirety). The reagents α-thrombin, factor VIIa, factor IXaβ, factor X, and factor Xa (Enzyme Research Laboratories, South Bend, Ind.), hirudin (DiaPharma, West Chester, Ohio), phospholipids (Avanti Polar Lipids, Alabaster, Ala.), the chromogenic Xa substrate, Pefachrome Xa (Pefa-5523, $CH_3OCO$-D-Cha-Gly-Arg-pNA.AcOH; Centerchem Inc. Norwalk Conn.), recombinant human tissue factor (rTF), Innovin (Dade Behring, Newark, Del.), fluorogenic substrate, Z-Gly-Gly-Arg-AMC (Calbiochem, San Diego, Calif.), thrombin calibrator (Diagnostica Stago, Parsippany, N.J.), and acrylodan (Molecular Probes, Eugene, Oreg.) were purchased from the indicated vendors.

Expression and Purification of WT and Variant Factor VIII: Recombinant WT and variant factor VIII forms were stably expressed in BHK cells and purified as described previously (Wakabayashi et al., "Residues 110-126 in the A1 Domain of Factor VIII Contain a $Ca^{2+}$ Binding Site Required for Cofactor Activity," *J Biol Chem.* 279:12677-12684 (2004), which is hereby incorporated by reference in its entirety). After transfection there were no significant differences in the amounts of factor VIII secretion among the variants. Protein yields for the variants ranged from >10 to ~100 μg from two 750 $cm^2$ culture flasks, with purity from ~85% to >95% as judged by SDS-PAGE. The primary contaminant in the factor VIII preparations was albumin and at the concentrations present in the factor VIII showed no effect on stability or activity parameters. Factor VIII concentration was measured by ELISA and factor VIII activity was determined by one-stage clotting assay and two-stage chromogenic factor Xa generation assay, both of which are described below.

Western Blotting: Factor VIII proteins (0.34 μg) were activated by thrombin (20 nM) for 30 min at 23° C. and subjected to electrophoresis under either non-reducing or reducing (0.1 M dithiothreitol) conditions using 10% polyacrylamide gels run at constant voltage (150V). Gels were transferred to a polyvinylidene fluoride membrane, probed with an anti-A1 domain (58.12) or anti-A3 domain (2D2) monoclonal antibody and protein bands were visualized using chemifluorescence. The chemifluorescence substrate (ECF substrate, GE Healthcare, Piscataway, N.J.) was reacted and the fluorescence signal scanned using a phosphoimager (Storm 860, GE Healthcare).

ELISA: A sandwich ELISA was performed to measure the concentration of factor VIII proteins as previously described (Wakabayashi et al., "A Glu113Ala Mutation within a Factor VIII $Ca^{2+}$-Binding Site Enhances Cofactor Interactions in Factor Xase," *Biochemistry* 44:10298-10304 (2005), which is hereby incorporated by reference in its entirety) using purified commercial recombinant factor VIII (KOGENATE™, Bayer Corporation) as a standard. Factor VIII capture used the anti-C2 monoclonal antibody (GMA8003, Green Mountain Antibodies) and the anti-A2 monoclonal antibody, R8B12 (GMA8012, Green Mountain Antibodies) was employed for factor VIII detection following biotinylation.

One-stage Clotting Assay: One-stage clotting assays were performed using substrate plasma chemically depleted of factor VIII (Over, "Methodology of the One-stage Assay of Factor VIII (VIII:C)," *Scand J Haematol Suppl.* 41:13-24 (1984), which is hereby incorporated by reference in its entirety) and assayed using a Diagnostica Stago clotting instrument. Plasma was incubated with APTT reagent (General Diagnostics) for 6 min at 37° C. after which a dilution of factor VIII was added to the cuvette. After 1 min the mixture was recalcified, and clotting time was determined and compared to a pooled normal plasma standard.

Two-stage Chromogenic Factor Xa Generation Assay: The rate of conversion of factor X to factor Xa was monitored in a purified system (Lollar et al., "Factor VIII and Factor VIIIa," *Methods Enzymol.* 222:128-143 (1993), which is hereby incorporated by reference in its entirety) according to methods previously described (Wakabayashi et al., "Metal Ion-independent Association of Factor VIII Subunits and the Roles of Calcium and Copper Ions for Cofactor Activity and Inter-subunit Affinity," *Biochemistry* 40:10293-10300 (2001); Wakabayashi et al., "$Ca^{2+}$ Binding to Both the Heavy and Light Chains of Factor VIII Is Required for Cofactor Activity," *Biochemistry* 41:8485-8492 (2002), each of which is hereby incorporated by reference in its entirety). Factor VIII (1 nM) in buffer containing 20 mM N-[2-hydroxyethyl]piperazine-N'-[2-ethanesulfonic acid] (HEPES), pH 7.2, 0.1 M NaCl, 0.01% Tween 20, 0.01% BSA, 5 mM $CaCl_2$ (Buffer B), and 10 μM PSPCPE vesicles was activated with 20 nM α-thrombin for 1 min. The reaction was stopped by adding hirudin (10 U/ml) and the resulting factor VIIIa was reacted with factor IXa (40 nM) for 1 min. Factor X (300 nM) was added to initiate reactions which were quenched after 1 min by the addition of 50 mM EDTA. Factor Xa generated was determined following reaction with the chromogenic substrate Pefachrome Xa (0.46 mM final concentration). All reactions were run at 23° C.

Factor VIII Activity at Elevated Temperature: WT factor VIII or factor VIII variants (4 nM) in buffer B were incubated at 57° C. (pH at this temperature=6.94). Aliquots were removed at the indicated times, cooled to room temperature, and residual factor VIII activity was determined using a two-stage factor Xa generation assay.

Factor VIIIa activity decay: WT and mutant factor VIII (1.5 nM) in buffer B containing 20 μM PSPCPE vesicles were activated using 20 nM thrombin for 1 min at 23° C. Reactions were immediately quenched by hirudin (10 U/ml) to inactivate thrombin, aliquots removed at the indicated times, and activity was determined using the factor Xa generation assay following addition of factor IXa (40 nM) and factor X (300 nM).

Factor VIII activity inhibition by guanidinium chloride: WT and factor VIII variants (50 nM) in buffer B plus 0-1.8 M guanidinium chloride were incubated for 2 hrs at 23° C. Aliquots were diluted (1/50) in buffer A containing 20 μM PSPCPE vesicles and activated by 5 nM thrombin for 1 min. Reactions were immediately quenched with hirudin (10 U/ml) and activity was determined by factor Xa generation assay following addition of factor IXa (40 nM) and FX (300 nM). Residual guanidinium chloride (<36 mM) did not inhibit the proteolytic activation of factor VIII or its cofactor activity.

Thermal denaturation of reconstituted A1 and A3C1C2 or A3C1 subunit as detected by FXa generation assay—A1 subunit (50 nM) from WT or Ala108Ile factor VIII was reconstituted with A3C1C2 (200 nM) or A3C1 (500 nM) at 37° C. for 2 hr in 10 mM MES, pH 6.5, 0.15 M NaCl, 0.01% Tween 20, 0.01% BSA, 5 mM $CaCl_2$. Samples were incubated at 55° C. (A3C1C2) or 52° C. (A3C1) (pH at this temperature=6.94), aliquots were taken at indicated times, and further incubated with 200 nM A2 subunit at 23° C. for 30 min. Samples were then diluted 1:20 with buffer B containing 20 μM PSPCPE vesicles and reconstituted factor VIIIa activity was measured directly by factor Xa generation assay in the absence of the thrombin activation step. Data were fitted to the single exponential decay equation by non-linear least squares regression and parameter values were obtained.

Thrombin generation assay—The amount of thrombin generated in plasma was measured by Calibrated Automated Thrombography using methods previously described (Wakabayashi et al., "Combining Mutations of Charged Residues at the A2 Domain Interface Enhances Factor VIII Stability over Single Point Mutations," *J. Thromb. Haemost.* 7:438-444 (2009), which is hereby incorporated by reference in its entirety). Briefly, factor VIII deficient plasma (<1% residual activity, platelet-poor) from severe hemophilia A patients lacking factor VIII inhibitor (George King Bio-Medical, Overland Park, Kans.) was mixed at 37° C. with a final concentration of 0.3 nM factor VIII, 0.5 pM rTF, 4 μM PSPCPE vesicles, 433 μM fluorogenic substrate, 13.3 mM $CaCl_2$, and 105 nM thrombin calibrator. The development of a fluorescent signal was monitored at 8 second intervals using a Microplate Spectrofluorometer (Spectramax Gemini, Molecular Devices, Sunnyvale, Calif.) with a 355 nm (excitation)/460 nm (emission) filter set. Fluorescent signals were corrected by the reference signal from the thrombin calibrator samples and actual thrombin generation in nM was calculated.

Data analysis: For activity decay analysis of factor VIII/VIIIa, activity values as a function of time were fitted to a single exponential decay curve by non-linear least squares regression using the equation, $$A = A_0 \cdot e^{-k \cdot t}$$

where A is residual factor VIIIa activity (nM/min/nM factor VIII), $A_0$ is the initial activity, k is the apparent rate constant, and t is the time (minutes) of reaction of factor VIII (for factor VIII thermal decay experiments) or of factor VIIIa after thrombin was quenched (for factor VIIIa decay measurements). Factor VIII activity inhibition by guanidinium was fitted to a linear equation by least squares regression using the equation, $$A = 50 - k \cdot (X - IC_{50})$$

where A is the normalized activity [=100(%)], $IC_{50}$ is the inhibitor (guanidinium chloride) concentration (M) at 50% activity, X is the guanidinium chloride concentration (M), and k is the slope. Determinations for A1-A3C1C2 binding affinity used the quadratic equation:

$$F = \frac{F_{max}}{B} \cdot \frac{(B + K_d + X)^2 - \sqrt{(B + K_d + X)^2 - 4 \cdot B \cdot X}}{2}$$

where $F_{max}$ is the maximum increase in fluorescence at saturation, B is the A1 concentration (=15 nM), $K_d$ is the dissociation constant, and X is the concentration of A3C1C2 in nM, Nonlinear least-squares regression analysis was performed using Kaleidagraph (Synergy, Reading, Pa.). A Student's t-test was performed for statistical analysis.

Example 1

Figure 3B:
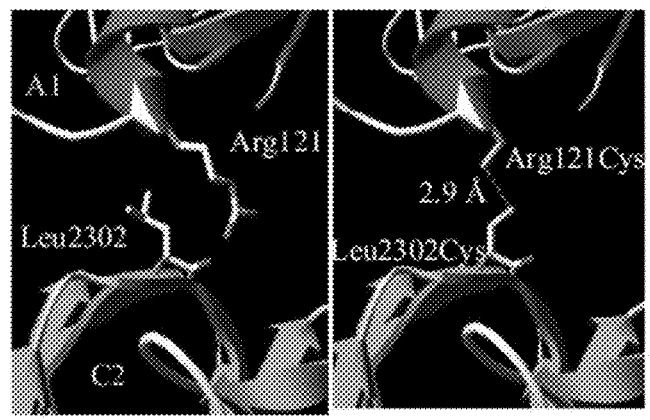
Figure 3C:
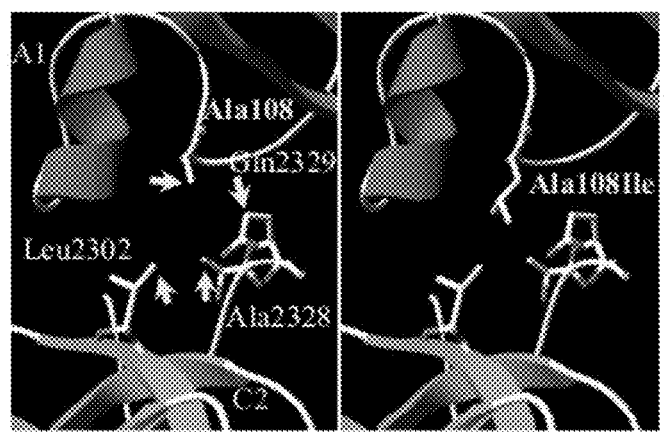

Recombinant Expression and Purification of Factor VIII Mutants Possessing Modified A1 and C2 Domain Interactions The A1 and C2 domains show close proximity to one another in the factor VIII crystal structure (FIG. 3A). These regions were investigated with the aim towards enhancing inter-domain interactions to positively alter affinity and stability parameters. Examination of the A1-C2 interface provided two possible approaches for increasing the inter-domain affinity. Although the orientation of side chains cannot be discerned due to the resolution (~4 Å) of the structure (4), the putative spatial separation of several paired residues indicated that mutagenesis of these residues to Cys could result in formation of a nascent inter-domain disulfide bridge. Paired A1/C2 domain residues were identified that appeared to meet this distance requirement and included Ser119/Pro2300, Gln120/Pro2299, Arg121/Leu2302, Ala108/Ala2328, and Trp106/Ala2328.

Double mutations where each residue of the respective pair was replaced with Cys were prepared as B-domainless factor VIII—lacking residues Gln744-Ser1637 in the B-domain (Doering et al., "Expression and Characterization of Recombinant Murine Factor VIII," *Thromb. Haemost* 88:450-458 (2002), which is hereby incorporated by reference in its entirety)—using previously described methods (Wakabayashi et al., "Residues 110-126 in the A1 Domain of Factor VIII Contain a $Ca^{2+}$-Binding Site Required for Cofactor Activity," *J. Biol. Chem* 279:12677-12684 (2004), which is hereby incorporated by reference in its entirety). Briefly, B-domainless factor VIII cDNA was restricted from the factor VIII expression construct HSQ-MSAB-NotI-RENeo using the endonucleases XhoI and NotI, and then cloned into the Bluescript II K/S-vector. Factor VIII molecules bearing one or more point mutations were constructed by introducing mutations into shuttle constructs using the Stratagene QuikChange site-directed mutagenesis kit. Upon confirmation of the presence of only the desired mutations by sequencing, the appropriate fragment was restricted and cloned back into the factor VIII expression construct. Presence of only the desired mutations was again confirmed by a second round of sequencing. Of the five variants examined, only the Arg121Cys/Leu2302Cys variant (FIG. 3B) retained a wild-type like specific activity (~86% the WT value, Table 1) and was further evaluated.

Recombinant WT and variant factor VIII forms were stably expressed in BHK cells and purified as previously described (Lollar and Parker, "pH-dependent Denaturation of Thrombin-activated Porcine Factor VIII," *J. Biol. Chem* 265:1688-1692 (1990), which is hereby incorporated by reference in its entirety). Protein yields for the variants ranged from >10 to ~100 μg from two 750 $cm^2$ culture flasks, with purity >90% as judged by SDS-PAGE. The primary contaminant in the factor VIII preparations was albumin. Factor VIII concentrations were measured using an Enzyme-Linked Immunoadsorbant Assay (ELISA) and factor VIII activity was determined by one-stage clotting and two-stage chromogenic factor Xa generation assays described supra.

In addition, a small cavity in the A1-C2 interface that potentially exists was noted, this putative cavity is mainly surrounded by alkyl groups from Ala108, Ala2328, Leu2302, and Gln2329 (FIG. 3C), with the side chain of Ala108 proposed to be directed towards the C2 domain. In an effort to increase hydrophobic interactions within this area, several variants were prepared to introduce bulky hydrophobic groups in these domains. This was carried out by mutating Ala residues to Ile, Leu, and Val (Ala108Ile, Ala108Leu, Ala108Val, Ala2328Ile, Ala2328Leu, and Ala2328Val) in a B-domainless factor VIII cDNA using the procedures described in the preceding paragraph. Of the variants prepared, the Ala108Ile factor VIII variant showed minimal effects on factor VIII specific activity (~74% the WT value, Table 1); the Ala108Leu and Ala108Val variants showed greater diminution of factor VIII specific activity.

The A1 subunit was purified from WT or Ala108Ile factor VIII. Factor VIII (1-3 µM) was reacted with thrombin (50 nM) in 20 mM HEPES, pH 7.2, 0.1 M NaCl, 0.01% Tween 20 (buffer A) for 30 min and treated with 50 mM EDTA overnight at 4° C. After a 1:4 dilution with buffer A, the samples were subjected to chromatography using a heparin Sepharose column (1.5 cm×0.7 cm in diameter, GE Healthcare, Piscataway, N.J.). The flow through fraction was collected and applied to a Q-Sepharose column (1.5 cm×0.7 cm in diameter, GE Healthcare). After the column was washed with buffer A, bound A1 subunit was eluted with 20 mM HEPES, pH 7.2, 0.8 M NaCl, 0.01% Tween20, and purified A1 subunit was kept frozen at 80° C. until use. A2 and A3C1C2 subunits were completely absorbed by the heparin Sepharose column step and the final A1 product was >95% pure as judged by SDS-PAGE. A2 and A3C1C2 subunits were purified from recombinant factor VIII (Kogenate™) as described previously (Fay and Smudzin, "Characterization of the Interaction Between the A2 Subunit and A1/A3-C1-C2 Dimer in Human Factor VIIIa," *J. Biol. Chem* 267:13246-13250 (1992), which is hereby incorporated by reference in its entirety). A3C1 subunit was purified from C2 domain-deleted factor VIII (Wakabayashi et al., "Factor VIII Lacking the C2 Domain Retains Cofactor Activity in vitro," *J. Biol. Chem* 285:25176-25184 (2010), which is hereby incorporated by reference in its entirety) using the same method for A3C1C2 purification.

Purified A1 subunit from WT and Ala108Ile factor VIII was labeled with acrylodan by sulfhydryl specific protein modification as previously described (Wakabayashi et al., "Metal Ion-independent Association of Factor VIII Subunits and the Roles of Calcium and Copper Ions for Cofactor Activity and Inter-subunit Affinity," *Biochemistry* 40:10293-10300 (2001), which is hereby incorporated by reference in its entirety). A1 (15 nM) from WT or Ala108Ile factor VIII was reconstituted with A3C1C2 subunit (0-300 nM) at 37° C. for 2 h in buffer B at pH 7.4. Fluorescence measurements were performed using an Aminco-Bowman Series 2 Luminescence Spectrometer (Thermo Spectronic, Rochester, N.Y.) at 23° C. at an excitation wavelength of 395 nm (2 nm bandwidth). Fluorescence emission was monitored at 480-490 nm (8 nm bandwidth) and all spectra were corrected for background. Data were fitted to a quadratic equation by non-linear least squares regression and parameter values were obtained.

Example 2

Figure 4:
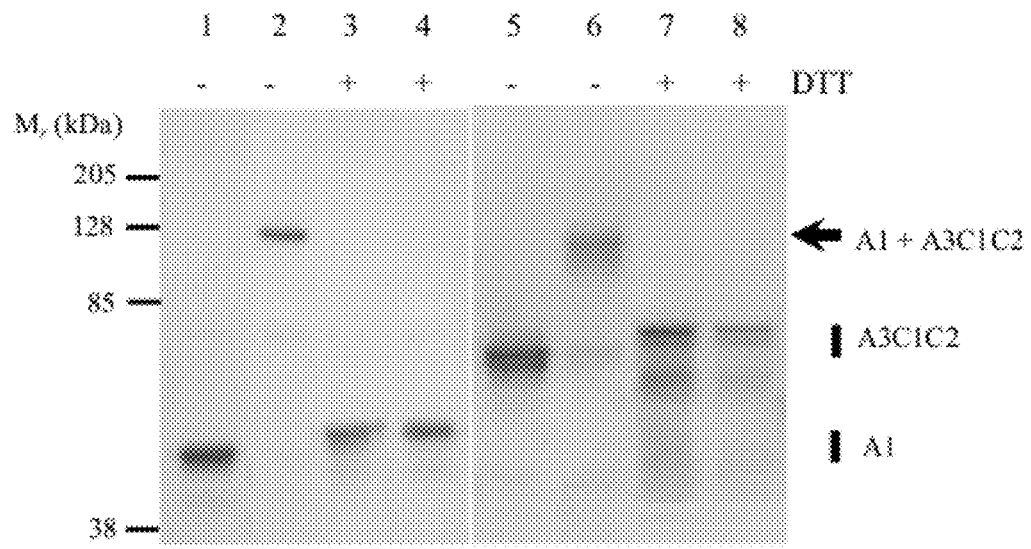

Confirmation of Disulfide Bridge in Arg121Cys/Leu2302Cys Factor VIII Variant Evidence for high efficiency disulfide bridging between factor VIII A1 and A3C1C2 domains in this double mutant, as judged by Western Blotting is shown in FIG. 4. For this analysis, WT factor VIII and the Arg121Cys/Leu2302Cys factor VIII variant were cleaved with thrombin to generate the factor VIIIa heterotrimer prior to SDS-PAGE, which was then run in the absence and presence of disulfide bond reduction using DTT. Blots were probed with an anti-A1 antibody (58.12, lanes 1-4) and an anti-A3 antibody (2D2, lanes 5-8). Both A1 and A3C1C2 subunits derived from the factor VIII Arg121Cys/Leu2302Cys variant were detected at the ~120 kDa band, consistent with the sum of their mol masses under non-reducing conditions (lanes 2 and 6), while reduction by 0.1 M DTT yielded the separated subunits (lanes 4 and 8). Based upon the band densities of bridged and free subunits in the non-reduced lanes, it appeared that >90% of the variant molecules were disulfide-linked.

Example 3

Affinity of the WT and Ala108Ile Factor VIII Variant A1 Subunits for A3C1C2

Figure 5:
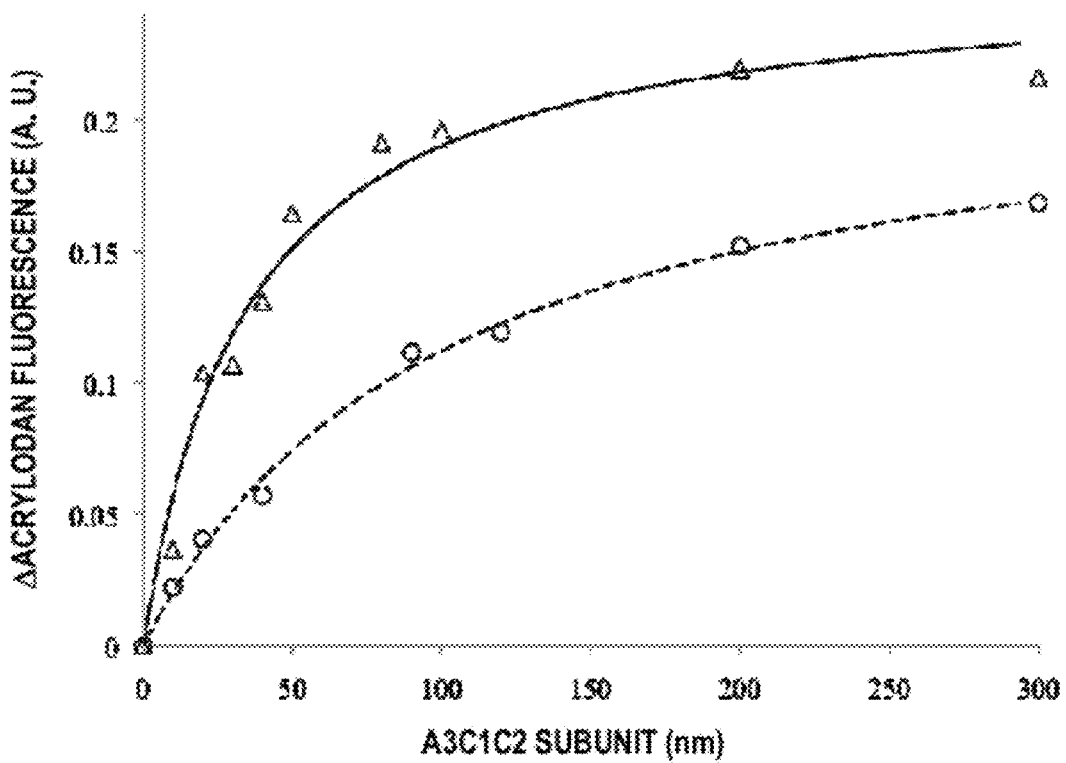

To assess the affinity of the Ala108Ile A1 domain for C2 domain, the purified factor VIII variant and WT were treated with thrombin and the A1 subunits were separately purified as described supra. A1 subunits were then reacted with the environment-sensitive fluorescent probe, acrylodan, and these reagents were used to probe binding with the A3C1C2 subunit. The site for acrylodan attachment is likely the lone free thiol in A1 at Cys310, which is in close proximity (<15 Å) to residues in the A3 domain of light chain (Ngo et al., "Crystal Structure of Human Factor VIII: Implications for the Formation of the Factor IXa:Factor VIIIa Complex," *Structure* 16:597-606 (2008), which is hereby incorporated by reference in its entirety). Indeed, increases in the emission fluorescence from acrylodan-labeled A1 (AcA1) subunit have been previously observed when A3C1C2 was bound to the molecule (Wakabayashi et al, "Metal-ion Independent Factor VIII Subunit Association and the Role of Calcium and Copper for Its Affinity and Activity," *Biochemistry* 40:10293-10300 (2001); Ansong et al., "Factor VIII A3 Domain Residues 1954-1961 Represent an A1 Domain-Interactive Site," *Biochemistry* 44:8850-8857 (2005), each of which is hereby incorporated by reference in its entirety). Titration of AcA1 with A3C1C2 was performed as described supra and the results are shown in FIG. 5. AcA1 (15 nM) fluorescence from both the WT and Ala108Ile subunits saturably increased as the A3C1C2 concentration increased. The estimated $K_d$ of this interaction for WT and Ala108Ile A1 subunits were 88.7±9.8 nM and 24.1±4.1 nM, respectively. The $K_d$ value for WT was somewhat higher than a previously reported value (~50 nM) (Ansong et al., "Factor VIII A3 Domain Residues 1954-1961 Represent an A1 Domain-Interactive Site," *Biochemistry* 44:8850-8857 (2005), which is hereby incorporated by reference in its entirety) likely due to slightly higher pH (7.4) employed for the binding conditions (Wakabayashi et al., "pH-dependent Association of Factor VIII Chains: Enhancement of Affinity at Physiological pH by $Cu^{2+}$," *Biochim. Biophys. Acta* 1764:1094-1101 (2006), which is hereby incorporated by reference in its entirety). This result indicated a ~4-fold increase in affinity of Ala108Ile A1 for A3C1C2 as compared with the WT A1 subunit for A3C1C2. The estimated maximal values in fluorescence for WT and Ala108Ile were 0.221±0.009 and 0.245±0.011 respectively, and were not significantly different (p>0.1).

Example 4

Stability of Factor VIII Arg121Cys/Leu2302Cys and Ala108Ile Variants

The above results demonstrate that introduction of the disulfide bridge or increasing the hydrophobic character at the A1-C2 interface stabilizes this inter-domain interaction. To test the functional consequences of these mutations, stability parameters of factor VIII (factor VIIIa) were evaluated by several methods. Thermal denaturation experiments were performed at 57° C. as described supra. Data shown in FIG. 6A were fitted to a single exponential decay curve using non-linear least squares regression. WT factor VIII (circles) decayed to ~40% the initial activity level in 6-7 min at 57° C.

On the other hand, the Arg121Cys/Leu2302Cys variant (triangles) retained >40% activity up to 20 min, whereas the Ala108Ile variant (squares) retained this level for >30 min. Overall, decay rates for the Arg121Cys/Leu2302Cys and Ala108Ile variants obtained by curve-fit were reduced by 3.1- and 4.2-fold, respectively, compared to the WT factor VIII value (see Table 1 below).

TABLE 1

Properties of Wild type Factor VIII and Variants

|  | Specific Activity (%) | Factor VIII Decay Rate (min$^{-1}$) | IC$_{50}$ (M) | Factor VIIIa Decay Rate (min$^{-1}$) |
| --- | --- | --- | --- | --- |
| WT | 100.0 ± 8.2 | 0.143 ± 0.003 (1.0) | 0.814 ± 0.010 (1.00) | 0.154 ± 0.006 (1.00) |
| R121C/ L2302C | 86.4 ± 3.8 | 0.047 ± 0.001 (0.32) | 0.826 ± 0.005 (1.01) | 0.132 ± 0.004 (0.86) |
| A108I | 73.7 ± 3.9 | 0.034 ± 0.002 (0.24) | 0.892 ± 0.008 (1.10) | 0.119 ± 0.008 (0.77) |

Figure 6A:
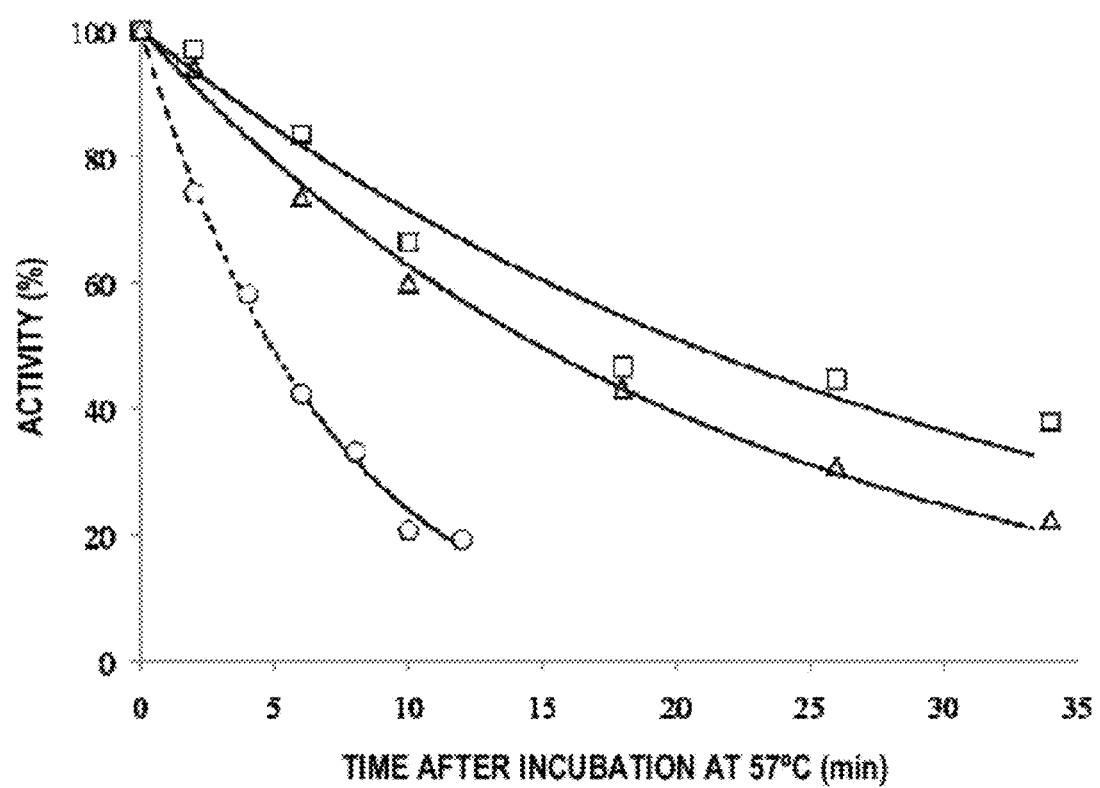
Figure 6B:
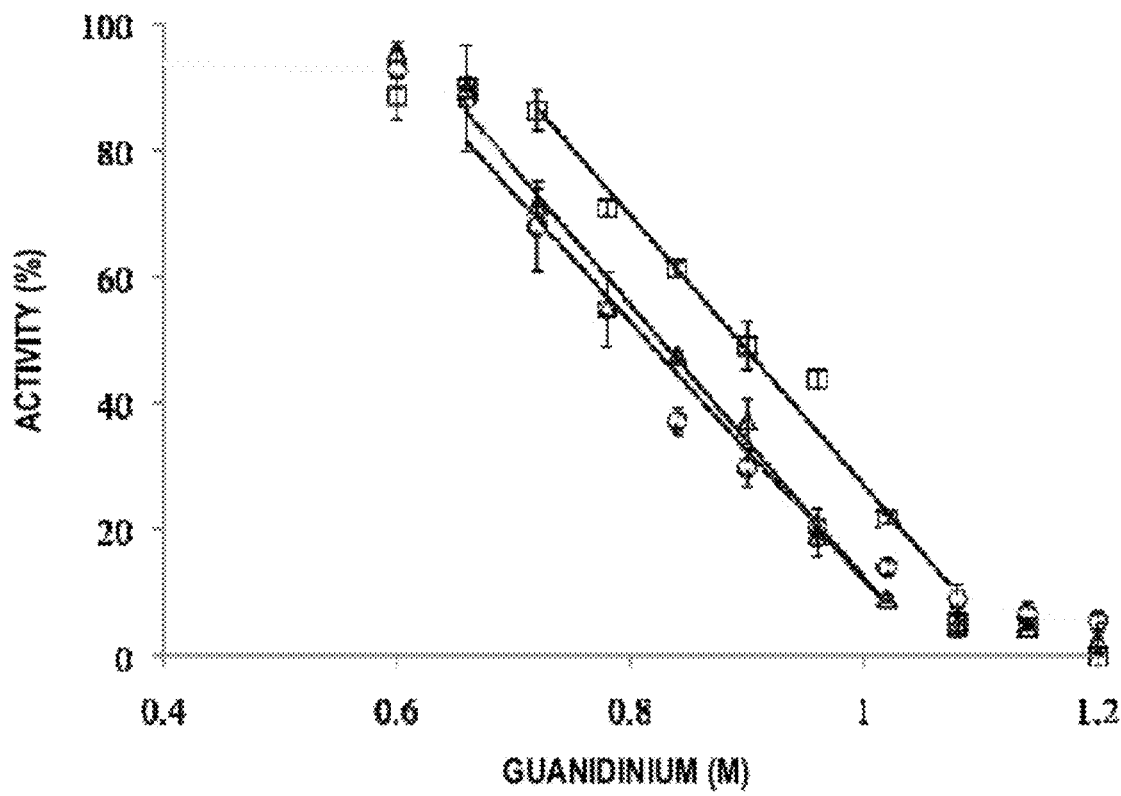
Figure 6C:
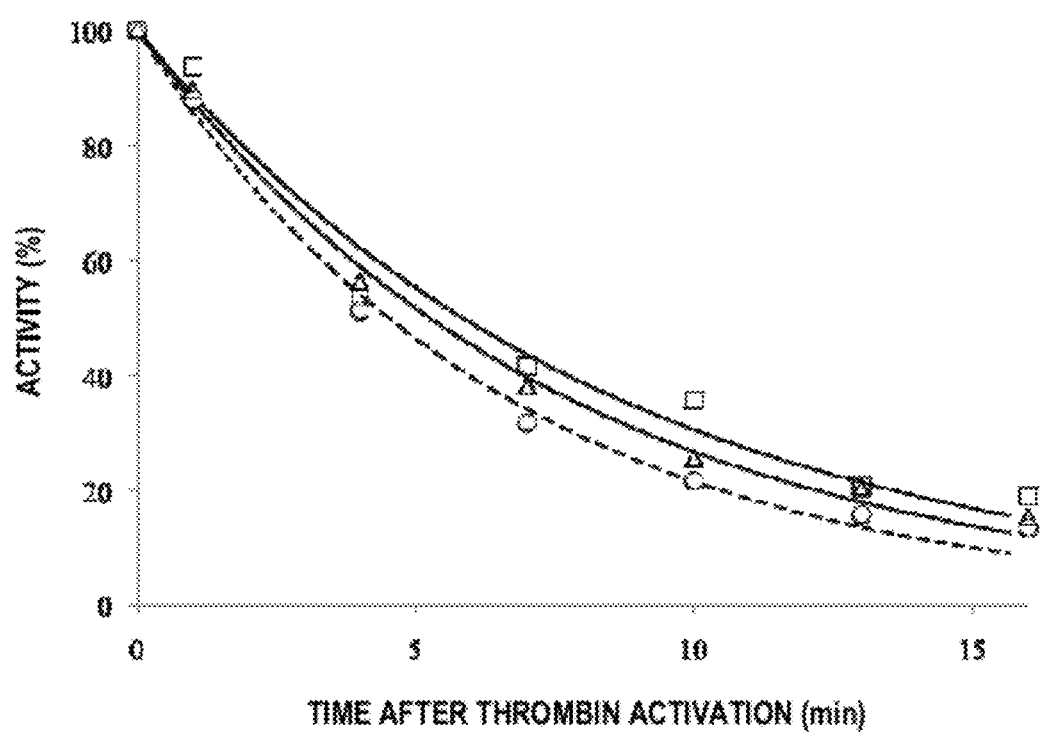

Specific activity was determined by factor Xa generation assay as described above and expressed as a relative activity compared to WT value. Factor VIII decay data at 57° C. as shown in FIG. 6A, and factor VIIIa spontaneous decay data as shown in FIG. 6C were fitted to a single exponential decay curve. Guanidinium denaturation data as shown in FIG. 6B were fitted to a linear response curve by non-linear least squares regression and IC$_{50}$ values with standard deviations were obtained. Values in parentheses are relative to the WT value.

In a complementary series of experiments, factor VIII stability was examined following a 2 h exposure to 0.6-1.2 M guanidinium (FIG. 6B). As the concentration of guanidinium increased, factor VIII activity was reduced to near zero as an indication of denaturation. Using the range of linear response (~0.6-1 M), data points were fitted by a linear equation and the IC$_{50}$ values were obtained (see Table 1). Factor VIII activity of the Ala108Ile variant was significantly more stable than WT showing a ~10% higher IC$_{50}$ values compared with WT ($p<0.001$), while the IC$_{50}$ determined for the Arg121Cys/Leu2302Cys variant was only slightly increased (~2% greater than WT, Table 1). Overall, the stability data for the disulfide bridged variant suggested that the covalent bond between A1 and C2 subunits significantly increased factor VIII thermal stability while showing little stabilizing effect in the presence of guanidinium. This result indicated that dissociation of factor VIII heavy and light chains may be a prominent cause for activity loss at elevated temperature, but that chain dissociation may not represent a primary mode for activity loss due to chemical denaturation. Alternatively, the Ala108Ile mutation demonstrated a more global protective effect in increasing factor VIII stability towards either thermal or chemical denaturation. Control experiments were performed to determine whether there was any time-dependent change in activity following the thermal or chemical denaturation step and return of factor VIII to either ambient temperature or dilution of denaturant, respectively. Factor VIII was assayed from 30 seconds to 1 hour, and no significant change in activity was observed.

Factor VIIIa activity is labile due to A2 subunit dissociation following proteolytic activation (Fay et al., "Human Factor VIIIa Subunit Structure: Reconstitution of Factor VIIIa from the Isolated A1/A3-C1-C2 Dimer and A2 Subunit," *J. Biol. Chem* 266:8957-8962 (1991); Lollar et al., "pH-dependent Denaturation of Thrombin-activated Porcine Factor VIII," *J. Biol. Chem* 265:1688-1692 (1990); Lollar et al., "Coagulant Properties of Hybrid Human/Porcine Factor VIII Molecules," *J. Biol. Chem* 267:23652-23657 (1992), each of which is hereby incorporated by reference in its entirety). To determine whether these mutations affected factor VIIIa decay, experiments were performed to assess rates of loss of factor VIIIa activity over time. As shown in FIG. 6C, reaction conditions employed resulted in the loss of ~50% of WT factor VIIIa activity at ~6 min after thrombin activation, while ~10% activity remained after 16 min. The observed factor VIIIa activity decay was slightly reduced for both Arg121Cys/Leu2302Cys and Ala108Ile variants which showed ~40% activity in 7-8 min and demonstrated decay rates that were 1.2- and 1.3-fold greater than WT factor VIII, respectively (see Table 1). These results demonstrated only minor effects on the inter-subunit interactions involving A2 subunit following modification of the A1 and C2 domain interface.

Example 5

Figure 7A:
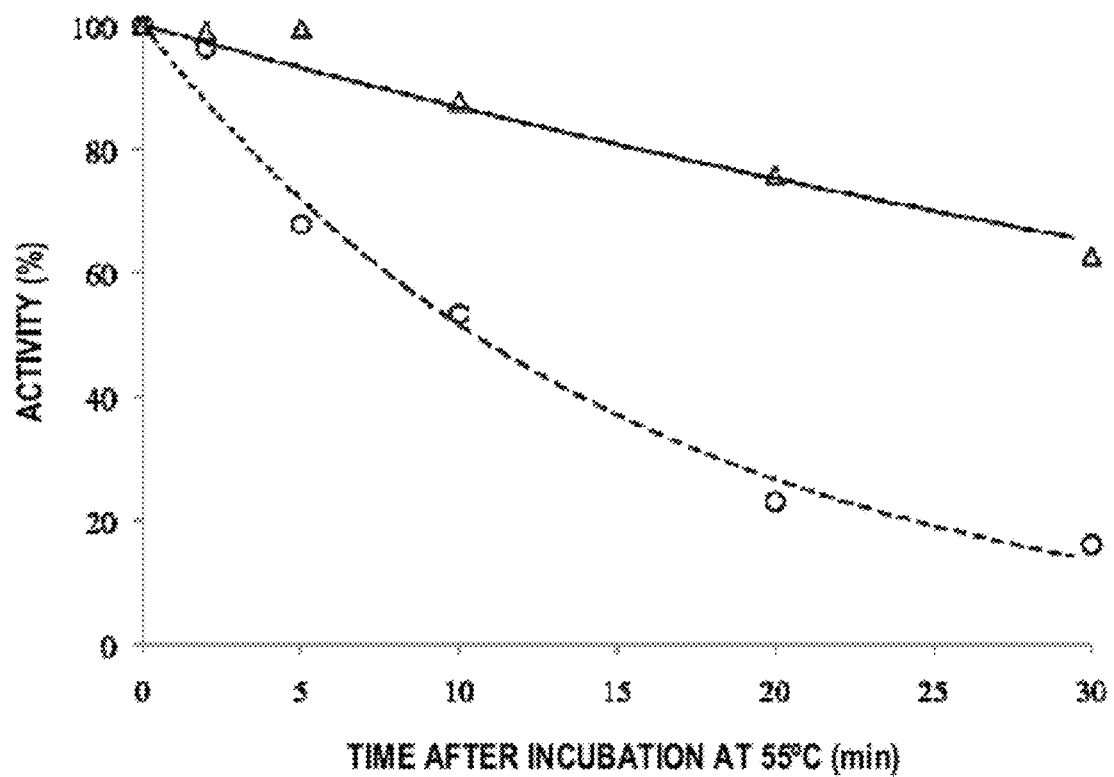

Stability of Reconstituted Ala108Ile or WT A1 Subunit with A3C1C2 or A3C1 Subunits The thermal stability for the A1/A3C1C2 dimer was assessed following its reconstitution from isolated subunits. Purified WT A1 or Ala108Ile A1 subunits was reconstituted with A3C1C2 subunit at 37° C. for 2 hrs and the stability of the A1/A3C1C2 dimer at elevated temperature (55° C.) was measured by factor Xa generation assay following addition of A2 subunit as described in Methods. As shown in FIG. 7A, factor VIIIa activity reconstituted from WT-A1 decayed to ~25% its original value at 20 min (circles) while ~80% of the original activity level remained for the A1 subunit containing the Ala108Ile mutation (triangles). The estimated decay rates for WT and the mutant factor VIIIa forms were 0.066±0.005 and 0.014±0.001 min$^{-1}$, respectively, showing a 4.6-fold rate reduction for the variant compared to WT factor VIII.

Figure 7B:
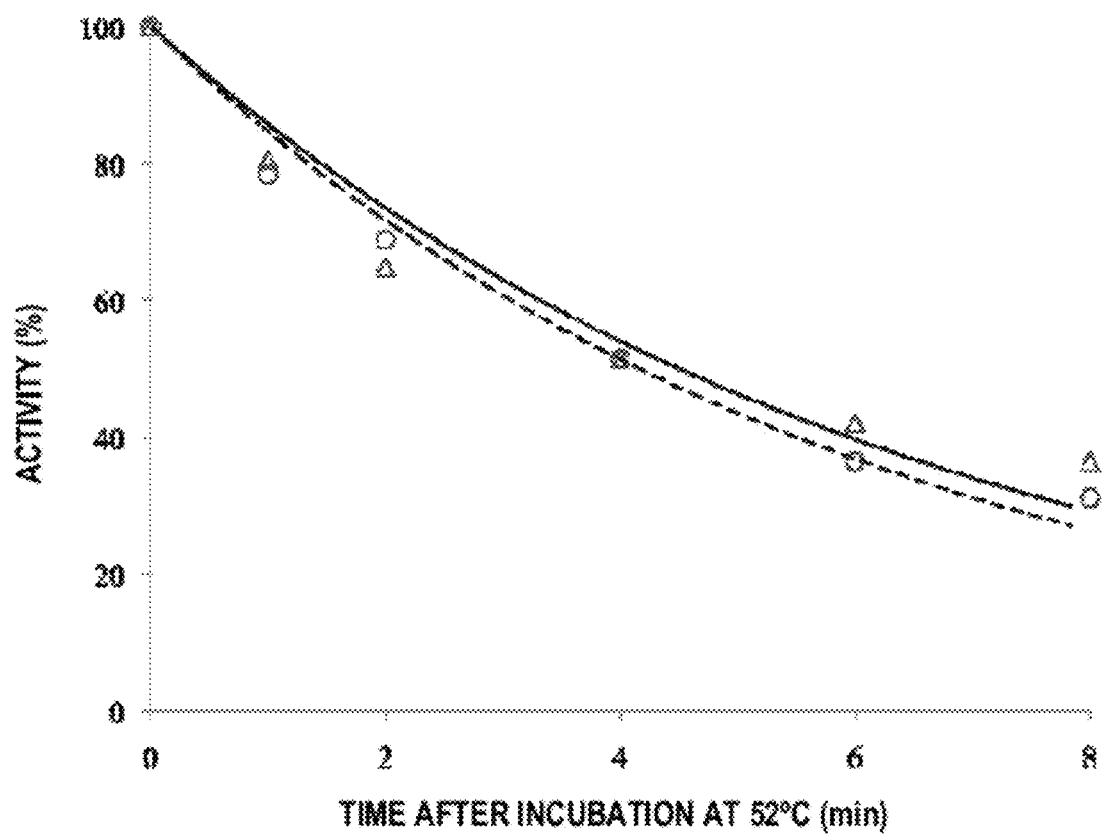

Similar reconstitution experiments were performed using the A3C1 subunit derived from the C2 domain-deleted factor VIII variant. The rationale for this experiment was that if the enhanced stability of the Ala108Ile A1 were due to interaction with the C2 domain following reassociation with A3C1C2, then use of the truncated A3C1 for reconstitution would abrogate the enhanced stability of the variant. Experiments performed with a C2-domain deleted factor VIII, described in an earlier report (Wakabayashi et al., "Factor VIII Lacking the C2 Domain Retains Cofactor Activity in vitro," *J. Biol. Chem* 285:25176-25184 (2010), which is hereby incorporated by reference in its entirety), showed that this variant was marked less stable than WT factor VIII at elevated temperatures and rates of decay needed to be monitored at a relatively lower temperature (52° C.). Under these conditions, the C2-domain deleted factor VIII variant decayed ~40-fold faster than WT factor VIII. For this reason, stability studies following factor VIII reconstitutions with the A3C1 light chain were performed at 52° C. Furthermore, in an earlier study (Wakabayashi et al., "Generation of Enhanced Stability Factor VIII Variants by Replacement of Charged Residues at the A2 Domain Interface," *Blood* 112:2761-2769 (2008), which is hereby incorporated by reference in its entirety), it was demonstrated that factor VIII stability measured over a range of temperatures from 52-60° C. yielded similar relative rates of decay when comparing a given factor VIII variant to WT. Consistent with observations using the C2 domain-deleted factor VIII, reconstitutions using either A1 form with A3C1 were observed to yield an overall faster decay (FIG. 7B), with ~50% activity reduction at 4 min at 52° C., than results observed following reconstitutions with the intact A3C1C2. The estimated decay rates for WT and the variant factor VIIIa forms were similar (0.166±0.001 and 0.154±0.013 min$^{-1}$, respectively). That the observed increase in thermal stability of the Ala108Ile variant was also observed following reconstitutions using purified components supports the conclusion that the enhanced stability of the variant as compared with WT derived from improved interaction(s) between A1 and A3C1C2 subunits and required the presence of C2 subunit.

Discussion of Examples 1-5

The preceding Examples illustrate interactions at the interface between factor VIII A1 and C2 domains following preparation of two factor VIII variants, Arg121Cys/Leu2302Cys factor VIII, which possesses a nascent disulfide bond spanning these domains, and Ala108Ile factor VIII, which has a larger hydrophobic side chain to better fill the inter-domain space. Several other mutations were prepared at this region in an attempt to create a disulfide bond or to increase hydrophobicity. These variants yielded low specific activity values, possibly resulting from unfavorable changes in conformation, and their characterization was not pursued further. However, both variants studied exhibited enhanced inter-A1-C2 domain affinity resulting in increases in the observed stability of the factor VIII variants, especially related to thermal denaturation.

The intermediate resolution (~4 Å) X-ray structure of factor VIII (Ngo et al., "Crystal Structure of Human Factor VIII: Implications for the Formation of the Factor IXa:Factor VIIIa Complex," *Structure* 16:597-606 (2008), which is hereby incorporated by reference in its entirety) predicts the close proximity of Arg121 and Leu2302 with 7.7 Å separating Cα atoms (PDB#3CDZ). This spatial separation suggested the potential to bridge this distance by a disulfide bond (~4-6 Å) following replacement of these residues with Cys, and provided that the side chains were in an acceptable orientation. Results evaluating the Arg121Cys/Leu2302Cys factor VIII protein by western blotting in the absence and presence of disulfide bond reduction showed high efficiency bridging (>90%) constituting experimental proof for the opposing orientation of side chains of these two residues in factor VIII. In addition, the X-ray structure also showed that the A1-C2 junction adjacent to Ala108 is rich in hydrophobic groups represented by the Cβ carbon of Ala108 from the Cδ of Leu2302, the Cβ of Ala2328, or the Cγ of Gln2329 (see FIG. 3C). Thus, it was believed that extended alkyl groups of side chains larger than the methyl group of Ala might contribute to enhanced binding energy. Of several variants prepared to this region, replacement of Ala108 with Ile yielded a variant possessing near WT-like specific activity.

Both Arg121Cys/Leu2302Cys and Ala108Ile variants exhibited superior stability parameters as compared with the WT protein. For example, the thermal decay rates for the Arg121Cys/Leu2302Cys and Ala108Ile factor VIII variants were reduced by 3.1- and 4.2-fold, respectively, as compared with WT. Further dissection of the interaction with the Ala108Ile variant was obtained following reconstitution of the A1/A3C1C2 dimer using WT and variant A1 subunits as well as the truncated A3C1 subunit derived from the C2 domain-deleted factor VIII. Enhanced stability of the variant compared with WT was observed using native A3C1C2, but similar stability parameter values for variant and WT were observed even in the absence of the C2 domain. Taken together, these observations support the belief that modulating the A1-C2 interface, either through covalent bridging or increased hydrophobic interaction, appeared to make an important contribution to overall protein stability.

The primary cause for thermal decay of FVIII is attributed to dissociation of the heavy and light chains (Ansong et al., "Factor VIII A3 Domain Residues 1954-1961 Represent an A1 Domain-Interactive Site," *Biochemistry* 44:8850-8857 (2005), which is hereby incorporated by reference in its entirety). This result is supported by the present study showing that bridging the factor VIII heavy chain and light chain via a disulfide bond between A1 and C2 domains preferentially reduced thermal decay as compared with chemical denaturation. Thus, chemical denaturation appears to represent a more global effect on factor VIII structure and less specific for chain dissociation. It was reported earlier that several residues at the A2-A3 interface (Tyr1792, Tyr1786 and Asp666) possibly contributed to the binding energy only in the active factor VIIIa form (Wakabayashi et al., "Identification of Residues Contributing to A2 Domain-dependent Structural Stability in Factor VIII and Factor VIIIa," *J. Biol. Chem* 283:11645-11651 (2008), which is hereby incorporated by reference in its entirety). Thus, interactions between the A2 domain of the heavy chain and A3C1C2 domains of the light chain may be minimal in the pro-cofactor. Based upon that earlier report and the present study, it is believed that in the factor VIII heterodimer, the predominant sources for binding energy likely derive from A1 interactions with both the A3 and C2 domains.

On the other hand, the instability of factor VIIIa results from weak electrostatic interactions between the A2 subunit and the A1/A3C1C2 dimer (Fay et al., "Human Factor VIIIa Subunit Structure: Reconstitution of Factor VIIIa from the Isolated A1/A3-C1-C2 Dimer and A2 Subunit," *J. Biol. Chem* 266:8957-8962 (1991); Lollar et al., "pH-dependent Denaturation of Thrombin-activated Porcine Factor VIII," *J. Biol. Chem* 265:1688-1692 (1990), each of which is hereby incorporated by reference in its entirety) and its dissociation leads to dampening of factor Xase activity (Lollar et al., "Coagulant Properties of Hybrid Human/Porcine Factor VIII Molecules," *J. Biol. Chem* 267:23652-23657 (1992); Fay et al., "Model for the Factor VIIIa-dependent Decay of the Intrinsic Factor Xase: Role of Subunit Dissociation and Factor IXa-catalyzed Proteolysis," *J. Biol. Chem* 271:6027-6032 (1996), each of which is hereby incorporated by reference in its entirety). Several factor VIII point mutations have been shown to facilitate the rate of dissociation of A2 relative to wild type (WT) and these residues localize to either the A1-A2 domain interface (Pipe et al., "Mild Hemophilia A Caused by Increased Rate of Factor VIII A2 Subunit Dissociation: Evidence for Nonproteolytic Inactivation of Factor VIIIa in vivo," *Blood* 93:176-183 (1999); Pipe et al., "Hemophilia A Mutations Associated with 1-stage/2-stage Activity Discrepancy Disrupt Protein-protein Interactions within the Triplicated A Domains of Thrombin-activated Factor VIIIa," *Blood* 97:685-691 (2001), each of which is hereby incorporated by reference in its entirety) or the A1 and C2 domains (Hakeos et al., "Hemophilia A Mutations Within the Factor VIII A2-A3 Subunit Interface Destabilize Factor VIIIa and Cause One-Stage/Two-Stage Activity Discrepancy," *Thromb. Haemost* 88: 781-787 (2002), which is hereby incorporated by reference in its entirety). In U.S. Patent Application Publ. No. 20090118184 to Fay et al., which is hereby incorporated by reference in its entirety, it was demonstrated that replacing the charged residues Asp519, Glu665, and Glu1984 with Ala or Val yielded increased factor VIII stability and in particular enhanced retention of the A2 subunit in factor VIIIa. Interestingly, neither the single mutants nor combinations of these mutations yielded factor VIII variants that showed reductions in the rate of thermal decay of greater than 2.3-fold, whereas the variants examined in the present study showed thermal decay rate reductions of 3- to 4-fold. Thus, the magnitude of stability enhancement observed for the A1-C2 interface variants appears somewhat larger than for the A2 domain-mediated interactions. However, while these variants clearly showed superior factor VIII stability, results from this study indicated essentially little if any effect of the interactions involving the A1 and C2 domains in stabilizing the factor VIIIa cofactor, suggesting no linkage of these sites with sites involved in A2 subunit retention. For this reason, it is the combinations of these A1-C2 domain stabilizing mutations with A1-A2 or A3-A2 domain stabilizing mutations that appear to be most desirable.

A1 domain residues 110-126 are in close contact to the C2 domain. These residues contain a $Ca^{2+}$ binding site predicted by Ala-scanning mutagenesis (Wakabayashi et al., "Residues 110-126 in the A1 Domain of Factor VIII Contain a $Ca^{2+}$ Binding Site Required for Cofactor Activity," *J. Biol. Chem* 279:12677-12684 (2004), which is hereby incorporated by reference in its entirety) and subsequently identified in the X-ray crystal structure (Shen et al., "The Tertiary Structure and Domain Organization of Coagulation Factor VIII," *Blood* 111:1240-1247 (2008); Ngo et al., "Crystal Structure of Human Factor VIII: Implications for the Formation of the Factor IXa:Factor VIIIa Complex," *Structure* 16:597-606 (2008), each of which is hereby incorporated by reference in its entirety). Interestingly, preliminary experiments assessing chelation of $Ca^{2+}$ (and/or $Cu^{2+}$) in factor VIII by EGTA yielded dramatic losses in activity of WT factor VIII while showing more minimal effects on the activity of Arg121Cys/Leu2302Cys and Ala108Ile variants. Without being bound by belief, it is believed the functional effects of $Ca^{2+}$ occupancy at 110-126 in factor VIII were replaced by enhanced stabilizing interactions between the A1 and C2 domains in the variants.

In conclusion, results from Examples 1-5 demonstrate that interactions between the A1 and C2 domains of factor VIII contribute to the integrity of the protein, providing significant energy for stabilizing the multi-domain structure of factor VIII. Furthermore, observations for enhancing factor VIII stability, in particular by increasing non-covalent, hydrophobic interactions at the A1-C2 domain interface suggests that these variants could potentially represent superior therapeutics in the treatment of hemophilia.

Example 6

Combination of R121C/L2302C or Ala108Ile Substitution with One or More Substitutions at the A1-A2 or A2-A3 Domain Interfaces Based on the improved thermal and/or chemical stability afforded by the A1-C2 variants, it was also determined whether the mutations at the A1-C2 interface can be combined with the mutation at one of the A1-A2 or A2-A3 interfaces to generate a factor VIII with even greater stability. Previously tested stable factor VIII mutants, as described in U.S. Patent Application Publ. No. 2009/0118184 to Fay et al., which is hereby incorporated by reference in its entirety, showed up to 2-fold increases in thermal stability compared with WT factor VIII in any combination of the mutation with Asp519Ala, Asp519Val, Glu665Ala, Glu665Val, Glu1984Ala, and Glu1984Val (A1-A2 or A2-A3 domain mutants).

Figure 8A:
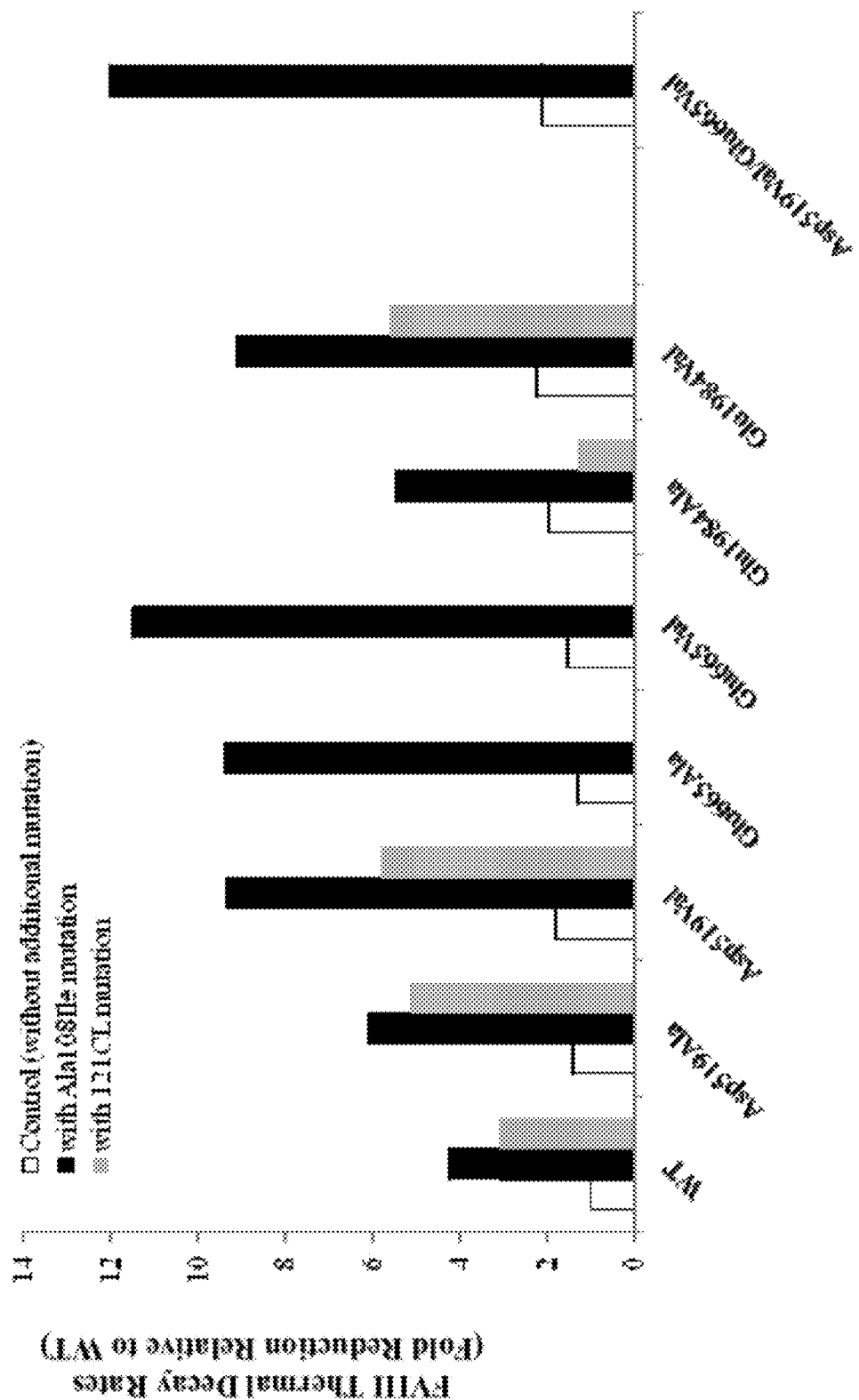
Figure 8B:
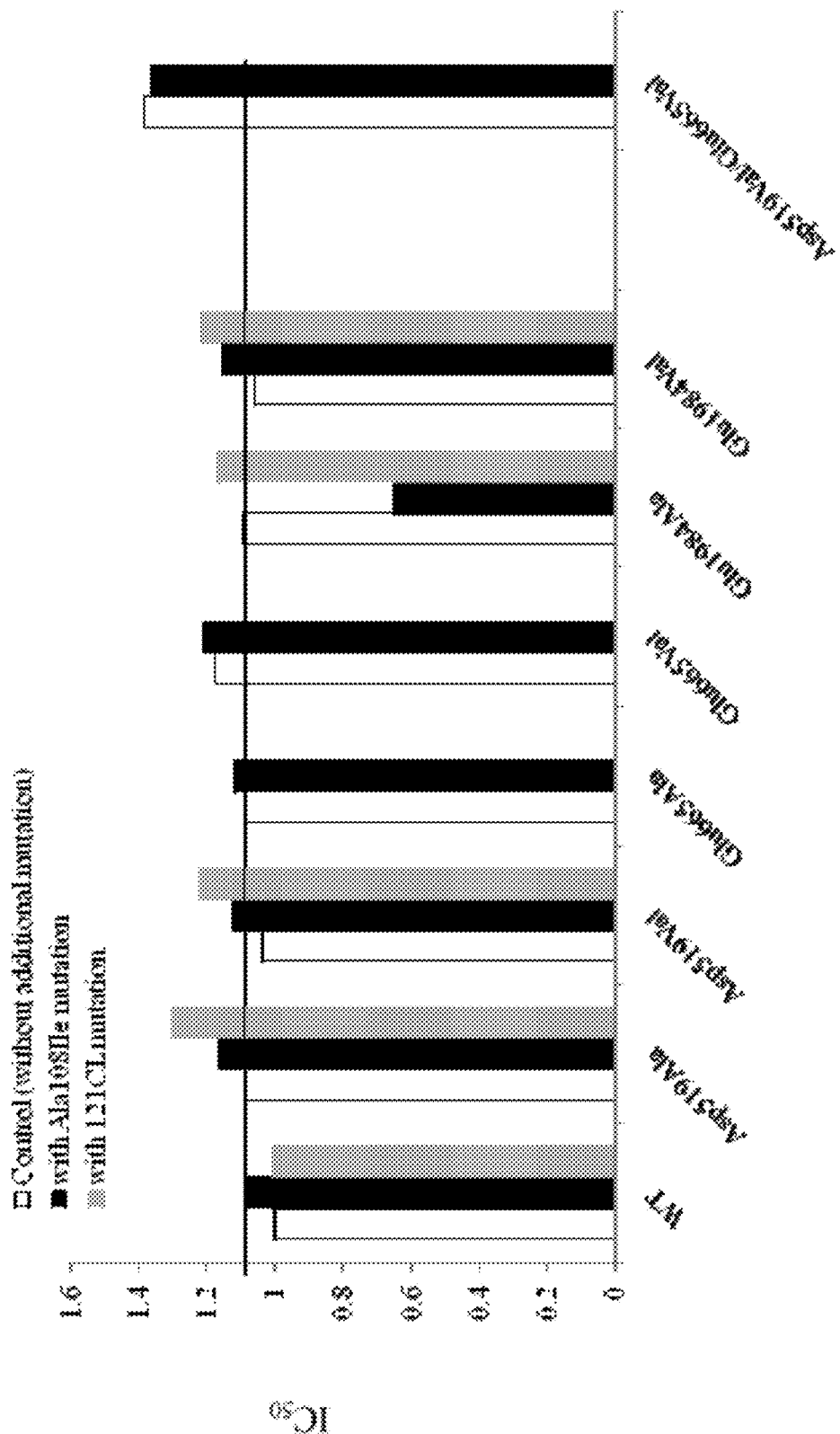
Figure 8C:
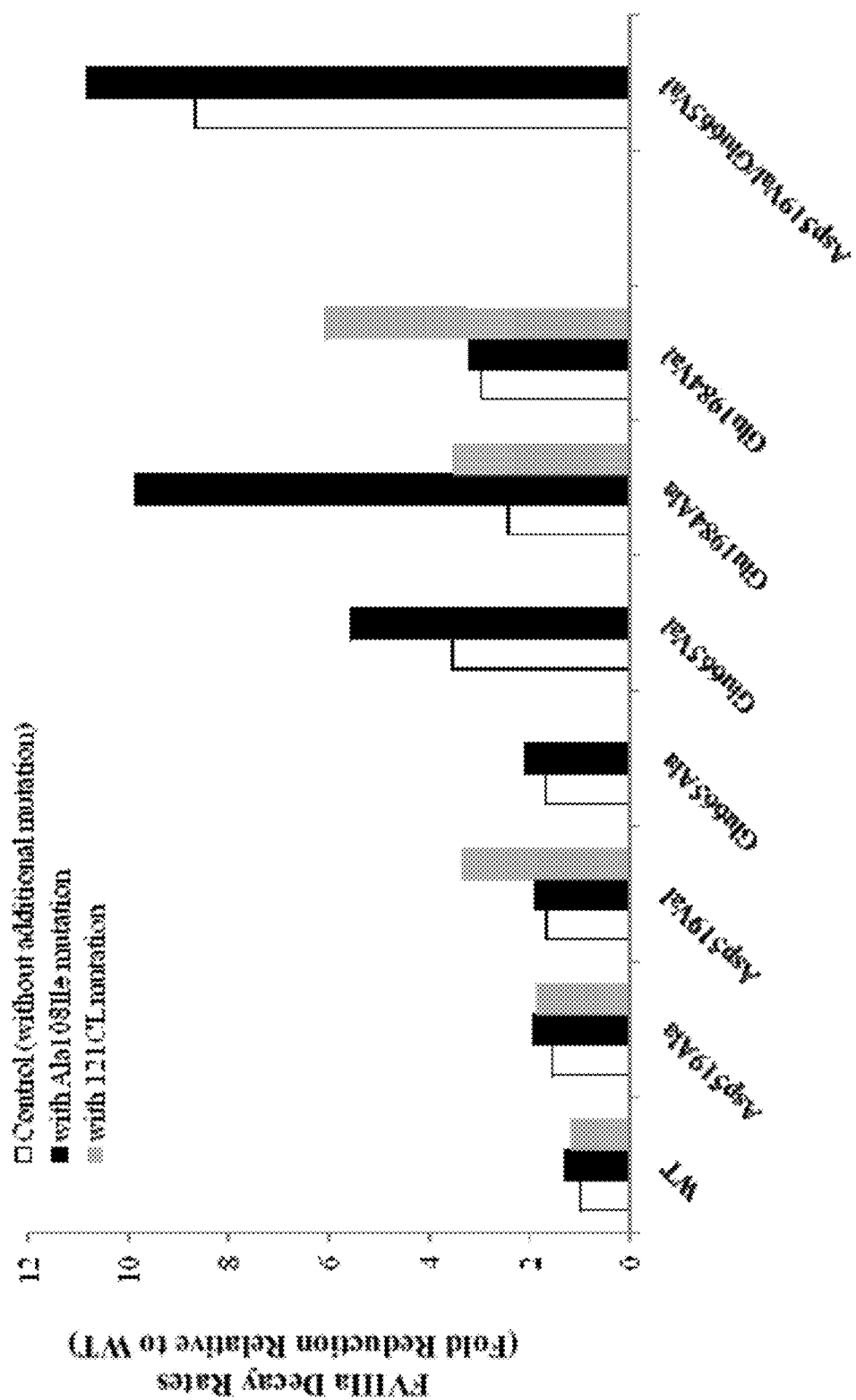

These single point mutations or the double mutation Asp519Val/Glu665Val were combined with either R121C/L2302C or Ala108Ile in a B-domainless factor VIII cDNA using the procedures described in Example 1. These factor VIII mutants were expressed and purified using the procedures described in Example 1. Specific activity values showed that most of the mutants (10 out of 13) showed normal factor VIII activity values (>60% WT) as measured by factor Xa generation assay (see Table 2 below). Thermal stability values were determined as described above in Example 4. Many of the resulting mutants exhibited >5 fold increase in thermal stability (10/13 mutants, FIG. 8A), with Ala108Ile/Glu665Val and Ala108Ile/Asp519Val/Glu665Val being the most stable mutants (~10 fold increase relative to WT). Most of the mutants also showed 15-30% increases in $IC_{50}$ value (guanidinium experiment) compared with WT (FIG. 8B). In addition, the high factor VIIIa stability of the A domain mutants was mostly preserved (mutants (11/13) showed 2-10 fold increase in factor VIIIa stability relative to WT, FIG. 8C). Collectively, modification at the A1-C2 contacting region by covalent attachment or increasing hydrophobic interaction improved factor VIII stability and these modifications can be combined with A2 domain interface mutations to provide essentially additive effects compared with either type of mutation alone.

TABLE 2

Specific Activity of Factor VIII Variants

| FVIII variants | Activity (%) |
| --- | --- |
| WT | 100 |
| Ala108Ile | 73.7 |
| A108I/D519A | 77.7 |
| A108I/D519V | 69.5 |
| A108I/E665A | 98.8 |
| A108I/E665V | 83.8 |
| A108I/E1984A | 43.4 |
| A108I/E1984V | 94.1 |
| A108I/D519V/E665V | 76.5 |
| D519V/E665V | 90.0 |
| 121CL | 86.4 |
| 121CL/D519A | 60.7 |
| 121CL/D519V | 79.5 |
| 121CL/E665A | 0 |
| 121CL/E665V | 22.2 |
| 121CL/E1984A | 63.4 |
| 121CL/E1984V | 90.3 |

Activity was measured by FXa generation assay and expressed as relative values compared to WT activity. The single letter code is used to designate amino acid residues: I (Ile), E (Glu), D (Asp), A (Ala) and V (Val). The variant 121CL represents R121C/L2302C.

Figure 9:
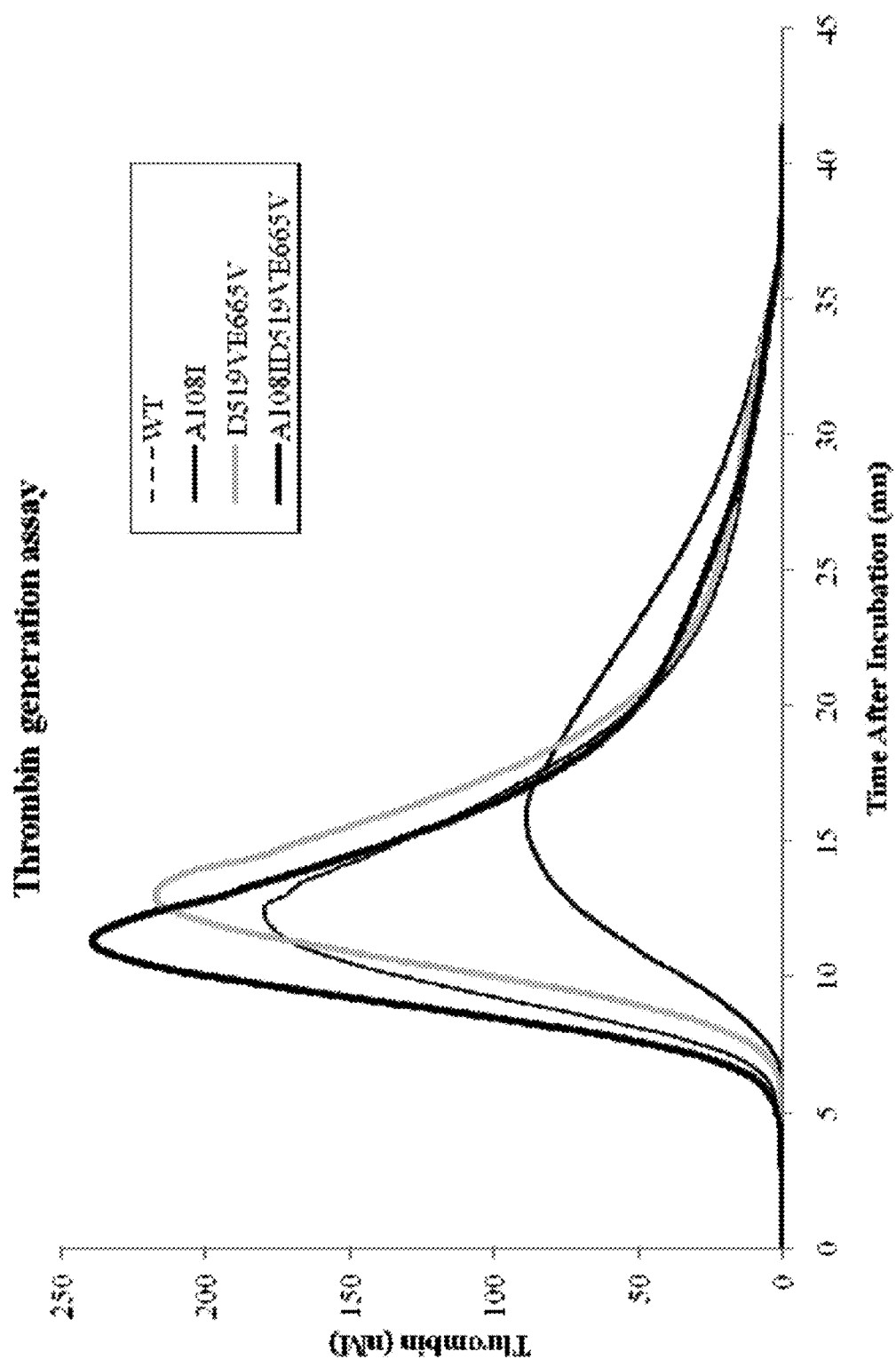
FIG. 9 is a graph comparing the effects of Ala108Ile, Asp519Val/Glu665Val, and the combined Ala108Ile/Asp519Val/Glu665Val variants, relative to wildtype, as measured using a thrombin generation assay.

Thrombin generation assays were performed as previously described (Wakabayashi et al., "Combining Mutations of Charged Residues at the A2 Domain Interface Enhances Factor VIII Stability over Single Point Mutations," *J. Thromb. Haemost.* 7:438-444 (2009), which is hereby incorporated by reference in its entirety) to determine the effects of combining the Ala108Ile mutation with an A2 domain interface mutation. For this analysis, the Asp519Val/Glu665Val double mutation was employed. Results in FIG. 9 compare WT factor VIII with Ala108Ile, Asp519Val/Glu665Val and the combined Ala108Ile/Asp519Val/Glu665Val variants. Both the Ala108Ile and the Asp519Val/Glu665Val variants showed improved thrombin generation parameter values compared with WT (see Table 3 below). In addition, the combined Ala108Ile/Asp519Val/Glu665Val mutation yielded somewhat greater thrombin peak values and endogenous thrombin potential ("ETP", which is the area under the curve and represents total thrombin generated) than either individual variant. This indicates a positive effect in combining these mutations.

TABLE 3

Thrombin Generation Assay Parameter Values

| FVIII variants | Latent Time (min) | Peak Time (min) | Peak Value (nM) | ETP (nM · min) |
|---|---|---|---|---|
| WT | 7.59 ± 0.09 (1.00) | 16.1 ± 0.22 (1.00) | 88.2 ± 6.60 (1.00) | 1217 ± 34 (1.00) |
| A108I | 7.09 ± 0.41 (0.93) | 12.7 ± 0.56 (0.79) | 175.3 ± 17.0 (1.98) | 1831 ± 183 (1.50) |
| D519V/E665V | 8.19 ± 0.18 (1.07) | 13.4 ± 0.16 (0.83) | 203.4 ± 18.2 (2.30) | 1939 ± 251 (1.59) |
| A108I/D519V/E665V | 7.05 ± 0.27 (0.92) | 11.9 ± 0.31 (0.73) | 222.8 ± 10.7 (2.52) | 1990 ± 122 (1.64) |

Thrombin generation assays in the presence of 0.5 nM factor VIII proteins, 0.5 Pm rTF, and 4 μM PSPCPE vesicles were performed and parameter values were calculated. Data represents the average values of triplicate samples. Values in parentheses are relative to the WT value. The single letter code is used to designate amino acid residues: I (Ile), E (Glu), D (Asp), A (Ala) and V (Val).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A The recombinant factor VIII comprising one or more mutations at an interface of A1 and C2 domains of recombinant factor VIII that result in enhanced stability of factor VIII, wherein the one or more mutations comprise substitution of one or more amino acid residues with an amino acid residue having a higher hydrophobicity, and wherein the A1 domain of the recombinant factor VIII comprises a C2 domain interface having the amino acid sequence of KXS (SEQ ID NO: 19) wherein the second residue is Valine, Isoleucine, or Leucine.

2. The recombinant factor VIII according to claim 1 further comprising a Glu→Ala substitution corresponding to position 113 of SEQ ID NO: 2.

3. The recombinant factor VIII according to claim 1, wherein the recombinant factor VIII is substantially pure.

4. The recombinant factor VIII according to claim 1, wherein the recombinant factor VIII further comprises one or more of (i) factor IXa and/or factor X binding domains modified to enhance the affinity of the recombinant factor VIII for one or both of factor IXa and factor X; (ii) modified sites that enhance secretion in culture; (iii) modified serum protein binding sites that enhance the circulating half-life thereof; (iv) at least one glycosylation recognition sequence that is effective in decreasing antigenicity and/or immunogenicity thereof;
  (v) a modified A1 domain calcium-binding site that improves specific activity of the recombinant factor VIIIa; (vi) modified activated protein C-cleavage site; (vii) a modified A1 and A2 domain interface; and (viii) a modified A2 and A3 domain interface.

5. The recombinant factor VIII according to claim 1, wherein the one or more mutations further comprise substitution of one or more charged amino acid residues with a hydrophobic amino acid residue at the A1 and A2 domain interface and/or A2 and A3 domain interface.

6. The recombinant factor VIII according to claim 5, wherein the charged amino acid residue at the A1 and A2 domain interface and/or A2 and A3 domain interface is either Glu or Asp, and the hydrophobic amino acid substitution at the A1 and A2 domain interface and/or A2 and A3 domain interface is one of Ala, Val, Ile, Leu, Met, Phe, or Trp.

7. The recombinant factor VIII according to claim 6, wherein the one or more mutations comprises a substitution of a Glu287 residue of wild type factor VIII, a substitution of an Asp302 residue of wild type factor VIII, a substitution of an Asp519 residue of wild type factor VIII, a substitution of a Glu665 residue of wild type factor VIII, a substitution of a Glu1984 residue of wild type factor VIII, or combinations thereof.

8. The recombinant factor VIII according to claim 7, wherein the one or more mutations comprise (i) an Asp→Ala substitution at a position corresponding to residue 302 of SEQ ID NO: 2; (ii) a Glu→Ala substitution at a position corresponding to residue 287 of SEQ ID NO: 2; (iii) a Glu→Ala or Glu→Val substitution at a position corresponding to residue 665 of SEQ ID NO: 2; (iv) a Asp→Ala or Asp→Val substitution at a position corresponding to residue 519 of SEQ ID NO: 2; (v) a Glu→Ala or Glu→Val substitution at a position corresponding to residue 1984 of SEQ ID NO: 2; or (vi) combinations of any two or more of the substitutions (i)-(v).

9. A pharmaceutical composition comprising the recombinant factor VIII according to claim 1.

10. A method of treating an animal for hemophilia A comprising:

administering to an animal exhibiting hemophilia A an effective amount of the recombinant factor VIII according to claim 1, whereby the animal exhibits effective blood clotting following vascular injury.

* * * * *

UNITED STATES PATENT AND TRADEMARK OFFICE
CERTIFICATE OF CORRECTION

| | | |
|---|---|---|
| PATENT NO. | : 8,637,448 B2 | Page 1 of 1 |
| APPLICATION NO. | : 13/231948 | |
| DATED | : January 28, 2014 | |
| INVENTOR(S) | : Fay et al. | |

It is certified that error appears in the above-identified patent and that said Letters Patent is hereby corrected as shown below:

In the Claims:

In claim 1, at col. 83, line 58, delete "The".

Signed and Sealed this
Sixth Day of May, 2014

Michelle K. Lee
*Deputy Director of the United States Patent and Trademark Office*

SEQUENCE LISTING

<160> NUMBER OF SEQ ID NOS: 34

<210> SEQ ID NO 1
<211> LENGTH: 6999
<212> TYPE: DNA
<213> ORGANISM: Human

<400> SEQUENCE: 1

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggatca cctttcaac      180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg gagccctact agtatgtaga     540
gaagggagtc tggccaagga aaagacacag accttgcaca aatttatact acttttgct      600
gtatttgatg aaggaaaag ttggcactca gaaacaaaga actccttgat gcaggatagg     660
gatgctgcat ctgctcggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct gtgaggaac      840
catcgccagg cgtccttgga aatctcgcca ataactttcc ttactgctca aacactcttg     900
atggaccttg gacagtttct actgttttgt catatctctt cccaccaaca tgatggcatg     960
gaagcttatg tcaaagtaga cagctgtcca gaggaacccc aactacgaat gaaaaataat    1020
gaagaagcgg aagactatga tgatgatctt actgattctg aaatggatgt ggtcaggttt    1080
gatgatgaca ctctccttc ctttatccaa attcgctcag ttgccaagaa gcatcctaaa    1140
acttgggtac attacattgc tgctgaagag gaggactggg actatgctcc cttagtcctc    1200
gcccccgatg acagaagtta taaaagtcaa tatttgaaca atggccctca gcggattggt    1260
aggaagtaca aaaaagtccg atttatggca tacacagatg aaacctttaa gactcgtgaa    1320
```

```
gctattcagc atgaatcagg aatcttggga cctttacttt atggggaagt tggagacaca    1380
ctgttgatta tatttaagaa tcaagcaagc agaccatata acatctaccc tcacggaatc    1440
actgatgtcc gtcctttgta ttcaaggaga ttaccaaaag gtgtaaaaca tttgaaggat    1500
tttccaattc tgccaggaga aatattcaaa tataaatgga cagtgactgt agaagatggg    1560
ccaactaaat cagatcctcg gtgcctgacc cgctattact ctagtttcgt taatatggag    1620
agagatctag cttcaggact cattggccct ctcctcatct gctacaaaga atctgtagat    1680
caaagaggaa accagataat gtcagacaag aggaatgtca tcctgttttc tgtatttgat    1740
gagaaccgaa gctggtacct cacagagaat atacaacgct ttctcccaa tccagctgga     1800 gtgcagcttg aggatccaga gttccaagcc tccaacatca tgcacagcat caatggctat    1860
gtttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg gggtgccaca actcagactt cggaacagaa    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
agcttctccc agaattcaag acaccctagc actaggcaaa agcaatttaa tgccaccaca    2280
attccagaaa atgacataga gaagactgac ccttggtttg cacacagaac acctatgcct    2340
aaaatacaaa atgtctcctc tagtgatttg ttgatgctct gcgacagag tcctactcca    2400 catgggctat ccttatctga tctccaagaa gccaaatatg agactttttc tgatgatcca    2460
tcacctggag caatagacag taataacagc ctgtctgaaa tgacacactt caggccacag    2520
ctccatcaca gtggggacat ggtatttacc cctgagtcag gcctccaatt aagattaaat    2580
gagaaactgg ggacaactgc agcaacagag ttgaagaaac ttgatttcaa agtttctagt    2640
acatcaaata atctgattt caacaattcca tcagacaatt tggcagcagg tactgataat    2700
acaagttcct taggacccc aagtatgcca gttcattatg atagtcaatt agataccact    2760
ctatttggca aaaagtcatc tccccttact gagtctggtg gacctctgag cttgagtgaa    2820
gaaaataatg attcaaagtt gttagaatca ggtttaatga atagccaaga aagttcatgg    2880
ggaaaaaatg tatcgtcaac agagagtggt aggttattta aagggaaaag agctcatgga    2940
cctgctttgt tgactaaaga taatgcctta ttcaaagtta gcatctcttt gttaaagaca    3000
aacaaaactt ccaataattc agcaactaat agaaagactc acattgatgg cccatcatta    3060
ttaattgaga atagtccatc agtctggcaa aatatattag aaagtgacac tgagtttaaa    3120
aaagtgacac ctttgattca tgacagaatg cttatggaca aaaatgctac agctttgagg    3180
ctaaatcata tgtcaaataa aactacttca tcaaaaaaca tggaaatggt ccaacagaaa    3240
aaagagggcc ccattccacc agatgcacaa aatccagata tgtcgttctt aagatgcta     3300 ttcttgccag aatcagcaag gtggatacaa aggactcatg gaaagaactc tctgaactct    3360
gggcaaggcc ccagtccaaa gcaattagta tccttaggac cagaaaaatc tgtggaaggt    3420
cagaatttct tgtctgagaa aaacaaagtg gtagtaggaa agggtgaatt tacaaaggac    3480
gtaggactca aagagatggt ttttccaagc agcagaaacc tatttcttac taacttggat    3540
aatttacatg aaaataatac acacaatcaa gaaaaaaaaa ttcaggaaga aatagaaaag    3600
aaggaaacat taatccaaga gaatgtagtt ttgcctcaga tacatacagt gactggcact    3660
aagaatttca tgaagaacct tttcttactg agcactaggc aaaatgtaga aggttcatat    3720
```

```
gacggggcat atgctccagt acttcaagat tttaggtcat taaatgattc aacaaataga    3780
acaaagaaac acacagctca tttctcaaaa aaggggagg aagaaaactt ggaaggcttg     3840
ggaaatcaaa ccaagcaaat tgtagagaaa tatgcatgca ccacaaggat atctcctaat   3900
acaagccagc agaattttgt cacgcaacgt agtaagagac ctttgaaaca attcagactc   3960
ccactagaag aaacagaact tgaaaaaagg ataattgtgg atgacacctc aacccagtgg   4020
tccaaaaaca tgaaacattt gaccccgagc accctcacac agatagacta caatgagaag   4080
gagaaagggg ccattactca gtctcccttta tcagattgcc ttacgaggag tcatagcatc   4140
cctcaagcaa atagatctcc attacccatt gcaaaggtat catcatttcc atctattaga   4200
cctatatatc tgaccagggt cctattccaa gacaactctt ctcatcttcc agcagcatct   4260
tatagaaaga aagattctgg ggtccaagaa agcagtcatt tcttacaagg agccaaaaaa   4320
aataaccttt ctttagccat tctaaccttg gagatgactg gtgatcaaag agaggttggc   4380
tccctgggga caagtgccac aaattcagtc acatacaaga agttgagaa cactgttctc     4440 ccgaaaccag acttgcccaa acatctggc aaagttgaat tgcttccaaa agttcacatt    4500
tatcagaagg acctattccc tacggaaact agcaatgggt ctcctggcca tctggatctc   4560
gtggaaggga gccttcttca gggaacagag ggagcgatta agtggaatga agcaaacaga   4620
cctgaaaaag ttccctttct gagagtagca acagaaagct ctgcaaagac tccctccaag    4680
ctattggatc ctcttgcttg ggataaccac tatggtactc agataccaaa agaagagtgg   4740
aaatcccaag agaagtcacc agaaaaaaca gctttttaaga aaaaggatac cattttgtcc   4800
ctgaacgctt gtgaaagcaa tcatgcaata gcagcaataa atgagggaca aaataagccc    4860
gaaatagaag tcacctgggc aaagcaaggt aggactgaaa ggctgtgctc tcaaaaccca    4920
ccagtcttga aacgccatca acgggaaata actcgtacta ctcttcagtc agatcaagag   4980
gaaattgact atgatgatac catatcagtt gaaatgaaga aggaagattt tgacattttat    5040 gatgaggatg aaaatcagag cccccgcagc tttcaaaaga aaacacgaca ctatttatt      5100 gctgcagtgg agaggctctg ggattatggg atgagtagct ccccacatgt tctaagaaac    5160
agggctcaga gtggcagtgt ccctcagttc aagaaagttg ttttccagga atttactgat    5220
ggctccttta ctcagccctt ataccgtgga gaactaaatg aacatttggg actcctgggg     5280
ccatatataa gagcagaagt tgaagataat atcatggtaa ctttcagaaa tcaggcctct    5340 cgtcccctatt ccttctattc tagcctttatt tcttatgagg aagatcagag gcaaggagca    5400
gaacctagaa aaaactttgt caagcctaat gaaaccaaaa cttactttg gaaagtgcaa     5460 catcatatgg cacccactaa agatgagttt gactgcaaag cctgggctta tttctctgat    5520
gttgacctgg aaaagatgt gcactcaggc ctgattggac cccttctggt ctgccacact     5580
aacacactga accctgctca tgggagacaa gtgacagtac aggaatttgc tctgtttttc    5640
accatctttg atgagaccaa aagctggtac ttcactgaaa atatgaaag aaactgcagg     5700 gctccctgca atatccagat ggaagatccc acttttaaag agaattatcg cttccatgca   5760
atcaatggct acataatgga tacactacct ggcttagtaa tggctcagga tcaaaggatt   5820
cgatggtatc tgctcagcat gggcagcaat gaaaacatcc attctattca tttcagtgga   5880
catgtgttca ctgtacgaaa aaaagaggag tataaaatgg cactgtacaa tctctatcca    5940 ggtgttttttg agacagtgga aatgttacca tccaaagctg gaatttggcg ggtggaatgc    6000
cttattggcg agcatctaca tgctgggatg agcacttttt ttctggtgta cagcaataag    6060
tgtcagactc ccctgggaat ggcttctgga cacattgagg attttcagat tacagcttca    6120
```

-continued

```
ggacaatatg gacagtgggc cccaaagctg ccagacttc attattccgg atcaatcaat    6180
gcctggagca ccaaggagcc cttttcttgg atcaaggtgg atctgttggc accaatgatt    6240
attcacggca tcaagaccca gggtgcccgt cagaagttct ccagcctcta catctctcag    6300
tttatcatca tgtatagtct tgatgggaag aagtggcaga cttatcgagg aaattccact    6360
ggaaccttaa tggtcttctt tggcaatgtg gattcatctg ggataaaaca caatattttt    6420
aaccctccaa ttattgctcg atacatccgt ttgcacccaa ctcattatag cattcgcagc    6480
actcttcgca tggagttgat gggctgtgat ttaaatagtt gcagcatgcc attgggaatg    6540
gagagtaaag caatatcaga tgcacagatt actgcttcat cctactttac caatatgttt    6600
gccacctggt ctccttcaaa agctcgactt cacctccaag ggaggagtaa tgcctggaga    6660
cctcaggtga ataatccaaa agagtggctg caagtggact tccagaagac aatgaaagtc    6720
acaggagtaa ctactcaggg agtaaaatct ctgcttacca gcatgtatgt gaaggagttc    6780
ctcatctcca gcagtcaaga tggccatcag tggactctct tttttcagaa tggcaaagta    6840 aaggttttc agggaaatca agactccttc acacctgtgg tgaactctct agacccaccg    6900
ttactgactc gctaccttcg aattcacccc cagagttggg tgcaccagat tgccctgagg    6960
atggaggttc tgggctgcga ggcacaggac ctctactga                           6999
```

<210> SEQ ID NO 2
<211> LENGTH: 2332
<212> TYPE: PRT
<213> ORGANISM: Human

<400> SEQUENCE: 2

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220
```

```
Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
        260                 265                 270

Gly His Thr Phe Leu Val Arg Asn His Arg Gln Ala Ser Leu Glu Ile
    275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655
```

```
Thr Phe Lys His Lys Met Val Tyr Glu Asp Thr Leu Thr Leu Phe Pro
        660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
                740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
        770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
        850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
        930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
        1010                1015                1020

Asn Ser Pro Ser Val Trp Gln Asn Ile Leu Glu Ser Asp Thr Glu
        1025                1030                1035

Phe Lys Lys Val Thr Pro Leu Ile His Asp Arg Met Leu Met Asp
        1040                1045                1050

Lys Asn Ala Thr Ala Leu Arg Leu Asn His Met Ser Asn Lys Thr
        1055                1060                1065

Thr Ser Ser Lys Asn Met Glu Met Val Gln Gln Lys Lys Glu Gly
```

|  |  |  |  |  |  |  |  |  |  |
|---|---|---|---|---|---|---|---|---|---|
| 1070 | | | | 1075 | | | | 1080 | |
| Pro | Ile | Pro | Pro | Asp | Ala | Gln | Asn | Pro | Asp | Met | Ser | Phe | Phe | Lys |
| 1085 | | | | 1090 | | | | 1095 | |
| Met | Leu | Phe | Leu | Pro | Glu | Ser | Ala | Arg | Trp | Ile | Gln | Arg | Thr | His |
| 1100 | | | | 1105 | | | | 1110 | |
| Gly | Lys | Asn | Ser | Leu | Asn | Ser | Gly | Gln | Gly | Pro | Ser | Pro | Lys | Gln |
| 1115 | | | | 1120 | | | | 1125 | |
| Leu | Val | Ser | Leu | Gly | Pro | Glu | Lys | Ser | Val | Glu | Gly | Gln | Asn | Phe |
| 1130 | | | | 1135 | | | | 1140 | |
| Leu | Ser | Glu | Lys | Asn | Lys | Val | Val | Gly | Lys | Gly | Glu | Phe | Thr |
| 1145 | | | | 1150 | | | | 1155 | |
| Lys | Asp | Val | Gly | Leu | Lys | Glu | Met | Val | Phe | Pro | Ser | Ser | Arg | Asn |
| 1160 | | | | 1165 | | | | 1170 | |
| Leu | Phe | Leu | Thr | Asn | Leu | Asp | Asn | Leu | His | Glu | Asn | Asn | Thr | His |
| 1175 | | | | 1180 | | | | 1185 | |
| Asn | Gln | Glu | Lys | Lys | Ile | Gln | Glu | Glu | Ile | Glu | Lys | Lys | Glu | Thr |
| 1190 | | | | 1195 | | | | 1200 | |
| Leu | Ile | Gln | Glu | Asn | Val | Val | Leu | Pro | Gln | Ile | His | Thr | Val | Thr |
| 1205 | | | | 1210 | | | | 1215 | |
| Gly | Thr | Lys | Asn | Phe | Met | Lys | Asn | Leu | Phe | Leu | Leu | Ser | Thr | Arg |
| 1220 | | | | 1225 | | | | 1230 | |
| Gln | Asn | Val | Glu | Gly | Ser | Tyr | Glu | Gly | Ala | Tyr | Ala | Pro | Val | Leu |
| 1235 | | | | 1240 | | | | 1245 | |
| Gln | Asp | Phe | Arg | Ser | Leu | Asn | Asp | Ser | Thr | Asn | Arg | Thr | Lys | Lys |
| 1250 | | | | 1255 | | | | 1260 | |
| His | Thr | Ala | His | Phe | Ser | Lys | Lys | Gly | Glu | Glu | Glu | Asn | Leu | Glu |
| 1265 | | | | 1270 | | | | 1275 | |
| Gly | Leu | Gly | Asn | Gln | Thr | Lys | Gln | Ile | Val | Glu | Lys | Tyr | Ala | Cys |
| 1280 | | | | 1285 | | | | 1290 | |
| Thr | Thr | Arg | Ile | Ser | Pro | Asn | Thr | Ser | Gln | Gln | Asn | Phe | Val | Thr |
| 1295 | | | | 1300 | | | | 1305 | |
| Gln | Arg | Ser | Lys | Arg | Ala | Leu | Lys | Gln | Phe | Arg | Leu | Pro | Leu | Glu |
| 1310 | | | | 1315 | | | | 1320 | |
| Glu | Thr | Glu | Leu | Glu | Lys | Arg | Ile | Ile | Val | Asp | Asp | Thr | Ser | Thr |
| 1325 | | | | 1330 | | | | 1335 | |
| Gln | Trp | Ser | Lys | Asn | Met | Lys | His | Leu | Thr | Pro | Ser | Thr | Leu | Thr |
| 1340 | | | | 1345 | | | | 1350 | |
| Gln | Ile | Asp | Tyr | Asn | Glu | Lys | Glu | Lys | Gly | Ala | Ile | Thr | Gln | Ser |
| 1355 | | | | 1360 | | | | 1365 | |
| Pro | Leu | Ser | Asp | Cys | Leu | Thr | Arg | Ser | His | Ser | Ile | Pro | Gln | Ala |
| 1370 | | | | 1375 | | | | 1380 | |
| Asn | Arg | Ser | Pro | Leu | Pro | Ile | Ala | Lys | Val | Ser | Ser | Phe | Pro | Ser |
| 1385 | | | | 1390 | | | | 1395 | |
| Ile | Arg | Pro | Ile | Tyr | Leu | Thr | Arg | Val | Leu | Phe | Gln | Asp | Asn | Ser |
| 1400 | | | | 1405 | | | | 1410 | |
| Ser | His | Leu | Pro | Ala | Ala | Ser | Tyr | Arg | Lys | Lys | Asp | Ser | Gly | Val |
| 1415 | | | | 1420 | | | | 1425 | |
| Gln | Glu | Ser | Ser | His | Phe | Leu | Gln | Gly | Ala | Lys | Lys | Asn | Asn | Leu |
| 1430 | | | | 1435 | | | | 1440 | |
| Ser | Leu | Ala | Ile | Leu | Thr | Leu | Glu | Met | Thr | Gly | Asp | Gln | Arg | Glu |
| 1445 | | | | 1450 | | | | 1455 | |
| Val | Gly | Ser | Leu | Gly | Thr | Ser | Ala | Thr | Asn | Ser | Val | Thr | Tyr | Lys |
| 1460 | | | | 1465 | | | | 1470 | |

```
Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875
```

```
Phe Phe Thr Ile Phe Asp Glu Thr Lys Ser Trp Tyr Phe Thr Glu
        1880                1885                1890

Asn Met Glu Arg Asn Cys Arg Ala Pro Cys Asn Ile Gln Met Glu
        1895                1900                1905

Asp Pro Thr Phe Lys Glu Asn Tyr Arg Phe His Ala Ile Asn Gly
        1910                1915                1920

Tyr Ile Met Asp Thr Leu Pro Gly Leu Val Met Ala Gln Asp Gln
        1925                1930                1935

Arg Ile Arg Trp Tyr Leu Leu Ser Met Gly Ser Asn Glu Asn Ile
        1940                1945                1950

His Ser Ile His Phe Ser Gly His Val Phe Thr Val Arg Lys Lys
        1955                1960                1965

Glu Glu Tyr Lys Met Ala Leu Tyr Asn Leu Tyr Pro Gly Val Phe
        1970                1975                1980

Glu Thr Val Glu Met Leu Pro Ser Lys Ala Gly Ile Trp Arg Val
        1985                1990                1995

Glu Cys Leu Ile Gly Glu His Leu His Ala Gly Met Ser Thr Leu
        2000                2005                2010

Phe Leu Val Tyr Ser Asn Lys Cys Gln Thr Pro Leu Gly Met Ala
        2015                2020                2025

Ser Gly His Ile Arg Asp Phe Gln Ile Thr Ala Ser Gly Gln Tyr
        2030                2035                2040

Gly Gln Trp Ala Pro Lys Leu Ala Arg Leu His Tyr Ser Gly Ser
        2045                2050                2055

Ile Asn Ala Trp Ser Thr Lys Glu Pro Phe Ser Trp Ile Lys Val
        2060                2065                2070

Asp Leu Leu Ala Pro Met Ile Ile His Gly Ile Lys Thr Gln Gly
        2075                2080                2085

Ala Arg Gln Lys Phe Ser Ser Leu Tyr Ile Ser Gln Phe Ile Ile
        2090                2095                2100

Met Tyr Ser Leu Asp Gly Lys Lys Trp Gln Thr Tyr Arg Gly Asn
        2105                2110                2115

Ser Thr Gly Thr Leu Met Val Phe Phe Gly Asn Val Asp Ser Ser
        2120                2125                2130

Gly Ile Lys His Asn Ile Phe Asn Pro Pro Ile Ile Ala Arg Tyr
        2135                2140                2145

Ile Arg Leu His Pro Thr His Tyr Ser Ile Arg Ser Thr Leu Arg
        2150                2155                2160

Met Glu Leu Met Gly Cys Asp Leu Asn Ser Cys Ser Met Pro Leu
        2165                2170                2175

Gly Met Glu Ser Lys Ala Ile Ser Asp Ala Gln Ile Thr Ala Ser
        2180                2185                2190

Ser Tyr Phe Thr Asn Met Phe Ala Thr Trp Ser Pro Ser Lys Ala
        2195                2200                2205

Arg Leu His Leu Gln Gly Arg Ser Asn Ala Trp Arg Pro Gln Val
        2210                2215                2220

Asn Asn Pro Lys Glu Trp Leu Gln Val Asp Phe Gln Lys Thr Met
        2225                2230                2235

Lys Val Thr Gly Val Thr Thr Gln Gly Val Lys Ser Leu Leu Thr
        2240                2245                2250

Ser Met Tyr Val Lys Glu Phe Leu Ile Ser Ser Ser Gln Asp Gly
        2255                2260                2265

His Gln Trp Thr Leu Phe Phe Gln Asn Gly Lys Val Lys Val Phe
```

-continued

```
                        2270                2275                2280

Gln Gly  Asn Gln Asp Ser  Phe Thr Pro Val Val Asn  Ser Leu Asp
    2285                 2290                 2295

Pro Pro  Leu Leu Thr Arg  Tyr Leu Arg Ile His Pro  Gln Ser Trp
    2300                 2305                 2310

Val His  Gln Ile Ala Leu  Arg Met Glu Val Leu Gly  Cys Glu Ala
    2315                 2320                 2325

Gln Asp  Leu Tyr
    2330

<210> SEQ ID NO 3
<211> LENGTH: 41
<212> TYPE: PRT
<213> ORGANISM: Porcine

<400> SEQUENCE: 3

Ala Val Gly Val Ser Phe Trp Lys Ser Ser Glu Gly Ala Glu Tyr Glu
1               5                   10                  15

Asp His Thr Ser Gln Arg Glu Lys Glu Asp Asp Lys Val Leu Pro Gly
            20                  25                  30

Lys Ser Gln Thr Tyr Val Trp Gln Val
        35                  40

<210> SEQ ID NO 4
<211> LENGTH: 41
<212> TYPE: PRT
<213> ORGANISM: Canine

<400> SEQUENCE: 4

Ala Val Gly Val Ser Tyr Trp Lys Ala Ser Glu Gly Ala Glu Tyr Glu
1               5                   10                  15

Asp Gln Thr Ser Gln Lys Glu Lys Glu Asp Asp Asn Val Ile Pro Gly
            20                  25                  30

Glu Ser His Thr Tyr Val Trp Gln Val
        35                  40

<210> SEQ ID NO 5
<211> LENGTH: 41
<212> TYPE: PRT
<213> ORGANISM: Mouse

<400> SEQUENCE: 5

Ala Val Gly Val Ser Tyr Trp Lys Ala Ser Glu Gly Asp Glu Tyr Glu
1               5                   10                  15

Asp Gln Thr Ser Gln Met Glu Lys Glu Asp Asp Lys Val Phe Pro Gly
            20                  25                  30

Glu Ser His Thr Tyr Val Trp Gln Val
        35                  40

<210> SEQ ID NO 6
<211> LENGTH: 41
<212> TYPE: PRT
<213> ORGANISM: Rabbit

<400> SEQUENCE: 6

Ala Val Gly Val Ser Tyr Trp Lys Ala Ser Glu Gly Ala Glu Tyr Asp
1               5                   10                  15

Asp Gln Thr Ser Gln Arg Glu Lys Glu Asp Asp Lys Ile Phe Pro Gly
            20                  25                  30

Glu Ser His Thr Tyr Val Trp Gln Val
```

<210> SEQ ID NO 7
<211> LENGTH: 41
<212> TYPE: PRT
<213> ORGANISM: Bat

<400> SEQUENCE: 7

Ala Val Gly Val Ser Tyr Trp Lys Ala Ser Glu Gly Ala Glu Tyr Glu
1               5                   10                  15

Asp Glu Thr Ser Lys Thr Glu Lys Glu Asp Asp Lys Val Ile Pro Gly
                20                  25                  30

Glu Ser His Thr Tyr Val Trp His Val
            35                  40

<210> SEQ ID NO 8
<211> LENGTH: 41
<212> TYPE: PRT
<213> ORGANISM: Rat

<400> SEQUENCE: 8

Ala Val Gly Met Ser Phe Trp Lys Ala Ser Glu Gly Ala Ala Tyr Asp
1               5                   10                  15

Asp His Ser Ser Pro Ala Glu Lys Asp Asp Asp Lys Val Leu Pro Gly
                20                  25                  30

Glu Ser His Thr Tyr Ala Trp Gln Val
            35                  40

<210> SEQ ID NO 9
<211> LENGTH: 41
<212> TYPE: PRT
<213> ORGANISM: Sheep

<400> SEQUENCE: 9

Ala Ile Gly Val Ser Tyr Trp Lys Ser Ser Gly Ala Ala Tyr Lys
1               5                   10                  15

Asp Glu Thr Ser Gln Arg Glu Lys Glu Asp Asp Lys Val Ile Pro Gly
                20                  25                  30

Lys Ser His Thr Tyr Val Trp His Ile
            35                  40

<210> SEQ ID NO 10
<211> LENGTH: 41
<212> TYPE: PRT
<213> ORGANISM: Artificial
<220> FEATURE:
<223> OTHER INFORMATION: Consensus
<220> FEATURE:
<221> NAME/KEY: MISC_FEATURE
<222> LOCATION: (2)..(2)
<223> OTHER INFORMATION: X at position 2 is I or V
<220> FEATURE:
<221> NAME/KEY: MISC_FEATURE
<222> LOCATION: (4)..(4)
<223> OTHER INFORMATION: X at position 4 is V or M
<220> FEATURE:
<221> NAME/KEY: MISC_FEATURE
<222> LOCATION: (6)..(6)
<223> OTHER INFORMATION: X at position 6 is Y or F
<220> FEATURE:
<221> NAME/KEY: MISC_FEATURE
<222> LOCATION: (9)..(9)
<223> OTHER INFORMATION: X at position 9 is S or A
<220> FEATURE:
<221> NAME/KEY: MISC_FEATURE
<222> LOCATION: (13)..(13)
<223> OTHER INFORMATION: X at position 13 is A or D

```
<220> FEATURE:
<221> NAME/KEY: MISC_FEATURE
<222> LOCATION: (14)..(14)
<223> OTHER INFORMATION: X at position 14 is A or E
<220> FEATURE:
<221> NAME/KEY: MISC_FEATURE
<222> LOCATION: (16)..(16)
<223> OTHER INFORMATION: X at position 16 is K, E, or D
<220> FEATURE:
<221> NAME/KEY: MISC_FEATURE
<222> LOCATION: (18)..(18)
<223> OTHER INFORMATION: X at position 18 is Q, H, or E
<220> FEATURE:
<221> NAME/KEY: MISC_FEATURE
<222> LOCATION: (19)..(19)
<223> OTHER INFORMATION: X at position 19 is T or S
<220> FEATURE:
<221> NAME/KEY: MISC_FEATURE
<222> LOCATION: (21)..(21)
<223> OTHER INFORMATION: X at position 21 is Q, K, or P
<220> FEATURE:
<221> NAME/KEY: MISC_FEATURE
<222> LOCATION: (22)..(22)
<223> OTHER INFORMATION: X at position 22 is R, K, M, T, or A
<220> FEATURE:
<221> NAME/KEY: MISC_FEATURE
<222> LOCATION: (25)..(25)
<223> OTHER INFORMATION: X at position 25 is D or E
<220> FEATURE:
<221> NAME/KEY: MISC_FEATURE
<222> LOCATION: (28)..(28)
<223> OTHER INFORMATION: X at position 28 is K or N
<220> FEATURE:
<221> NAME/KEY: MISC_FEATURE
<222> LOCATION: (29)..(29)
<223> OTHER INFORMATION: X at position 29 is I or V
<220> FEATURE:
<221> NAME/KEY: MISC_FEATURE
<222> LOCATION: (30)..(30)
<223> OTHER INFORMATION: X at position 30 is F, L, or I
<220> FEATURE:
<221> NAME/KEY: MISC_FEATURE
<222> LOCATION: (33)..(33)
<223> OTHER INFORMATION: X at position 33 is G, K, or E
<220> FEATURE:
<221> NAME/KEY: MISC_FEATURE
<222> LOCATION: (35)..(35)
<223> OTHER INFORMATION: X at position 35 is H or Q
<220> FEATURE:
<221> NAME/KEY: MISC_FEATURE
<222> LOCATION: (38)..(38)
<223> OTHER INFORMATION: X at position 38 is V or A
<220> FEATURE:
<221> NAME/KEY: MISC_FEATURE
<222> LOCATION: (40)..(40)
<223> OTHER INFORMATION: X at position 40 is Q or H
<220> FEATURE:
<221> NAME/KEY: MISC_FEATURE
<222> LOCATION: (41)..(41)
<223> OTHER INFORMATION: X at position 41 is V or I

<400> SEQUENCE: 10

Ala Xaa Gly Xaa Ser Xaa Trp Lys Xaa Ser Glu Gly Xaa Xaa Tyr Xaa
1               5                   10                  15

Asp Xaa Xaa Ser Xaa Xaa Glu Lys Xaa Asp Asp Xaa Xaa Xaa Pro Gly
            20                  25                  30

Xaa Ser Xaa Thr Tyr Xaa Trp Xaa Xaa
        35                  40

<210> SEQ ID NO 11
<211> LENGTH: 102
<212> TYPE: PRT
<213> ORGANISM: Porcine

<400> SEQUENCE: 11
```

-continued

Gln Val Asp Leu Gln Lys Thr Val Lys Val Thr Gly Ile Thr Thr Gln
1               5                   10                  15

Gly Val Lys Ser Leu Leu Ser Ser Met Tyr Val Lys Glu Phe Leu Val
                20                  25                  30

Ser Ser Ser Gln Asp Gly Arg Arg Trp Thr Leu Phe Leu Gln Asp Gly
            35                  40                  45

His Thr Lys Val Phe Gln Gly Asn Gln Asp Ser Ser Thr Pro Val Val
        50                  55                  60

Asn Ala Leu Asp Pro Pro Leu Phe Thr Arg Tyr Leu Arg Ile His Pro
65                  70                  75                  80

Thr Ser Trp Ala Gln His Ile Ala Leu Arg Leu Glu Val Leu Gly Cys
                85                  90                  95

Glu Ala Gln Asp Leu Tyr
            100

<210> SEQ ID NO 12
<211> LENGTH: 102
<212> TYPE: PRT
<213> ORGANISM: Canine

<400> SEQUENCE: 12

Gln Val Asp Phe Arg Lys Thr Met Lys Val Thr Gly Ile Thr Thr Gln
1               5                   10                  15

Gly Val Lys Ser Leu Leu Ile Ser Met Tyr Val Lys Glu Phe Leu Ile
                20                  25                  30

Ser Ser Ser Gln Asp Gly His Asn Trp Thr Leu Phe Leu Gln Asn Gly
            35                  40                  45

Lys Val Lys Val Phe Gln Gly Asn Arg Asp Ser Ser Thr Pro Val Arg
        50                  55                  60

Asn Arg Leu Glu Pro Pro Leu Val Ala Arg Tyr Val Arg Leu His Pro
65                  70                  75                  80

Gln Ser Trp Ala His His Ile Ala Leu Arg Leu Glu Val Leu Gly Cys
                85                  90                  95

Asp Thr Gln Gln Pro Ala
            100

<210> SEQ ID NO 13
<211> LENGTH: 102
<212> TYPE: PRT
<213> ORGANISM: Mouse

<400> SEQUENCE: 13

Gln Val Asp Leu Gln Lys Thr Met Lys Val Thr Gly Ile Ile Thr Gln
1               5                   10                  15

Gly Val Lys Ser Leu Phe Thr Ser Met Phe Val Lys Glu Phe Leu Ile
                20                  25                  30

Ser Ser Ser Gln Asp Gly His His Trp Thr Gln Ile Leu Tyr Asn Gly
            35                  40                  45

Lys Val Lys Val Phe Gln Gly Asn Gln Asp Ser Ser Thr Pro Met Met
        50                  55                  60

Asn Ser Leu Asp Pro Pro Leu Leu Thr Arg Tyr Leu Arg Ile His Pro
65                  70                  75                  80

Gln Ile Trp Glu His Gln Ile Ala Leu Arg Leu Glu Ile Leu Gly Cys
                85                  90                  95

Glu Ala Gln Gln Gln Tyr
            100

-continued

```
<210> SEQ ID NO 14
<211> LENGTH: 102
<212> TYPE: PRT
<213> ORGANISM: Rabbit

<400> SEQUENCE: 14

Gln Val Asp Leu Arg Lys Thr Met Lys Val Thr Gly Ile Thr Thr Gln
1               5                   10                  15

Gly Val Lys Ser Leu Leu Thr Ser Met Tyr Val Thr Glu Phe Leu Ile
            20                  25                  30

Ser Ser Ser Gln Asp Gly His His Trp Thr Leu Val Leu Gln Lys Gly
        35                  40                  45

Lys Leu Lys Val Phe Lys Gly Asn Gln Asp Ser Phe Thr Pro Val Leu
    50                  55                  60

Asn Ser Leu Asp Pro Pro Leu Leu Thr Arg Tyr Leu Arg Ile His Pro
65                  70                  75                  80

Lys Ser Trp Val His Gln Ile Ala Leu Arg Leu Glu Val Leu Gly Cys
                85                  90                  95

Glu Ala Gln Gln Leu Tyr
            100

<210> SEQ ID NO 15
<211> LENGTH: 102
<212> TYPE: PRT
<213> ORGANISM: Bat

<400> SEQUENCE: 15

Gln Val Asp Phe Gln Lys Thr Met Lys Val Thr Gly Ile Thr Thr Gln
1               5                   10                  15

Gly Val Lys Ser Leu Leu Thr Ser Met Tyr Val Lys Glu Phe Leu Ile
            20                  25                  30

Ser Ser Ser Gln Asp Gly His Asn Trp Thr Pro Phe Leu Gln Asn Gly
        35                  40                  45

Lys Val Lys Val Phe Gln Gly Asn Gln Asp Ser Phe Thr Pro Val Leu
    50                  55                  60

Asn Ser Leu Asp Pro Pro Leu Leu Thr Arg Tyr Leu Arg Ile His Pro
65                  70                  75                  80

Gln Ser Trp Val His Gln Ile Ala Leu Arg Leu Glu Val Leu Gly Cys
                85                  90                  95

Glu Ala Gln Gln Leu Tyr
            100

<210> SEQ ID NO 16
<211> LENGTH: 102
<212> TYPE: PRT
<213> ORGANISM: Rat

<400> SEQUENCE: 16

Gln Val Asp Leu Gln Arg Thr Val Lys Val Thr Gly Val Val Thr Gln
1               5                   10                  15

Gly Ala Arg Ser Leu Leu Thr Ala Met Phe Val Lys Lys Phe Leu Val
            20                  25                  30

Ser Thr Ser Gln Asp Gly Arg His Trp Thr His Val Leu Gln Asp Gly
        35                  40                  45

Lys Val Lys Val Phe Gln Gly Asn Arg Asp Ala Ser Thr Pro Met Val
    50                  55                  60

Asn Ser Leu His Pro Pro Arg Phe Thr Arg Tyr Leu Arg Ile His Pro
65                  70                  75                  80
```

-continued

```
Gln Val Trp Glu Arg Gln Ile Ala Leu Arg Leu Glu Ile Leu Gly Cys
                85                  90                  95
Glu Ala Gln Gln Leu Asp
            100

<210> SEQ ID NO 17
<211> LENGTH: 102
<212> TYPE: PRT
<213> ORGANISM: Sheep

<400> SEQUENCE: 17

Gln Val Asp Phe Gln Lys Thr Met Arg Val Thr Gly Ile Thr Thr Gln
1               5                   10                  15

Gly Val Lys Ser Leu Leu Thr Ser Met Tyr Val Lys Glu Phe Leu Ile
            20                  25                  30

Ser Ser Ser Gln Glu Gly His Asn Trp Thr Pro Phe Leu Gln Asn Gly
        35                  40                  45

Lys Val Lys Val Phe Gly Asn Gln Asp Ser Phe Thr Pro Val Val
    50                  55                  60

Asn Thr Leu Asp Pro Pro Leu Phe Thr Arg Phe Leu Arg Ile His Pro
65                  70                  75                  80

Gln Ser Trp Val His His Ile Ala Leu Arg Leu Glu Phe Trp Gly Cys
                85                  90                  95

Glu Ala Gln Gln Gln Tyr
            100

<210> SEQ ID NO 18
<211> LENGTH: 102
<212> TYPE: PRT
<213> ORGANISM: Artificial
<220> FEATURE:
<223> OTHER INFORMATION: Consensus
<220> FEATURE:
<221> NAME/KEY: MISC_FEATURE
<222> LOCATION: (4)..(4)
<223> OTHER INFORMATION: X at position 4 is Q or R
<220> FEATURE:
<221> NAME/KEY: MISC_FEATURE
<222> LOCATION: (5)..(5)
<223> OTHER INFORMATION: X at position 5 is K or R
<220> FEATURE:
<221> NAME/KEY: MISC_FEATURE
<222> LOCATION: (8)..(8)
<223> OTHER INFORMATION: X at position 8 is M or V
<220> FEATURE:
<221> NAME/KEY: MISC_FEATURE
<222> LOCATION: (9)..(9)
<223> OTHER INFORMATION: X at position 9 is K or R
<220> FEATURE:
<221> NAME/KEY: MISC_FEATURE
<222> LOCATION: (13)..(13)
<223> OTHER INFORMATION: X at position 13 is V or I
<220> FEATURE:
<221> NAME/KEY: MISC_FEATURE
<222> LOCATION: (14)..(14)
<223> OTHER INFORMATION: X at position 14 is T or V
<220> FEATURE:
<221> NAME/KEY: MISC_FEATURE
<222> LOCATION: (18)..(18)
<223> OTHER INFORMATION: X at position 18 is A or V
<220> FEATURE:
<221> NAME/KEY: MISC_FEATURE
<222> LOCATION: (19)..(19)
<223> OTHER INFORMATION: X at position 19 is R or K
<220> FEATURE:
<221> NAME/KEY: MISC_FEATURE
<222> LOCATION: (22)..(22)
<223> OTHER INFORMATION: X at position 22 is L or F
<220> FEATURE:
<221> NAME/KEY: MISC_FEATURE
```

```
<222> LOCATION: (23)..(23)
<223> OTHER INFORMATION: X at position 23 is T, S, or I
<220> FEATURE:
<221> NAME/KEY: MISC_FEATURE
<222> LOCATION: (24)..(24)
<223> OTHER INFORMATION: X at position 24 is S or A
<220> FEATURE:
<221> NAME/KEY: MISC_FEATURE
<222> LOCATION: (26)..(26)
<223> OTHER INFORMATION: X at position 26 is F or Y
<220> FEATURE:
<221> NAME/KEY: MISC_FEATURE
<222> LOCATION: (28)..(28)
<223> OTHER INFORMATION: X at position 28 is K or T
<220> FEATURE:
<221> NAME/KEY: MISC_FEATURE
<222> LOCATION: (29)..(29)
<223> OTHER INFORMATION: X at position 29 is E or K
<220> FEATURE:
<221> NAME/KEY: MISC_FEATURE
<222> LOCATION: (32)..(32)
<223> OTHER INFORMATION: X at position 32 is I or V
<220> FEATURE:
<221> NAME/KEY: MISC_FEATURE
<222> LOCATION: (34)..(34)
<223> OTHER INFORMATION: X at position 34 is S or T
<220> FEATURE:
<221> NAME/KEY: MISC_FEATURE
<222> LOCATION: (37)..(37)
<223> OTHER INFORMATION: X at position 37 is D or E
<220> FEATURE:
<221> NAME/KEY: MISC_FEATURE
<222> LOCATION: (39)..(39)
<223> OTHER INFORMATION: X at position 39 is H or R
<220> FEATURE:
<221> NAME/KEY: MISC_FEATURE
<222> LOCATION: (40)..(40)
<223> OTHER INFORMATION: X at position 40 is Q, R, H, or N
<220> FEATURE:
<221> NAME/KEY: MISC_FEATURE
<222> LOCATION: (43)..(43)
<223> OTHER INFORMATION: X at position 43 is L, Q, P, or H
<220> FEATURE:
<221> NAME/KEY: MISC_FEATURE
<222> LOCATION: (44)..(44)
<223> OTHER INFORMATION: X at position 44 is F, I, or V
<220> FEATURE:
<221> NAME/KEY: MISC_FEATURE
<222> LOCATION: (45)..(45)
<223> OTHER INFORMATION: X at position 45 is F or L
<220> FEATURE:
<221> NAME/KEY: MISC_FEATURE
<222> LOCATION: (46)..(46)
<223> OTHER INFORMATION: X at position 46 is Q or Y
<220> FEATURE:
<221> NAME/KEY: MISC_FEATURE
<222> LOCATION: (47)..(47)
<223> OTHER INFORMATION: X at position 47 is N, D, or K
<220> FEATURE:
<221> NAME/KEY: MISC_FEATURE
<222> LOCATION: (49)..(49)
<223> OTHER INFORMATION: X at position 49 is H or K
<220> FEATURE:
<221> NAME/KEY: MISC_FEATURE
<222> LOCATION: (50)..(50)
<223> OTHER INFORMATION: X at position 50 is V, T, or L
<220> FEATURE:
<221> NAME/KEY: MISC_FEATURE
<222> LOCATION: (54)..(54)
<223> OTHER INFORMATION: X at position 54 is Q or K
<220> FEATURE:
<221> NAME/KEY: MISC_FEATURE
<222> LOCATION: (57)..(57)
<223> OTHER INFORMATION: X at position 57 is Q or R
<220> FEATURE:
<221> NAME/KEY: MISC_FEATURE
<222> LOCATION: (59)..(59)
<223> OTHER INFORMATION: X at position 59 is S or A
<220> FEATURE:
<221> NAME/KEY: MISC_FEATURE
```

```
<222> LOCATION: (60)..(60)
<223> OTHER INFORMATION: X at position 60 is S or F
<220> FEATURE:
<221> NAME/KEY: MISC_FEATURE
<222> LOCATION: (63)..(63)
<223> OTHER INFORMATION: X at position 63 is M or V
<220> FEATURE:
<221> NAME/KEY: MISC_FEATURE
<222> LOCATION: (64)..(64)
<223> OTHER INFORMATION: X at position 64 is V, R, M, or L
<220> FEATURE:
<221> NAME/KEY: MISC_FEATURE
<222> LOCATION: (66)..(66)
<223> OTHER INFORMATION: X at position 66 is S, A, R, or T
<220> FEATURE:
<221> NAME/KEY: MISC_FEATURE
<222> LOCATION: (68)..(68)
<223> OTHER INFORMATION: X at position 68 is D, E, or H
<220> FEATURE:
<221> NAME/KEY: MISC_FEATURE
<222> LOCATION: (71)..(71)
<223> OTHER INFORMATION: X at position 71 is L or R
<220> FEATURE:
<221> NAME/KEY: MISC_FEATURE
<222> LOCATION: (72)..(72)
<223> OTHER INFORMATION: X at position 72 is L, F, or V
<220> FEATURE:
<221> NAME/KEY: MISC_FEATURE
<222> LOCATION: (73)..(73)
<223> OTHER INFORMATION: X at position 73 is T or A
<220> FEATURE:
<221> NAME/KEY: MISC_FEATURE
<222> LOCATION: (75)..(75)
<223> OTHER INFORMATION: X at position 75 is Y or F
<220> FEATURE:
<221> NAME/KEY: MISC_FEATURE
<222> LOCATION: (76)..(76)
<223> OTHER INFORMATION: X at position 76 is L or V
<220> FEATURE:
<221> NAME/KEY: MISC_FEATURE
<222> LOCATION: (78)..(78)
<223> OTHER INFORMATION: X at position 78 is I or L
<220> FEATURE:
<221> NAME/KEY: MISC_FEATURE
<222> LOCATION: (81)..(81)
<223> OTHER INFORMATION: X at position 81 is Q, T, or K
<220> FEATURE:
<221> NAME/KEY: MISC_FEATURE
<222> LOCATION: (82)..(82)
<223> OTHER INFORMATION: X at position 82 is S, I, or V
<220> FEATURE:
<221> NAME/KEY: MISC_FEATURE
<222> LOCATION: (84)..(84)
<223> OTHER INFORMATION: X at position 84 is V, A, or E
<220> FEATURE:
<221> NAME/KEY: MISC_FEATURE
<222> LOCATION: (85)..(85)
<223> OTHER INFORMATION: X at position 85 is H, Q, or R
<220> FEATURE:
<221> NAME/KEY: MISC_FEATURE
<222> LOCATION: (86)..(86)
<223> OTHER INFORMATION: X at position 86 is is Q or H
<220> FEATURE:
<221> NAME/KEY: MISC_FEATURE
<222> LOCATION: (91)..(91)
<223> OTHER INFORMATION: X at position 91 is M or L
<220> FEATURE:
<221> NAME/KEY: MISC_FEATURE
<222> LOCATION: (93)..(93)
<223> OTHER INFORMATION: X at position 93 is V, I, or F
<220> FEATURE:
<221> NAME/KEY: MISC_FEATURE
<222> LOCATION: (94)..(94)
<223> OTHER INFORMATION: X at position 94 is L or W
<220> FEATURE:
<221> NAME/KEY: MISC_FEATURE
<222> LOCATION: (97)..(97)
<223> OTHER INFORMATION: X at position 97 is E or D
<220> FEATURE:
<221> NAME/KEY: MISC_FEATURE
```

```
<222> LOCATION: (98)..(98)
<223> OTHER INFORMATION: X at position 98 is A or T
<220> FEATURE:
<221> NAME/KEY: MISC_FEATURE
<222> LOCATION: (100)..(100)
<223> OTHER INFORMATION: X at position 100 is D or Q
<220> FEATURE:
<221> NAME/KEY: MISC_FEATURE
<222> LOCATION: (101)..(101)
<223> OTHER INFORMATION: X at position 101 is L, P, or Q
<220> FEATURE:
<221> NAME/KEY: MISC_FEATURE
<222> LOCATION: (102)..(102)
<223> OTHER INFORMATION: X at position 102 is Y, A, or D

<400> SEQUENCE: 18

Gln Val Asp Xaa Xaa Lys Thr Xaa Xaa Val Thr Gly Xaa Xaa Thr Gln
1               5                   10                  15

Gly Xaa Xaa Ser Leu Xaa Xaa Xaa Met Xaa Val Xaa Xaa Phe Leu Xaa
            20                  25                  30

Ser Xaa Ser Gln Xaa Gly Xaa Xaa Trp Thr Xaa Xaa Xaa Xaa Gly
        35                  40                  45

Xaa Xaa Lys Val Phe Xaa Gly Asn Xaa Asp Xaa Xaa Thr Pro Xaa Xaa
    50                  55                  60

Asn Xaa Leu Xaa Pro Pro Xaa Xaa Xaa Arg Xaa Xaa Arg Xaa His Pro
65                  70                  75                  80

Xaa Xaa Trp Xaa Xaa Xaa Ile Ala Leu Arg Xaa Glu Xaa Xaa Gly Cys
                85                  90                  95

Xaa Xaa Gln Xaa Xaa Xaa
            100

<210> SEQ ID NO 19
<211> LENGTH: 3
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (2)..(2)
<223> OTHER INFORMATION: X at position 2 is T, G, A, M, C, F, L, V, OR I

<400> SEQUENCE: 19

Lys Xaa Ser
1

<210> SEQ ID NO 20
<211> LENGTH: 4
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (2)..(2)
<223> OTHER INFORMATION: X at position 2 is Q, K, P, E, D, N, H, Y, W,
      S, T, G, A, M, C, F, L, V, or I
<220> FEATURE:
<221> NAME/KEY: MISC_FEATURE
<222> LOCATION: (3)..(3)
<223> OTHER INFORMATION: X at position 3 can be any amino acid other
      than R
<220> FEATURE:
<221> NAME/KEY: MISC_FEATURE
<222> LOCATION: (4)..(4)
<223> OTHER INFORMATION: X at position 4 is E, Q, D, N, H, P, Y, W, S,
      T, G, A, M, C, F, L, V, or I

<400> SEQUENCE: 20
```

```
Ser Xaa Xaa Xaa
1

<210> SEQ ID NO 21
<211> LENGTH: 4
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (3)..(3)
<223> OTHER INFORMATION: X at position 3 is M, C, F, L, V, or I

<400> SEQUENCE: 21

Thr Tyr Xaa Trp
1

<210> SEQ ID NO 22
<211> LENGTH: 3
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (1)..(1)
<223> OTHER INFORMATION: X at position 1 can be any amino acid other
      than K or R

<400> SEQUENCE: 22

Xaa Val Thr
1

<210> SEQ ID NO 23
<211> LENGTH: 4
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (3)..(3)
<223> OTHER INFORMATION: X at position 3 can be any amino acid besides
      L or R
<220> FEATURE:
<221> NAME/KEY: MISC_FEATURE
<222> LOCATION: (4)..(4)
<223> OTHER INFORMATION: X at position 4 is L, V, or I

<400> SEQUENCE: 23

Pro Pro Xaa Xaa
1

<210> SEQ ID NO 24
<211> LENGTH: 4
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (1)..(1)
<223> OTHER INFORMATION: X at position 1 is E, D, Q, N, H, P, Y, W, S,
      T, G, A, M, C, F, L, V, or I
<220> FEATURE:
<221> NAME/KEY: MISC_FEATURE
<222> LOCATION: (2)..(2)
<223> OTHER INFORMATION: X at position 2 is A, T, G, M, C, F, L, V, or I
<220> FEATURE:
<221> NAME/KEY: MISC_FEATURE
<222> LOCATION: (4)..(4)
<223> OTHER INFORMATION: X at position 4 is D, Q, N, H, P, Y, W, S, T,
```

G, A, M, C, F, L, V, or I

<400> SEQUENCE: 24

Xaa Xaa Gln Xaa
1

<210> SEQ ID NO 25
<211> LENGTH: 4
<212> TYPE: PRT
<213> ORGANISM: Artificial
<220> FEATURE:
<223> OTHER INFORMATION: Mutant
<220> FEATURE:
<221> NAME/KEY: MISC_FEATURE
<222> LOCATION: (2)..(2)
<223> OTHER INFORMATION: X at position 2 can be Q, K, P, E, D, N, H, Y,
      W, S, T, G, A, M, C, F, L, V, or I
<220> FEATURE:
<221> NAME/KEY: MISC_FEATURE
<222> LOCATION: (3)..(3)
<223> OTHER INFORMATION: X at position 3 is cysteine

<400> SEQUENCE: 25

Ser Xaa Xaa Glu
1

<210> SEQ ID NO 26
<211> LENGTH: 7
<212> TYPE: PRT
<213> ORGANISM: Artificial
<220> FEATURE:
<223> OTHER INFORMATION: Mutant

<400> SEQUENCE: 26

Val Asp Gln Arg Gly Asn Gln
1               5

<210> SEQ ID NO 27
<211> LENGTH: 7
<212> TYPE: PRT
<213> ORGANISM: Artificial
<220> FEATURE:
<223> OTHER INFORMATION: Mutant

<400> SEQUENCE: 27

Val Asp Gln Arg Met Lys Asn
1               5

<210> SEQ ID NO 28
<211> LENGTH: 7
<212> TYPE: PRT
<213> ORGANISM: Artificial
<220> FEATURE:
<223> OTHER INFORMATION: Mutant

<400> SEQUENCE: 28

Pro Gln Leu Arg Gly Asn Gln
1               5

<210> SEQ ID NO 29
<211> LENGTH: 7
<212> TYPE: PRT
<213> ORGANISM: Artificial
<220> FEATURE:
<223> OTHER INFORMATION: Mutant

<400> SEQUENCE: 29

Pro Asp Leu Arg Met Lys Asn
1               5

```
<210> SEQ ID NO 30
<211> LENGTH: 7
<212> TYPE: PRT
<213> ORGANISM: Artificial
<220> FEATURE:
<223> OTHER INFORMATION: Mutant

<400> SEQUENCE: 30

Pro Gln Gln Arg Met Lys Asn
1               5

<210> SEQ ID NO 31
<211> LENGTH: 7
<212> TYPE: PRT
<213> ORGANISM: Artificial
<220> FEATURE:
<223> OTHER INFORMATION: Mutant

<400> SEQUENCE: 31

Pro Gln Arg Arg Met Lys Asn
1               5

<210> SEQ ID NO 32
<211> LENGTH: 7
<212> TYPE: PRT
<213> ORGANISM: Artificial
<220> FEATURE:
<223> OTHER INFORMATION: Mutant

<400> SEQUENCE: 32

Pro Gln Leu Arg Gly Lys Asn
1               5

<210> SEQ ID NO 33
<211> LENGTH: 7
<212> TYPE: PRT
<213> ORGANISM: Artificial
<220> FEATURE:
<223> OTHER INFORMATION: Mutant

<400> SEQUENCE: 33

Pro Gln Leu Arg Met Ile Asn
1               5

<210> SEQ ID NO 34
<211> LENGTH: 7
<212> TYPE: PRT
<213> ORGANISM: Artificial
<220> FEATURE:
<223> OTHER INFORMATION: Mutant

<400> SEQUENCE: 34

Pro Gln Leu Arg Met Asn Asn
1               5
```